US011279935B2

(12) United States Patent
Akiyama et al.

(10) Patent No.: US 11,279,935 B2
(45) Date of Patent: Mar. 22, 2022

(54) METHOD FOR SCREENING PROPHYLACTIC OR THERAPEUTIC AGENTS FOR DISEASES CAUSED BY INTERLEUKIN 6, INTERLEUKIN 13, TNF, G-CSF, CXCL1, CXCL2, OR CXCL5 AND AGENT FOR THE PREVENTION OR TREATMENT OF DISEASES CAUSED BY INTERLEUKIN 6, INTERLEUKIN 13, TNF, G-CSF, CXCL1, CXCL2, OR CXCL5

(71) Applicants: TAK-CIRCULATOR CO., LTD, Tokyo (JP); UNIVERSITY OF TOKYO, Tokyo (JP)

(72) Inventors: Tetsu Akiyama, Tokyo (JP); Hiroaki Harada, Tokyo (JP); Yusuke Yamazumi, Tokyo (JP); Takeaki Oda, Tokyo (JP); Oh Sasaki, Tokyo (JP); Kazuyoshi Kofu, Tokyo (JP)

(73) Assignees: TAK-CIRCULATOR CO, LTD, Tokyo (JP); UNIVERSITY OF TOKYO, Tokyo (JP)

( * ) Notice: Subject to any disclaimer, the term of this patent is extended or adjusted under 35 U.S.C. 154(b) by 176 days.

(21) Appl. No.: 16/315,513

(22) PCT Filed: Jul. 7, 2017

(86) PCT No.: PCT/JP2017/025015
§ 371 (c)(1),
(2) Date: Jan. 4, 2019

(87) PCT Pub. No.: WO2018/008750
PCT Pub. Date: Jan. 11, 2018

(65) Prior Publication Data
US 2020/0325479 A1 Oct. 15, 2020

(30) Foreign Application Priority Data
Jul. 8, 2016 (JP) .............................. JP2016-136402

(51) Int. Cl.
*C12N 15/113* (2010.01)
*A61P 11/06* (2006.01)
*C12Q 1/6883* (2018.01)
*G01N 33/50* (2006.01)

(52) U.S. Cl.
CPC .......... *C12N 15/1136* (2013.01); *A61P 11/06* (2018.01); *C12Q 1/6883* (2013.01); *G01N 33/5094* (2013.01); *C12Q 2600/16* (2013.01)

(58) Field of Classification Search
None
See application file for complete search history.

(56) References Cited

U.S. PATENT DOCUMENTS

| | | |
|---|---|---|
| 8,962,244 B2 | 2/2015 | Ryder |
| 2003/0049662 A1 | 3/2003 | Monia et al. |
| 2003/0152956 A1 | 8/2003 | Ohtani et al. |
| 2005/0261219 A1 | 11/2005 | Richards et al. |
| 2006/0172930 A1 | 8/2006 | Akiyama et al. |
| 2009/0118213 A1 | 5/2009 | Hansen et al. |
| 2011/0200612 A1 | 8/2011 | Schuster et al. |
| 2011/0256063 A1 | 10/2011 | Lu et al. |
| 2012/0183538 A1 | 7/2012 | Trieu et al. |
| 2012/0244170 A1 | 9/2012 | Ciosk et al. |
| 2014/0350083 A1 | 11/2014 | Fire et al. |
| 2021/0079390 A1* | 3/2021 | Akiyama ................ A61P 11/06 |

FOREIGN PATENT DOCUMENTS

| | | |
|---|---|---|
| JP | 2002508944 A | 3/2002 |
| JP | 2003520586 A | 7/2003 |
| JP | 415 5561 | 7/2008 |
| JP | 2009507499 A | 2/2009 |
| JP | 44-29269 B2 | 12/2009 |
| JP | 2011-526892 A | 10/2011 |
| JP | 2012532613 A | 12/2012 |
| WO | 1999032619 A1 | 7/1999 |
| WO | WO09949065 A | 9/1999 |
| WO | WO2002031136 A1 | 4/2002 |
| WO | 2003040182 A1 | 5/2003 |
| WO | 2018 155 710 | 10/2015 |

OTHER PUBLICATIONS

Hagedorn et al. Nucleic Acids Research vol. 45, pp. 2262-2282 (Year: 2017).*
Fakhr et al. Cancer Gene Therapy 23, 73-82 (Year: 2016).*
Qiu, et al., "Bronchial Mucosal Inflammation and Upregulation of CXC Chemoattractants and Receptors in Severe Exacerbations of Asthma," Thorax, 2007, 62: 475-482.
Chung, et al., "Cytokines in Asthma," Thorax, 1999, 54: 825-857.
Corren, et al., "Lebrikizumab Treatment in Adults with Asthma," New England Journal of Medicine, 2011, 365: 1088-98.
Shifren, et al., "Mechanisms of Remodeling in Asthmatic Airways," Journal of Allergy, vol. 2012, Article ID 316049, 12 pages.
Zhu, et al., "Mex3B: A Coreceptor to Present dsRNA to TLR3," Cell Research, 2016, 26: 391-392.
Sadik, et al., "Neutrophils Cascading their Way to Inflammation," Trends Immunol, Oct. 2011, 32(10): 452-460.

(Continued)

*Primary Examiner* — Brian Whiteman
(74) *Attorney, Agent, or Firm* — Emerson Thomson Bennett; Daniel A. Thomson

(57) ABSTRACT

Provided are a method for screening agents for the prevention or treatment of diseases caused by interleukin 6, interleukin 13, TNF, G-CSF, CXCL1, CXCL2, or CXCL5 and an agent for the prevention or treatment of diseases caused by interleukin 6, interleukin 13, TNF, G-CSF, CXCL1, CXCL2, or CXCL5. A method for screening agents for the prevention or treatment of diseases caused by interleukin 6, interleukin 13, TNF, G-CSF, CXCL1, CXCL2, or CXCL5 having as the index at least one selected from the group consisting of changes in the expression of the MEX3B gene or MEX3B protein and changes in the function of the MEX3B protein.

4 Claims, 5 Drawing Sheets

Specification includes a Sequence Listing.

(56) References Cited

OTHER PUBLICATIONS

Robinson, et al., Predominant TH2-Like Bronchoalveolar T-Lymphocyte Population in Atopic Asthma, New England Journal of Medicine, Jan. 30, 1992, 298-304.
LeBorgne, et al., "RNA-Binding Protein Mex3b Regulates the Spatial Organization of the Rap1 Pathway," Company of Biologists LTD Development, 2014, 141, 2096-2017.
Yamazumi, et al., "RNA Binding Protein Mex-3B is Required for IL-33 Induction in the Development of Allergic Airway Inflammation," Cell Reports 16, 2456-2471, Aug. 30, 2016.
Brightling et al., "Targeting TNF-a: A Novel Therapeutic Approach for Asthma," J Allergy Clin Immunol., Jan. 2008: 121(1): 5-12.
Morishima, et al., "Th17-Associated Cytokines as a Therapeutic Target for Steroid-Insensitive Asthma," Clinical and Developmental Immunology, vol. 2013, Article ID 609395, 9 pages.
Al-Ramli, et al., "TH-17 Cell-Related Cytokines' Potential Role in the Pathogenesis of Severe Asthama," Journal of Asthma, 2008, 45:sup1, 41-44.
Bradley, J R. "TNF-Mediated Inflammatory Disease," Journal of Pathology, 2008, 214: 149-160.
WIPO, WO 2018 008750, "International Search Report of PCT/JP2017/025015", dated Jan. 11, 2018.
JP Patent Office, "Notificaton of Reasons for Refusal," JP2017-559904, dated Mar. 13, 2018.
Yan Yang et al: "The RNA-binding protein Mex3b is a coreceptor of Toll-like receptor 3 in innate antiviral response", Cell Research-Xibao Yanjiu, vol. 26, No. 3, Jan. 29, 2016, pp. 288-303, XP055596004.
S. Kang et al: "Therapeutic uses of anti-interleukin-6 receptor antibody", International Immunology, vol. 27, No. 1, Aug. 20, 2014, pp. 21-29, XP055377592.
Supplementary European Search Report issued in the EP Patent Application No. EP17824353.1, dated Jun. 25, 2019.
Office Action issued in the EP Patent Application No. EP17824353.1, dated Jul. 16, 2019.
Abstract of WO2010005527 published Jan. 14, 2010.
Abstract of US2006172930, published Aug. 3, 2006.
Buchet-Poyau, et al., "Identification and Characterization of Human Mex-3 Proteins, a Novel Family of Evolutionarily Conserved RNA-Binding Proteins Differentially Localized to Processing Bodies," Nucleic Acids Research, 2007, vol. 35, No. 4, pp. 1289-1300.
Mandiyan, et al., "Molecular and Cellular Characterization of Baboon C-Raf as a Target for Antiproliferative Effects of Antisense Oligonucleotides," Antisense & Nucleic Acid Drug Development, Mary Ann Liebert, Inc., 1997, vol. 7, pp. 539-548.
Wolozin, et al., "Participation of Presenilin 2 in Apoptosis: Enhanced Basal Activity Conferred by an Alzheimer Mutation," Science 1996, vol. 278, pp. 1710-1713.
Yoon, et al., "Scaffold Function of Long Non-Coding RNA HOTYAIR in Protein Ubiquitination," Nature Communications, 2013, vol. 4.2939, pp. 1-14.
Yamazumi, et al., "The RNA Binding Protein Mex-3B is Required for IL-33 mInduction in the Development of Allergic Airway Inflammation," Cell Reports, 2016, vol. 16, pp. 2456-2471.
International Search Report dated Sep. 27, 2017 for International Application Serial No. PCT/JP2017/025014.
Translation of International Search Report dated Sep. 27, 2017 for International Application Serial No. PCT/JP2017/025014.
Draper, et al., "MEX-3 is a KH Domain Protein that Regulates Blastomerre Identity in Early C. Elegans Embryos," Cell, 1996, vol. 87, pp. 205-216.
Supplementary European Search Report dated Apr. 11, 2019 for Application Serial No. EP17824352.
European Office Action dated May 21, 2019 for Application Serial No. EP17824352.
U.S. Office Action dated Apr. 30, 2021 for U.S. Appl. No. 16/315,594.
Kurreck, J. et al.; "Design of antisense oligonucleotides stablized by locked nucleic acids", Nucleic Acids Research; 2002; vol. 30(9); p. 1911-1918.
Seth, P. et al.; "Structure Activity Relationships of a-L-LNA Modified Phoshporothioate Gapmer Antisense Oligoncucleotides in Animals"; Molecular Theerapy-Nucleic Acids; 2012; vol. 1, e47; p. 1-8.

\* cited by examiner

FIG. 7
PATHOLOGICAL TISSUE ANALYSIS OF LUNG TISSUES
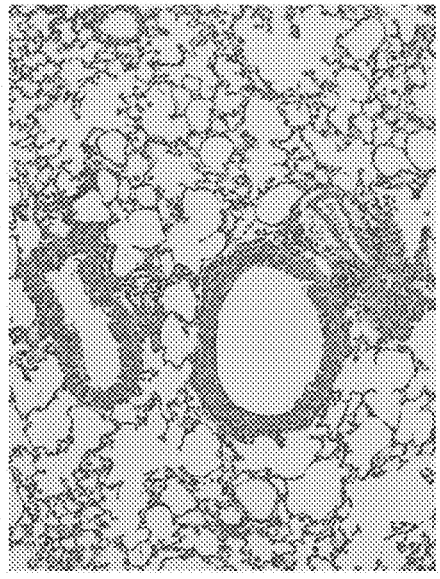
OVA INHALATION–
PBS ADMINISTRATION GROUP
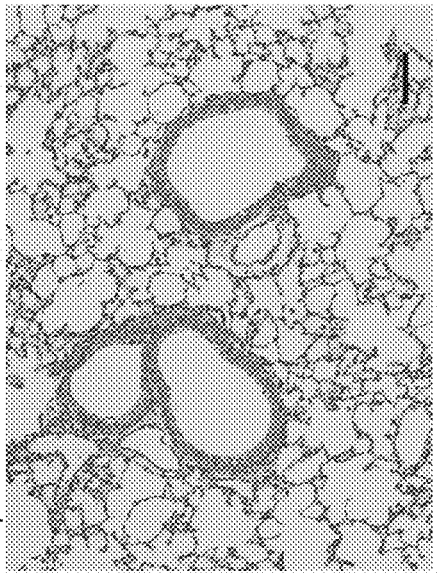
OVA INHALATION–MEX3B SPECIFIC
Gapmer ADMINISTRATION GROUP
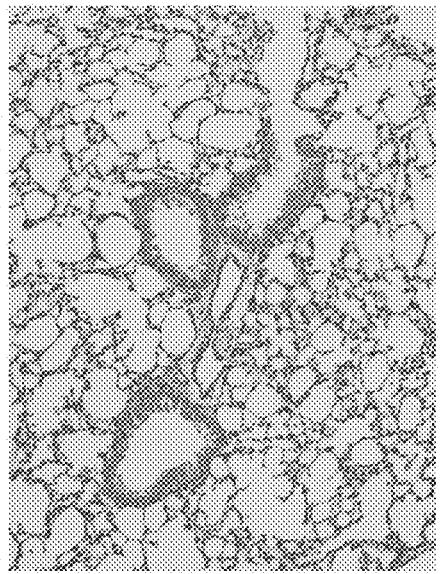
CONTROL INHALATION GROUP
OVA INHALATION–Gapmer (CONTROL)
ADMINISTRATION GROUP
SCALE BAR = 20 μm

SEQUENCE LISTING

```
<160> NUMBER OF SEQ ID NOS: 28

<210> SEQ ID NO 1
<211> LENGTH: 3532
<212> TYPE: DNA
<213> ORGANISM: Human

<400> SEQUENCE: 1
tcaagaggcg gggaggagag gaggaaaaag cgctgagtga gggcgggcgg gcgggcggga      60
gggagggagt ggaggagccg gggaggggct ccttaaagaa acgcttctgt cgctcgcctg     120
ctcgcttttc gctcggcatt gcggccagcc agccgggcac tcgggggca cgcgcggcca     180 ccgctagagc tctgcccca ccccacccgc cagcaggtct ggggtgggga cccaggtggg     240
ggctcctgca gccactgccc ggtgcggacc gcacggagcg acccactcct cccagcaccg     300
aggaagaagc aacggagccc tcagcaggcg accgcctcc ccgcccctga ccacccgctt     360
cccggctgcc tttgtggccg cagcttctcg ccgccgagcc gagggccggc ggggcgcgg     420 cgcgcacggc cgagcgatgc ccagctcgct gttcgcagac ctggagcgca acggcagcgg     480
cggcggcggc ggcggcagca gcggaggggg agagaccctg gatgaccaaa gagccctgca     540
gctcgcgctc gaccagctct ccctgctggg gctggacagt gacgagggcg cctctctgta     600
cgacagcgag ccgcgcaaga agagcgtgaa catgaccgag tgcgtgccag tacccagttc     660
tgagcatgtc gccgagatcg tggggcggca aggttgtaaa atcaaagcgc tgcgggcgaa     720
gaccaatact tacatcaaga ccccagttcg cggggaggag cctgtctttg ttgtgacggg     780
caggaaggag gatgtggcca tggctcggag ggagatcatc tctgctgccg agcacttctc     840
catgatccgc gcctcccgga ataagaacac ggcactcaac ggcgcggtgc ctgggccgcc     900
caacctgccc gggcagacca ccatccaagt gcgggtaccc taccgcgtgg tggggctcgt     960
ggtggggccc aaaggcgcca caatcaagcg catccagcag cagacgcaca cgtacatcgt    1020
gacgcccagc cgggataagg agccggtgtt cgaggtgacc ggcatgccag agaacgtgga    1080
tcgcgctcga gaggagattg aggcgcacat tgctctgcgt accggcggca tcattgagct    1140
cacagacgag aacgacttcc acgccaacgg caccgatgtg ggcttcgatc tgcatcatgg    1200
gtccggcggg tccggcccag gcagcctctg gagcaagccc accccagca tcacgcccac    1260 ccccggccgc aagcctttct ctagctaccg caacgacagc tccagctcgc ttggcagtgc    1320
ttccacagac tcttatttcg gcggcgggac cagcagcagc gcagcggcta cccagcgcct    1380
ggcggactac agccccccta gcccgccct gagctttgcg cacaacggaa acaataacaa    1440
taacggcaat gggtacacct acacagcggg gggagaagcc tcagtgccat ccccgacgg    1500 ctgccccgag ctgcagccca cttttgaccc ggctcccgct ccccacctg gggcaccact    1560
```

```
tatctgggcc cagttcgagc ggtccccggg aggcggacct gcagctccgg tatcttcttc    1620
ctgctcttct tctgcatctt cgtctgcttc ttcctcctcc gtggtcttcc ccggggtgg     1680
cgccagtgcg ccctccaacg ccaacctggg gctattggtg caccgccggc tgcaccctgg    1740
caccagctgc ccgcgcctgt ctccaccctt gcacatggcc ccggggcgg gagagcacca    1800
cctggctcgc cgggtgcgca cgacccggg tggaggaggc ctggcctacg ccgcttatgc    1860
caacgggctg ggggcacagc tgcctggctt gcagccgtcg gacacgtcgg gctcctcctc    1920
ttcgtccagc tcctcctcca gctcttcatc ctcttcctcc gggcttcggc gtaaaggcag    1980
ccgcgactgc tccgtgtgct tcgagagcga agtgattgcc gcgctggtgc cctgtggcca    2040
caacctcttc tgcatggagt gcgccaatcg catctgtgag aagagcgagc ccgagtgccc    2100
ggtctgccac accgcggtca ctcaggccat ccgcatcttt tcttaaaggc agcgggcgct    2160
gctagtgcgc accgtgctgg gggaagggg aaccctccc catcctcttt ccccagcgct     2220
cgcctgcctc cctgggtgcc cccctctcc cttctcttc ccggcccac caacactctg       2280
agatccgaga ggagcttgga aagctgtagt atccgctcat ttttaaaatt taattttaa    2340
gtaaaggaat ttgccaggat atctgcatca agagtactgt agcctgggaa acctgaacac    2400
ctgaaatgca tgctctataa ataataggaa cggcgacatt ctagtaatga tagttttac    2460
actgtactta ataggaagct tccaaaagaa gaaaacccca caagttttcc attttcttaa    2520
agtaggaaaa aatgaacagt aataattatg atgaagatga tagtagtgct atgggatgtg    2580
tggactgttt agtgtgttcc cctttgtggg tgggttccta tgatacttat tatagaacac    2640
agtggatcct ttttgaatgt tcgtggaagg gccaggagtt cctgtgaaac caggatactg    2700
cagctttatt aaagttaaag aaactgtaac atatctctta tatattaaaa acgtttaaaa    2760
gttttaaaga gaaattgcat taatacagat tgaagtattt tattcttttt tgacttgaaa    2820
aattatattt catattgcaa agatgtttac aagtatttta atttaagttc agtgaacttt    2880
tttgtagctg ggtaaatct ttttattta gtatggcctt atggcaaaga acactgtatt      2940
attttaataa tcacacaatt gtgacggaat acaaccata aaatgtgtaa tgttttgaac     3000
agtattctgt tgggatggag attttatagg ttcagacaaa tcttctagat ctgcttcacc    3060
cagcatattt tctattcagt gatataaagc atatttttatt ctatattatt acaaaaacgg   3120
aaatgtataa acatgtcaaa aagaactgtt gatgctttct aacatttgta taaatagaat    3180
tcagtgcaag ttacaaaaat tctgttgcac cactctagtt ttagtatttc tattttaata    3240
catttgttta ccactgtttt atgtatatgt aggtgatgtt acttgagctt aaatgtactt    3300
tactgagcaa agtttaaaaa acaaagtata ttttatttta tgataaaggg cctttaacct    3360
catggtcaaa tactaatatt atatttgctg agacaagatt tgaaattgta tcaagagttt    3420
tattttctg acatttaaag ttctacataa taaaggtaaa acttaagtaa tggtgctact     3480
tcatttttta agtatttcta tataaataaa atattgaaga aaatcttaaa aa             3532
```

<210> SEQ ID NO 2  
<211> LENGTH: 35919  
<212> TYPE: DNA  
<213> ORGANISM: Human

<400> SEQUENCE: 2

```
ctccaggtgt gttactgaat aacaacaaca ataatggaat agtttgaaat gccaggcaca      60
gtctgaagtg tgttatagac ttgtattatc tcactcaagc ctcacagcat ccctgcgtga     120
aggtggaatc attatcccaa atttgcagac aagactgagg ctcagagaga tcagtaagta    180
```

```
gtagagctga gattcaagcc tggattcgct tgactccgta gtccatgtac taactaacca      240
ctaggttaaa ctcccttgtt gggcctgacc catgaattgg aaaaccagaa cctggcccca      300
tcttcgtcag tacttggctg ggtcaccttg agaaagtcac tttccctctc ctgtcctctg      360
atttattatg agtcaaatac aggtagtacc tatcagggtt tcctgaagag gtacctatga      420
aaatgatttg tttccctgct gtaagtgata agaaaacctc caaagataat gccccctgt       480 cttttaagg cttctcattc tttcttatgg cactttctgc tcatgagtgg aaacttatgt       540
gtatttactg cagggacaac cacattttgt ccgcagagct atggggtgca gcaaaggaag      600
gtaggatttg gtacatttcc ccaactctct cctgaccaga tccatatatt ctcagctggt      660
tggaggcgtg actccaatct aactgaccca caaaacctct gcctctctcc cttctctgct      720
tgactcatcc attcttcaga acccagtttg ggagatctct tccagaaagg cttctgtgac      780
catcagtctg agtgtggggc ttctccttga gctcccacca agctctctct ctttttttt       840 tctttttcc acacaggatt gtgctctgtc actcaggctg gagtccagtg gtgcgatcat       900
agctcactgc agccttgatc tcctgggctg aagtgatctt tccacctcag cctcccaagc      960
agttgggacc acaggcatgc atcatcacgc ctggctaatt aaaaattttt ttttcagag      1020 aaggggtctt gctatgttgt ccaggctggt cttaaactcc tgggtcaag cgatcctccc      1080 gccttggcct ccctagtac tggggttaca ggcatgaggg actgagctgg caccacgct       1140 ctccttgtaa cttcttcctc tctccacaaa ggcagggact ttgattgtct aatgcctgat     1200
ctgctgccca gcaggaacgc tctcagtaaa agatgaatga atgaaaaatg ggtcagatgc     1260
acctgcaatg atgtgtgatt cattctcaaa gttgtgtggg tgtctggttg gactctgctc     1320
atgttcctcc tgtgtcccca ggtcccactt ctcactgatg cgcccaggcc agtctgtggt     1380
gctctactct ttctccaggg ccacctatca ctgaacctac aggatggccc tgatgaatca     1440
ggggcaggtg gcacaggtgg atggcagggg tacaatgtgc cagaagtgag gtgttcaccc     1500
cctgttcagg tggtttgggt tggagtctaa gctggtttcc tctattcctg tcttactcaa     1560
gggaaattcc taccctggc caagacagaa ataggagaaa ccagcttaaa atccatccct      1620
ttcctctgag acagaaaacc atcaaagtgt aacacattca ccttatctaa ggaaacctca     1680
aatttactca aaatggcaga gagagaaaaa tgcgtctctt gtgtgtgtgg agttggagcc     1740
acataatgca cattcagagg gtttacaccc ctcatggagg attcttctcc ttataaagtt     1800
gccacaaaag aagagacaca gccatggatg ctcacaacct aactaagatt aggataagcc     1860 tatgggcgg ggcggtgggg cagacagaca ggaatacaat gccttctgcc tctgcatgcc      1920
atttgtcttt cagggaaatc tggctgagaa ctgctgtaga tacttgctat cagcaagaca     1980
ctctcccatt tcctaccca gagttatgag gagtgtacgt gctgctggat gggagcagcg      2040
cctgggcaga ttccatagac agaaatgtga ttctgatgga aataaaacaa acaaacaaag     2100
caaactcagc aaaagtctca gcagtcatga accttctggg aaagagctgc actaaattac     2160
cgagtctctt catttagatg aaagtgcgtg tcttgagaca tcattgttat tttaaccatc     2220
tgggaggaaa gtattctccc taaagcctga gctccttgaa ggcagagctg tgtcttacat     2280
aactctacat catccatggc gcctggttgt agtagttgcc ttcccaatac ctcttctttt     2340
cttctttacc aacagaacct ctgtattgtt ggggtttgaa gtaataagct acatttccca     2400
ttcttcttgc acagagagat ggcaaatgag atgtaagcaa aattgattaa agcgctgtta     2460
gagctgtttg aaagggattg agaagaatgc cttttgctg tttcccttc ctcctgcctg       2520
```

```
ctgactggaa tttacatgtg atgacttgta tttcagcagc cattttgtga ttatgagttg    2580
actttgaaga tgaaagccac atgctataag aatggtgaag caaaaagata ggtttctaaa    2640
gcttctgaac agcaaaggaa acaatcaaat gtacccata aatatataca cctattatat     2700
gcccataata attaaaaaat taaaaagggg ctgggagcag tggctcagac ctataatccc    2760
agcactttgg gaggccaagg caggtggact gctgagctcg ggagtttgag atcagcctgg    2820
gcaacacggt gaaaccctgt ctctaaaaaa aaaaaaaaa aaaaaaatta gctgggagtg     2880
gtgtgtgcct gtgttcccag ctactcagga ggctgaggtg ggaggattgc ttgagcccag    2940
gaggttgagg ctgcagtgag ccatgataac gttactgcac tccagcctgg gcctgttatg    3000
caaaagtgca tgggctctgg gagagaggtt gggaggctcg cctttgaata tgggtattaa    3060
gcttcagtgg atgaattata tatcatttat taatatcttg gctgctcaga aaccttttta    3120
ctcacttgca gctttggcca catcttaaac agctgcatag ctagctctaa acaggtgaga    3180
attctgaaca ctacatctca aatttccttt tttttttttt ttgagacaga ttcagattct    3240
tgctctgtca cccaggctgg ggtgcagtgg cacggtcttg gctccctgca acctccgcct    3300
cccgggttca gcgattctc ctgcctcagc ctcccagta gctaggatta caggcgcatg      3360
ccaccacgct cggctacttt tggtattttt agcagagacg tgtttcact atgttggcca     3420 ggctggtctg gaactcctgg ccttgtgatc tgcccacctc ggcctcccaa agtgctggga    3480
ttacaggtgt gacccaccac gcccagccac atttcaaatt tctaagagct caggcacagg    3540
gaggtgagca tgacatcagg taagggaagt aagggttcgg tctgtcgttc ctgctggaca    3600
ctgaaggtgg acgtgtattt gatgaccaga tagaagatgg gtccttgtgt agtcttttca    3660
cttcagagga gttcctttgc tctcttgggg cttcgggttc cctttccatc cagatgccca    3720
gatgctccta gactggttct tccctttctt ccctggcttt ctgttttctg tgcttgctca    3780
ggggaatagt gtgggaagac agtttccctc acaggttcaa ggcggtagag cgttgttgag    3840
ggtctcctgc tggagaagtg gaactttgcg actgtcactc aggagtgcaa tgcagtttct    3900
gagatgaaaa tttgcgaacc aatttcacgt ggtcaatgtt gtgaatgaat ttatagctag    3960
tgaggctctg agtgctgatc agctgggatg actttggagc tagatctgaa tactaatggg    4020
actgggtgac tttagttggt gagaattttg agaccctctt tgttttgttt aaaatggtct    4080
gaggcttttt tttttttttt tttttttttg agatggagtc ttgctctgtc gcccaggcta    4140
gagtcagtgg tgtgatctcg gcttaccgca acctccgcct cccaggttca gcgattctc     4200 ctgcctcagc ctgctgagta gctgggacta caggcgcctg ccaccacgcc caggcaattt    4260
ttggattttt agcagagacg tgtttcacc atgatggcca ggctggtctg gaactcctga     4320
ccttgtgatc tgcccacctc ggcctcccaa agtgctgaga ttacagccat gtgccaccac    4380
acccaggcgt attatatcaa taacaatttc ttagttttga caaatgtacc atgattgtgt    4440
aagatgttac tagtaggcaa tgctggataa agggtataca agaatcatat atgccatctt    4500
tgtaactctt ctgtaaatct aaaattattc caaaattaaa agtttaaaat aattttttaaa   4560 aagtcaatca ccaaaaagta agtacattta ggacatagat acatgcaaga catgtgtaac    4620
ataactgaaa atcacagatt ttggagtcgg acgtacctgg tttctcatcc tggctgcccc    4680
aattgctaac tgcaatgttg ggcaaatttc tttattcctt caagctctgt gttccaatct    4740
ctaaaatagg aatcctaatt atatatactt caaggggttc ctgggaagag taaatgagaa    4800
aatactggca aagtgcctta tcatagtgcc tgattgcctg atacatagta agagctcaat    4860
aaaagtagct tttattattc ttgcaggtga tcaaagaaat gcagagtcaa acaatgttgg    4920
```

-continued

```
caaatgattt cacacctact gaatcggcaa caactgtgat ccccagtgcc tgacagagtg      4980
tgctgaaacc ggtacattca taaactgtaa accagtacag ctatttggaa aagcaacgta      5040
gcaatataga cacagcaaga gactgcagaa atggtcacaa cctttcgccc agacctcctc      5100
ttaatgattt gcagggttcc aggcaagggt ataaatggag cctcacatac catatgtata      5160
agtagtttaa agttagaaat caggttacaa actgttaaat gaaatatgt tctagcctcc       5220 tgccttggca aatatactgt caccaccacc tggaagggct caagttaaaa attctcagat      5280
gcctctgcat cctgtgttgg aacatgacgg catggggaga gccagttgct agcccccaga      5340
cccactgtct ttccaattcc taagtctgtc cagcactgag ggggcctcat gtgaatgtga      5400
gtggacagcc tagcccatgc gtccaaactc tgttcactac ccctgcctg tggccactcc       5460 tcagatccgg gtgtgtctac tggtggtgtg attggatctc aggaggagag actcaggac      5520 cagggctggg caggccctgg agatgagcat ggggccagtg ggcagggact tctgggagtc     5580
ctaggcacct ggagaatggt ctaaaaggga ggacgtggat ttgcaatggg catgttccct     5640
tggcctgcag actcctcacc aggtgggagg gacgcagccc aaggagggcc aggggacac      5700 cccctgcctg atctcactgc agtactcctt agagtccatc caaaggaaag aaatagttca    5760
gcagaataaa aaggctacgg gcacaaagat agtatcactg tgttgcattt gacactaaaa    5820
aaacccaatc taatgttcaa cagtagggaa atgttaagac aacaatgata aagctattca    5880
gagaagtagt atgctaccac caacactggc acatgtgaca accatgtcat aacatgggat    5940
aatgtttatg tgtagatata atagtaaatg aactctggca actgtgcaaa catctgtgcg    6000
ccctaggtga gatgcggaag tcaacctgca gacatgagaa cagctgcctc aaagagggtt    6060
gaactctttc aggcagctga agattttcc tcccaaaatt gtctctttcc tgtggctggg     6120
gagaagcagg gacttttcag gaactaatgg gtaagagctg gctggttaga ctggagtttt    6180
ttgtgcaact ctactcagga gttggagata agaacctgct acctgctgca tggaagccag    6240
aaaagcactt tagctaatca cactccctct ctgcgtgggc tgaagatatc cttgagtcct    6300
cccagccctg agcccttctc caggggccag cacacccaga aaccacgcgt gcagtgtttg    6360
ctctggatgc ccaggatagt ctctgctgcg cgtgtgaagc tctgccatgg gctgggtatg    6420
gaacgggcca tgtcacactg agtcctcgca acaacctggt gagatgggag cctcagcatg    6480
gctgacttgg acactgagat gctggtccag caccacgcag ttggcaagca gagaagccag    6540
cctttgaaac tctgtgcttc catttgggca cgtacactgg gaaatcaaaa ggcagtgttc    6600
cctttctccc cacaaactgc ttctagtgtc ccatggggcc agaggaactc aatcaaaaca    6660
atattccata gatgtgggat agtggtagca caaataaatt aacaattgca cttctgggca    6720
ctcgactgtc cccacggttc taaaaatgaa aagactctgg tatttaattt atattttata    6780
agagtgaaaa aggccaggca cagtagctca ccctttaat cccatcattt tggaaggcca      6840
aggtgggagg attgcttgaa ctcaagagtt caagaccagc ctgggcaata tggcaaaact    6900
ctacaaaaaa attagccggg tgtggtggtg catgcctata gttccagcta ctcagagact    6960
gaggtgggag gatcacttga gcctgggagg tcgagactgc agtgcgccaa gatagccacca    7020 ctgtacttca gcctgggaaa cagtgagatt ctgtctcaaa aaaaaaaaaa aaaaaaaaaa    7080
aatttgataa ttgcctttgg taaggaagag ctgattttag catggaacag agggtggcaa    7140
acaacagcct tcaagccaaa tctattccac tgcttgtttt tatatgtccc atgatctaaa    7200
taatgggttt tacatttta aatggttggt gggggaaat gtgaaactta catgaaattc        7260
```

-continued

```
cagtctccag atctataaat aaagttttat tggaacacag ccacattcag ttgtgcatat    7320
gtattgtcta cggcagcttc tgcactatac cagcagagtt gaggagttgt aacagggaga    7380
tcatatggcc tgaaaagctg aaaaatttta ctatctggtc ttttacagaa agactttgct    7440
gacccctgaa atggaagaag actacaggcc tagttattta gtgataattg aacccagctt    7500
tcattgtttg agtagcttct gcatgtcgat tgttaagctt tacttaccta gattacttca    7560
aatcctacaa agtacatatt atcgatcccc tgagcaaagc taggatatta gctgaagcct    7620
taaattcaaa ttcttacttt ttaaatttaa tttaatttaa ttaaaatttt ttttttagag    7680
acagggtctc gagctctgtt gcccaggctg gagtcagtgg catgatcata gctcactgca    7740
gcctcaaatt cctgggctca tgtgatcctc ctgccttggc ctcccgaagc actgggatta    7800
cagtgcctgg tctcaaattc ttacttccat accatggcag aggagcagag caagacctct    7860
tcagaaacat gagctctaac caaggcaggg aaaatatatt tagaggtcct gaatactgaa    7920
aacattacag tgtaccttcc ccagccaccc ctctgtataa tccaaaatat taaacattgt    7980
tgaactcaaa actgagtgaa agcaagtcca acagagttct aattccctcc atgataacta    8040
catgttttc taaaatagta tccgactatt ttatgagaat ttttggtgt ccctaggtat     8100
atacttgctt catttgttgg gtgattaaac cccaaaactg accaaaatct gttggccttg    8160
ctaagtctga gctcagggca cagaagaaga gtctcacatt gtgacagcca cctggcgtgg    8220
cgatagagtc ctgttctttc caccaagaga gaagccgtcc ctagagaagt ctctcattta    8280
agaaagcaga acatatctac tcaaaaagcc atggggccac ctgaatcaaa tgcctgtcag    8340
accttctccc tcacctcagg tctgtgtctc cctaagccca tgtcatgatc agagatgttc    8400
cttaaagctg ggctccccag cccccaggcc atgcaccagt acaggtctgt ggcctgttac    8460
gaacaggagg tgagtggcag gtaagcaagc attactgatg gtaatggcag gtcatctgga    8520
gtgtctgctg ccatcatact ggctgcagca ggaatgcgca agtggggctg tgtgctccat    8580
gaagccagcg ggaaccaggg acaagtggga gctccacctc ttccgagttg gggctggagc    8640
tccctgggtg ccacttcagc tgcccaaatg gcagctgcag acccaggcct cttgcagatg    8700
ggagccccgc cctcccaggc atagcaggca gacaagttcc tgggcagaag gaggtgggtc    8760
ctggtgaggc cccaccttca ggccagggag ggtctgaagt ctgtgggccc agctgccagt    8820
ctggtgaacc agagtgggga cttgtgctgc cttttttggg ctcatccatg ccactcatt    8880
ggaccaatca gtacatactt cctcccctct gaggcccata aaagccctgg gctcagccag    8940
agcagaggaa aggacggaga gacactggga tagccagctg cagagagaag ataacctctc    9000
atcagggaac tacagaggac aggacaacca gcctgcagag aggagctacc ctctctgcta    9060
ggagctaaac acttgtcagg acaccctagc tacagaggag ctgcccactg caagtcttct    9120
ttgagctgtt ctattgctca gtaaagctcc tcttcatctt gctcaccctc cacttgtcca    9180
cataccttat tcttccatgt tgcaggacaa gaactcggga cccactgaat ggtgaggcta    9240
aaagagctgc tgtaacacaa acagggctga acatgcccc ttgcttgcca cattgtgggt     9300
gaagagaagg agagaagagc tgcagccctt cagggatccc agacctggga gctccctgag    9360
ccagagccgt gactccctct ttggggttct gtggttcctg gcatctgcaa gcttctgggt    9420
gccactgcat tccccagtgc cagccaggga agtggcttgc agtgcacctg gtccagccac    9480
aaccttgcag agagcgctgc tggcacctgt agctgcctgc cccacagcag ccaccagtat    9540
gtctgactga gcagtggccg gaccccatgc tcgctcacac acccctcact gttccacacc    9600
cgactcaccc ttggcaggcg tgggacccag gccagcagtg tgaactgagt acagcctgcc    9660
```

```
aggcccagca ggcctgagca aaacttgggt aaaaacatca ctggccacag aggtttctgg    9720
ctaggaaaac aacaccccaa ggatcctgta acattcatcg gaacgccacc tcccgttaga    9780
tcagcggtgg catgagattg tcataggagc acaagcccta ttgtgaactg tgcgtctaag    9840
ggatctaggt tgtgtgttcc ttataagaat ctaagatcgc tgagattgat gagatcactt    9900
gagcccagga gtttgagacc agccttggta cacggtgaa accccatctt taccacaaaa     9960
acaaaaatta gctggatgtg gtggcgtgtg cctgcagtcc cagctacagg gactgaggtg   10020
ggaggatcac ttgagcccag ggaggttgag gctgcagtga gctgagattg caccactgca   10080
ctccagcctg ggtggcagag taagacctta tctcaaaaaa caaaaccaaa atggtttatt   10140
gtaaaaaaaa tgagtatggt caatattttt ttctcctcag ttctacttta atttcaagca   10200
ctcaagtgag gatcaagcat ctgatgagaa tgggagagaa aggcagagag agctgtgtct   10260
gttcaggaaa ccgcatcctt tcacaattag ggaaacaaca atttttttt gaggcagggt     10320 cttgctctgt tgcccagggt gaagggcagt ggcacaaatc atagctcact gcagcctcga   10380
cctcccgggt tcaagcaatc cccttacctc agtctctcaa gtagctggga ctacacacat   10440
gcaccatcac gtctggctaa tttattttca tttttaattt tttagtagaa acagggtctc   10500
tccagaaaaa ctacagatgg atcagacaat taaatactga accctgtgga acaaatagaa   10560
gagaaagtga aggcttgtct atccctagac acactctttc tggaacatcc gtcttcctca   10620
cactgtcccc tcttgacttc catgataccc taggctgctg gttttctcc tacctctctg     10680 gccagtcttt ctcagtcttc ttggccggct ccccctgttt ctgagcccca atccctatat   10740
gttggagtcc ttttgggtct caattttttt ttactccttc tcttttaggg ttttcttcct   10800
atgagatctt tcagtctcta gcctttaatg ccactgagtg ttgccatttc tactcccatg   10860
ttcataattc cagccctgat gtctggcctg acacttagag actgtccacg gagggataca   10920
ggaacaaagg aagtgacagg agtgacaaag gaaaagatgc gtttgtgtgt ttctgcacgt   10980
ttctgtgtct gtttgtctgt gtctctgtag gttctgcatg tccaaaaaag aatacagacg   11040
aagaggccaa caacaagggt ggacatattg cagcaaacat gaaaaacaaa gaattgctac   11100
cttatacata aaatgttcat aatattagaa aacaaacaca ttaaggctcc aagaataaaa   11160
caggcaagaa gcagggtcag aaagttctca gaagagaaga tacatttagt atacaagcat   11220
agaaaacgtc cagtcttaga acttatatca atgcaaatga aagcaagtag atacatagtt   11280
atataagaag aacaaaggtt gagaggttgt gaatgctgtt gttgttgaag cgagtgaaac   11340
aggtgctctc ccatagcccg caaactcgta tagtcctgtt ggaaagcatt ttgctgcatt   11400
tgacccagta attatacttg tggcataaat cctaaagaaa tcattccata agctaaaaag   11460 caaacttta agaagcatct atacagaagt agattaagta agccttgata aatcactaga    11520
ttttggaata tctcagattt tcctgacaat gggaatcacc caaagtactt accatgtatg   11580
caagttcctc tccctgggaa attctgattc tgtacctctg ggatggtgcc caggaatcta   11640
tattttaaaa aggcacttta ggctattctt atcttcagac acatttggaa aatactgata   11700
gaggaaatat aatgaaatgc catcatgagg tcattaaagc taatgtgtgc aaagatcgta   11760
taattctttt tttttttttt tttttttca gacaaagtct cactgttgtc ccccaggctg   11820
gagtgcaatg gcacgatctc tgctcactgc aacttccacc ttccgggttc aagcaatttt   11880
cctgcctcag ccttcccagt agctgggatt acaggtgccc gctgccatgc caggctactt   11940
tttgtatttt aagtagagac agggtttcac catgttggcc aggctggtgt cgaactcctg   12000
```

```
acctcaggtg atccgcccgc cttggcctcc caaagtgctg ggattacagg cgtgagcaac    12060
catgcctggc tgcaaagatc atataattct atggaaaaat acttaatgac attttgagtt    12120
cctagaatgt caaatgaaat agcagaatat aaaagtctgt gaagtattgg tctattcaac    12180
aaataaatat ttactgagca cctactaagg gccagccagg tcgtggggag acagaagaga    12240
acaaaacagc tgccatttat cctcatggag cttcgagtct aatgggaaga taaagagtaa    12300
agttaagaaa acacacacac acacacacac acacacacac acaaaattcc atacttacct    12360
aactgcatgg ccatgatctc tttacaaaca cattgtctcc ttccatgggc ggagagctgc    12420
tgcagaacca actgcttttg gtgggattct agctccatta cttagcaagt gcttgcaact    12480
ctgtagcagc ttaggaaaga actgtggttg aaggaaaga gtgtggtgca tggatttggt    12540
aaaagagtaa aaagagtggc tgggcacggt ggctcatgcc tgtaatccca gcactttggg    12600
aggccgaggc gggcagatca cgaggtcagc agtttgagac cagcctaacc aacatggtga    12660
aaccccgtct cttctaaaaa tacaaaaatt agccaggcat ggtggcacac gcctgtagtc    12720
ccagctactt gggaggctga ggcgggagaa ttgcttgaac ctgggaggtg aaggttgcag    12780
tgagcagaga ttgcaccact gcattccagc ctgggcgaca gagtgagact ccatctagaa    12840
aaaataaaaa taataaaaga aaaagtaag aagagtagga gcagaaagaa agtgagttaa    12900
taaatgacca gggctgtttc tgaattctgt atggtgggc agaaaagatt ttctttaagt    12960
agacttctgg gtacctgtag acagacgtgc tgaaaaccca ctggcagaac agcagccctg    13020
gtctggaggg accatgttgg tctccagaag ctaataccac aggtcagagt tcagatcacc    13080 cacccccaaat ctgggatctg ggatcagtat gagtctagga ctggggcaaa agcccggggt    13140
ggggatagag ggctgtgtga attgacctgc cattcagaaa cagcctcaag tttaggcttg    13200
gagttatctc caaatgagat tatgaatact gtcacagaga gccacccgta agatcgaaaa    13260 aaaaaaaat taaccaggac ttttacactt gtgtgttatg actgagctgt attgactctg    13320
atgcagtctg aatatttaa aaataaatca tacgcttatc tgggaaccaa aaaaatatgt    13380
tgcattatag ttggttgaag taaatatta atatcctgga tatgatagtt tttataattc    13440
tgggttggca tttcttcctt gtatcaaaaa ctatactaag gccagttgca gtggcttgtg    13500
cctgtaatcc cagcactttg ggagcctgag gtgggcggat cacctaaggt caggagttca    13560
agacaagcct ggccaacatg gtgaaacccc gactccacta aaagtacaaa attagccagg    13620
catggtcgcg tatacctgta atcccagcta cacgggaggc tgaagcagga gaatcgcttg    13680
aacctgggag gcggaggttg cagtgagcgg agatcatgtc attgcactcc agcctgggca    13740
aaaagagcga aactccgtct caaaaaacaa acaagtaact atattagaat cctcaaacgc    13800
tggaagtggt ttaagcctgc cctgactctg agaggctatt ccagggtaag aatgctgccc    13860
agtactctca aaccctgtag aaaaggggct ggtgcttatt tccttagagg catttctgtg    13920
tagtttatct ttggtgctaa tgcggtcctt ttcaacttac cgtgttaaac aggacattag    13980
ggttctgtta agaagagatg cactttggga ggccgaggcg gcggatcac ggggtcagga    14040 gattgagacc atggtgaaac cccgtctcta ctaaaaaaaa atacaaaaaa attggtcggg    14100
catggtggcg ggtgcctgta gtcccagcta ctccggaggc tgagacagga gaatggcgtg    14160
aacccaggag gcggagcttg cagtgagccg atatcacgcc actgcactcc agcctgggca    14220
acagagcaaa aaaaaaaaaa aaaaaaaaaa aaagatgtc gctgagtgag ggagaacctc    14280
tcctgggata tgtcctacca ggaagcatat ctgcaggatc agattacaca gattacagga    14340
ggtaacagag ctggggactt agaaacagca gctgtctagt ttcctattta tttactcatt    14400
```

```
ctgagcactg tccattggaa ttttttagg aaggcaggtt tggtgtgggc taggtagttg     14460
agatcctgag acctgctggt cttgatctgt agggagctga ctggatgacc ttggcccag     14520 gcctgccata gatgtaacag ggaagatgca cttggccatc tccaagggcc actgcagccc    14580
agaacattct acgttaataa gactcaagag tgtttgccca atggcaaaaa caaagtcac     14640 accttccaac tcagaccatc caaacggttt atgaacttcc aagttttatt tgttgaatcc    14700
cacaggtcta tcatcattgt aaactcttat tcccccagt aatatatctg taataatcct     14760
gaagcatgaa tatcttgaaa atagctgcag atgcctatat tttcccagca gagccgataa    14820
aagagacttt tgtttacata ttcatcattc agagtgcttt gagaaattag gaagtaaatc    14880
gagttgcaat tctgcaagtg acttggccct taggactgtc ttacagtgtg tggtgtgtac    14940
cttgtgccta ttcaggacca ttcctatcaa aatgaatttg taatacaaac atgtcttcag    15000
ccaatgggac cacagaatct caccttgtca taagagatgc aatcagaagt attgtgcaaa    15060
cacctttccc tgacagaata agttcctggc aacccagtag cccctgcat aatcaaacag     15120 taagccagat cctaaatgtt ctatataaat gtagaatatg gaaactgtag tcaaacaaaa    15180
atagcaatag tggggtagaa accaggactc tgtacttctg tatttcagtc cttgtgtcct    15240
tcagtccttc tcaggccacg tttagtttgt tttaacaacc tcagcctaga actgcccttta  15300 attctggcaa caagggccct cctctggccc catgctttca aggatctgct ctcctgcagg    15360
tgtggctcct ttcttagggg gaaatgccgg gctaaggaat gtatccctca aggcctgggc   15420
ctccctattt tagaacattc tctggatacc caggattccc cgctcaaatg ttctgggcct    15480
atttctagga cctgcccagg ttctttgctt ggtccatcct cctgagggca gactatactg    15540
aagccttagg ctaaagaagg ggcagctttt ttgtggggag acggccagca gaacttggac    15600
ctgtgggccg agatgtgcac ccaggtgcat gtgaggactt tctcagtgca agatggagct    15660
ggagggagtg ggatgggaaa ggaggtggta tcatgtgctg gcagctggct ctccccatgc    15720
caacgtgttc cgggaaaaaa ttccaaggag cctgagaact cttaacttgg atctagtctt    15780
ctaggtcata aatgaaggtg tgcatatata tcaaggtaga aggatatgtt atcttttaaaa   15840 gtttttgttag tttcagccag gcatggtggc tcacgcctgt aattccagca cttcgggagg    15900
ccaaggtggg cagattacct gaggtcagga gttcgagacc agcctggcca aaatggtaaa    15960
accccatctc tactaaaaaa aaatacaaaa taattagctg ggtgtggtga cgggcacctg     16020
taattccagc tacttgggag gctgaggcag gagaatctct tgagcccggg aggcagaggt    16080
tgcagtgagc tgagatcacg tcactgcact ccagcctggg tgatagagca agactccatt    16140
tcaaaaaaaa aaaaaaggt tgttagttt gattggtaat gtttaaatat ttagacatgg      16200
agtaggtggg tctcccactt gtgatcttgt tctgagtgaa aatgttaggg gctgagctgc    16260
cttaagcaaa tctcttcacc tctgaggctt ggagctcctc tgtaccagga agccttgggc    16320
tccttgaggg ctactggccg gtccagctct ttctttcttt gaatgttggc tgatgaggct    16380
gaaactgatg aagaaaaatg taggcaactt cttttccatgg ctgctttagg tgggattctt   16440
ttcagtgcaa gggacaacaa tctaactcaa atcaccttaa gcaaaagaga gattcttttct   16500 gttcacttgc ttcagacatg ttcatattta gttactcaaa caccatgttg tccataattt    16560 attcctatttt cttcttctgt tttcgttttt tgagatggag tcttgctctg tcacccaggc   16620
tggagtgcag tggcaggatc tcggctcaga gcaacctctg cctccagggt tcaagcaatt    16680
ctcctgcctc agcctcctcc tgagtagctg ggactacagg catgcaccac caagcccagc    16740
```

```
taattttttgt atcttcagta gagatagggt ttcaccatgt tggctaggct ggtcttgaac   16800
tcctaacctc aagggatcca cccacctcag cctcccaaag tgctgtgatt acaggcgtga   16860
gccaccatgc ccggcccta tttcttgact cagcttttt tctctattgg cttcattttg    16920
gggcaagcca agatggccac aagcacctcc aagcttgaat ttggcaactt cagcaaaaga   16980
gaacattcct ttcctaatag gttcagcaaa atcctaact aagcctctca ttggccctgg    17040
ctgggttaca tgctcatcct ctaaacaaat cactgtgact caactgccag gaagctgggg   17100
gagtggaaga cggcggactc gcctgaacca cagggcagtg tggggcaaag ggtatttcca   17160
acaggaaaag aggggttctg atgctggaag aaggatgcta tgtaggcaaa atcaacagat   17220
gtttcaccag caatgcttac cacatgaact atgaggacaa aggaaacaga aacatacaaa   17280
tatttatgaa agacagcgat gaaatggtgc ggtggaaaat tgtgctagag aagccaatcc   17340 tgcccctca acgcagccac actgagcgag ctgtgggtca ggggtaccca ccctaccctc    17400
tccttggctc caaagcagat gttcactaca gtcaacttag acattgtgac tcagagactg   17460
caagttctgt cagacacttg gactgaggat ctacatggaa ataagcagag aaaggtggtc   17520
tgtgagagaa taaagcggaa atgcaaagaa caccagagac caggcagccc cagatagacc   17580
aagagctatg actccttccc tccagccagt ggctccagtg ccttgcaagg ctcagctgta   17640
tttcctgccc ttggtagaga ctcctgggtc cctccaacat gttttcgcgc gcgtgtgtgt   17700
gtgtgtgtgt gtgtgtgtgt gttacagctg gatttaacag tttgctgttc cacaaaccac   17760
aaataaaaca aaacacaata aaaacataaa ggtggggaaa tgctgttttt tcttctaaca   17820
tgtaagaatt gagtcaggtg tttctcaaga ctgttgtgat ttttatctta gtttttcaca   17880
aacatccaga gaagggatag ggaagcgtgc acgtggaacg acaaggcggc tgagttcaag   17940
gtctggagca agaagctctg catccctgca gctctgatgg ggacggagac cctctgggca   18000
gagatatgca gggaaatgct cattactctg tacccctac cccaacaccg cttttgccaa    18060
gaggtggact gtgctagcac caatgtggag agttttggac atccacgcca tatctgtagc   18120
agctgcggct atctcaatgc ataagctaca ttctcaaaga atttcacgtc aaaccagtgt   18180
ttataaacgg agcccgattt tcagtgcttg gagagaacct acacgcttcc gttaaaatct   18240
ctcttctaga aaagtgaaac acaacctgtt aatcagcatt tatataaggc aatatttaa    18300 aaatcagaaa aaagcttttt ttaaaaagg caaagttgac aagacaaata agctggatga   18360
atcaaatttc tgctttgttc tgctttcact aattgctgac agagccgagt tgcggcctga   18420
ttataaagct gtgcttcagc caccttagca aatctgttgc tggaagacaa ggagcgagca   18480
cttacttttt gagagtaaac tgtatttat tttttattat actttaagtt ttagggtaca    18540
tgtgcacaac gtgcaggtta gttacatatg tatacgtgtg ccattttaaa agcaccgggg   18600
gactggtcta tttaaaagaa caatggggtg agtggcgctc taatgacgga ctccagcttg   18660
ggggctttga ctatcctagt tcttcttggg cccctttgg ctgagcgtga agcaaataaa    18720
caaacacccc gatggagagg tccttaacca cggtgtgcag cagcatcacc tggggagctg   18780
tagcccagta cacacgccca gccccaccca ccagccttac tgagagggga agggatcctg   18840
cctgtgtgag ctgaaaagc tctccagtg attccgcttc aagcttccgg ttaagcacga     18900
aggctaatga gccttattta aaagctcagg ttttttactca gcaaaatctg ttgctttaa    18960 aatggaccgc ctttagaaaa accagcaatg ttgcatgcca ggatgggact ctctcccgg    19020 aaaatgaaata agcaacccct gagaaacggc gctgggacaa tagggcagca gtttctcctc   19080
acgtcctagg agggaaagtc gactgcaggg agttatatga cttaatatgc agctaaccag   19140
```

```
ccttttaatt aacttgacat gccagataac aaagctatta ctaagtgaga gtttcttaat    19200
tgaaaggggg aagagagatt tgttttatat tttcaaaata atctataatg agcgttacta    19260
atttgacaat cagaatttgt gtgtgtgtga aaaatagcta ttttgagcta tgaaaaggga    19320
ggatgagcag acctgcacac ggcagcttag cttgctgtgg ttttgcctta gctggtagac    19380
ggtgcctggt agtgcatgac tgaaagatgg tgtggttgat tctattagtg tgcaattgtt    19440
cgcaggcatt ttacctagaa atcacttgtg ccatcgtggc catagtattt ttccagcctc    19500
atctcttact gaactgtacc tctagctctg agtccagtca caatgaacta atttgtagtc    19560
tctcagtcat ccatgctttg cacatgcagt ttcctctcta tggaatatga aatacctccc    19620
cttccctcct cttccttccc ttcagcttcc agactcctgc cagcaagctt ataagtcacc    19680
tttcaaatct cagttcaaaa gcctcctctg agaccatctc tccacttgca agactcgggg    19740
gctccatcta tctcctggga tccctcgacc aggcactcta gactgtcatt atagcaactc    19800
attgagtgta ttacgatggt gtgcttttgt gcctgtctcc ccaccattca tatagtcaac    19860
acgcacttgg tagatgtcat catttgatca ctgcagcaat cctacagggt acctttctact   19920 gtgactccca tttcccagtg gaagaaactg aggctcaaac atagtagcct gcccagctct    19980
cactacaagt agatggttta cgtgtgatac aatccaggtt catcttgctt ctgagtttgt    20040
gctcttaact gccatgtgag caaacttcaa tcagaaagtg tttttctttt ttctttttct    20100
tttttttttt ttttttttgt gacagagttg ctctgttgcc caggctggag tgcaatggca    20160
caatctctgc tcactgcacc tccacctccc aggttcaaac gattctcctg cctcagcctc    20220
ccgagtagct gggactacag gcgcccacca ccacacccag ctaatttttg tatttttagt    20280
agaggtgggg tttcaccatg ttggccaggc tggtctcgaa ctcttgacct caaatgatcc    20340
accttggcct cccaaagtgc tggaattaca ggcgtgagcc accgcaccct gcctgagaga    20400 gactgtctit tcgaatttgt atcttcaatg cccagcctac aggagatgct cagtggataa    20460
tgatggataa ttatttagca gttatccatt gccaaaagaa tggataacat cactgctacc    20520
ggctttggca gacctcactc caggtaaatc attccctggg ggcattaatt acctgctggt    20580
gttccctggt taaacacct gtgacaccag cctacacata cgcacagggc tctgaggtga    20640
tttttttttt aatgcaaata aagacataaa aagatataag gtaaacctac gtgggctgct    20700
tatagcactg tcagttatgt gtgtgttttc atttacttca aaaactgagg atattaaaat    20760
aaatatgact ttattccatt tagttgagat tgtcattttt ttttaatttg gaagagaatt    20820
taagaaatga tgactttatt aacaacattg gcgtaggaca gtagcagact gggttaaaat    20880
actgtatcaa tgttgaattt actaaagttc atcactgtag tacagttttg gaagagaata    20940
tctccattct cagaaaatgc acactgaaga atttagggggt aaagggctat aatgcacaca    21000
actgactcgg atgtctcaga aaataagtgt gtgtgcatgt gtgtggtttg tatgtacgtc    21060
tgtgtatgag gaagtgaaag ggactaatgt taacaataga tgaatctgtg tgaaaaataa    21120
atgcatattc tggctgggca cagtagctca cacctgtaat cccagcactt tgggaggttg    21180
aggcaggcgg atcacttgag gtcaggcgtt tgggaccagc ctggccaaca cagtgaaacc    21240
ctgtctctac taaaaaaaaa aaaaaaaggc tgggtgtggt gacatgcgcc tgtagtccca    21300
gctacttggg aggctgaggc aggagaatca cttgaaccca ggaagtggag gttgcagtga    21360
gccgaggtcg ctccactgca ctccagcctg ggcaacagag aaagactcca cctcaaaaac    21420
aaaacgaaca aagaatggat gcgtattctt catattattc ttattttttgc aaattttctg    21480
```

```
caagtttgaa attatgtcca aacgaccttg gaagaaatga acatccctga gaggaaggtg    21540
taatgagagt gtttctttga aatacagtga gcaagagctg gcagggccgg tcagtgtctg    21600
acagtggcat gaggtttctt tcaggctgac ttgcaatggc tggttttctt tacctattga    21660
tgtgtcttga atatgtttac agttcagctg gcccagttct ctgagaggca attgggtttc    21720
cttgcagatg tgccgcggga aggacagtgg tgcctgtgct tggagaagcc cctggccacg    21780
tgctaggaca gagggacata tggtggcacg actccagcca cagatgcaac tccctcagga    21840 acagtgggc ctgcagttgg aagggcccc ctctggctca cagtgctgtg tggacagtag    21900
catctgtgtg actgcaaact cgcccactgt gagtgggaac agtcgaggct atctgtggcc    21960
ttgcatctgc tggtcccatt caccagggca acactgtgca tggccaattc tagacctccc    22020
ggacgcagtg catgcaactc agcgttagaa tgtcaatttc gaagtactag aatgtcattt    22080
tgctgttaca gtcaccccac aagcatttc tgagcatctt ctacttggga ttgcatcctt    22140
tttgctaggg actgtgtcat gtgcgtacac acagcatctt atttttagct ttcaggctga    22200
cttgattgaa catggtgcag ttaatgtgcc ccccattttc caaaagtaga aaactgtgac    22260
acagaggtta agtggtttct gaggtaacat agaaaaaata tgtagcagag atttcctaaa    22320
caaacttgca gcctggcagg aggggtaaga agatccacga ggaacattgg atcaggttgg    22380
aggaaagagg tgccaagaga gacccaagat cttggctggg aagtgaaaag gagtgtggcc    22440
acttttgatt ctggggtagg aggctttatt ggggaggtgg catttgcgtg gagactaaca    22500
ggatgataag aattttgaaa ggaaaatcat aaagagcttt ccaatggagt cgagaaaaca    22560
tggtaaaaaa acaaaatagg agttgagatc ataacaactg tcatttattg agttttcta    22620 tatgctagga actgtgagag gcgctttaga taaatcaact cattgaaaca ggagttttct    22680
taagtgagcc ctattagcat cctcatttta gggtaaatgg aggcatccat ggaaggttac    22740
atgcatctag tgtggtaaca aagcccacaa gcttagaaag tgcttcatga taatagtgaa    22800
atgatggtaa taataggaaa aaggaggggg aggaggaggg agaggggaag aggaagagga    22860
agaggagtgg ggaggaggag aggaaaagga gaaggagagg aggggagggg gaggaggaag    22920
aagcagcagg aggaagagtg gaaggagaag gggaagaaga aggaggggca aggggggagg    22980
aggatgagaa gaagggagag gagaaggagg gggaggagaa gggggaaggg ggagaaaaca    23040
agagggagga gggggaggag gagaaggagg gaggtaggag gaggagtggg ggacaaggag    23100
ggaaaggaga aggggaagag ggagaggatg aggaggggga ggtggaggaa tgaggaggga    23160
gaggaagaga gaggagagga aggagaaggg ggaagggaga gtagagaaag gaagaggagg    23220
gaggagaggg aagaggaggg aggagaggga agaggaggaa acgagaagag gggagaagag    23280
gagggaggag ttggggagga ggaagggag aaggagagg agaggaggga ggaggaatga    23340
aaataggcag ggggaggagg agaagaggga ggatgggaga agaggtagga gggggaggag    23400
agggtggagt ggggttaggg gttagtcctg gaggcatcag aggcttctct agggagcgtg    23460
gtttctatcc tactctacct tagccttgac caagcaggca gatagcatta gtattcactc    23520
cttgcttggg agcacttgaa aagtttataa aaaggcgtag gctgtttgga taaaagatgc    23580
tctggagaca agacagtgca tcttcctcag tcacttcctc actcctttct cggctctgat    23640
tctggtgttt gatgtcttcc cacaactcgg caaagaaaga agaaaatccc tctactcact    23700
gtgcagtttg taggttattt aaaggaaatg cattcaggtg gttccttacc cggcagggtg    23760
cagggatgga gtgggataca accatacaac caaccctca gagggcaagc gcagctcatt    23820
cacagtggcc aggatcccta gggcagcctc gggcgtctgt cccgcagcag aggacactct    23880
```

```
catgaggcgc tggaaactca gctcagggcg tgccaggtcc cacgggcgcc ttccagcctg    23940
ggacacctgt gccaaacctg aacagggaag gtgcagaaaa gcgtgtgtgt gcgcatgcac    24000
gtgtgtgtgc taaaatataa atgaacgatt aagggtttcc tctgctggat attctctgca    24060
gtggggagaa gaggtgggag aaagtagctg ttttgccgc ttggggaatg tttgcccaac     24120
tggtaaaggt agaattgttc ttttccaaag gaaagttgtg tgggagttgc ttccttaccg    24180
aaaacaagga aaagcattag tgaaaagatg taagatcaac aggcaatcaa aaatgcacac    24240
tgccagtgtt aagggcacag gtgaattttc cttctaggat tctcaataca aacctatttt    24300
gaaataaaat gcctctaggt cttccctgcc taaacccacg tggggagcac taatagctgc    24360
gtacaaactt cattaaactg gccacagctg aaggagctg gtgccaaccc actgctttt     24420 gctgaccgaa gtatccggct gggttttgc cctcattctg aagtgactgc tgcccatccc    24480
ccacaccttg agcattgttt tactagacat cttctagtgt agggtaactg gaagaaaagt   24540
aatggaatac caagtgccat tcatcatatc cctgcctctt ctattttgtg gtgcagggat   24600
gctgagggga aaatgagtct cctgtaagtg cttggagatc ctcccccact ccacctcctg   24660
catttccata agcatttggc atcagagtct tctggtaaac cccccagctt ctacaattgg   24720
acaattggct ttgtatcacg gcaggaattc gtgcctctga gtttctagg gaagctctac    24780 agaagcaata aagtggtaga gttgtttgaa taaaattagc ttctatgctt gtaggaagca   24840
tacccaattc cagttagctg tatgaaatgc aaccattttg gaggtttgtg aaaatatgca   24900
aggctcccgg cttcaggaga aaaacagatt tacattcctc cctgtctcag cagggagtct   24960
tcaatcaaag gcaaccaaca aatcaaacat gattatctgt cagcacattg gccctggttt   25020
gtaattatac atttatttgt gtgtgatcaa tgctagtctc ctcactggat tctaaactcc   25080
ctgagagctt ttctgtctta attaccctga actccagtgc ccacacagta cctggcacat   25140
agctcatgct gtaaatatct gtggaaagaa ggaagaaatg gagaaaagga agggaggaag   25200
gaacagaagg gagaaaggaa aacggaaaaa aagaaatgtt ccaggtggaa ggattttttt   25260 tttttttac aatcatcctg cccaacagta tataggtttg cctgtgatct ttttctcata    25320
cataagatgg agataatagt ccttgtctca atagttattt tacgttattt tctaactcaa   25380
atagttaaaa gtcatttgta ggcccctgct ctgggcccat gctttgtagg atctcactgt   25440
cgctgtcctc aggctgtgcc ccttcctaga gtatgaagtc ccggtgggac tttaagccta   25500 tgctccccett ccccttcctc cgcatctgtg gggacttctc cccgacagtt cacgcaggtc   25560
tccaccacaa gtgtgcatgc cctaggccca aggggtgtcc aaggagtgac tatttgtagg   25620
ggatgagcca tggatggaac tgtggtgtct gcacacatgt gcctaagacc ctctcccatt   25680
gtgggatgga gcctgcagtt cagtaggggg aatgaaggga ggtgtgaatc atggctcttg   25740
acccaggccc gcctctctct gtgtggccag ggttcagggc agaacctcag gaggctggaa   25800
gttgtagctt ctaacctggc ctttcaggtc atgatgaagg tctatttgtc agggtaagag   25860
gttcaaacct cctgcaatag tcctattcag cagctgatag cttggtttat aacttttgaa   25920
tatttagatg tattccacgt gggcaaatag gaacacacac acatatatat gtatatttgt   25980
gcatttatat gtgtgggcat gtgtgtgcac gtgtgtgtac atatataatt ctatagttca   26040
cctgttagtg taccttgatg atgaaaagtg agggaggacc ctgactttgg acagcatgga   26100
tctgcctgcc acttaccagc taaactgttt cctagggca aaaatagaga caacaatagt    26160
acctatttag ttggattatt gacattatta aaagagagca actaacatac tcctagaata   26220
```

```
taagtgctcc atgcatatta taaactaaca attgtttcct gctcctttca cttcatgcat   26280
gaagacatat tcactcactc ataaatactt gcattatatc tatctatcta tctatctatc   26340
tatctatcta tctatctatc atctatcaac aaagtcttgt tctgttgccc aggctagagt   26400
gcagtggtgt gatcctagct cactgtagcc tcgaactcct gtgctcaagc aattctccca   26460
cttcagcctc ctgagtagct gggactacag atgtgcacca ccatgcctgg ctaattttg    26520 catttatttg tagagatgag ctctcactat gtcgcccagg ctggtctcga actcctgggc   26580
tcaagtgatc cttctgcctc ggcctcccaa agtgctggga ttaggagtgt gagccaccat   26640
actcggccat tatgtatatt tcttattcaa tctgagaact aactataata ttattcattt   26700
actattttag ttcaagttga tttccttta aaacatacac accaagttta tgtgtattga     26760
taccagtggt ttcccaggtg ttttttgtt gttgttttgt tttttcagat tctcattctg     26820
ttgctggagt gcagtggcgc tatcttggct cactgcaacc tctgcctccc gggttcaagc   26880
gattctcctg cctcagcctc ccgagtagct gggactacag acacgtgcca ccacgcccag   26940 ctaattttg tatctgtagt agagatgggg tttcaccatg ttggccagga tggtctcgat    27000
ctcttgacct catgatccac ccgccttggc ctcccaaagt gctgggatta cagacgtgag   27060
ccaccatgcc tggccttata taggtatttc acaaaatgat ttcctctatt aggaccatat   27120
tcaaaaagcc cttcccctac tccacaatta cagaagcagt cacatacatt ccatttgatt   27180
cttctctatg atttcatttt tgaaacttaa ttccttaacc cacctggaat ttattgcggt   27240
gttgttgtga ggttaagaaa aaaaaaatc aatctaatat aatgtttcta aaaagccagt    27300
tgtctcggca tcattttggg aataatcttt cccctcatca ttcatttaca tttctacctt   27360
tgtcacatag ttaatacttt ttttcaattt gggtttcttt ctaaacctgt aagtcaattt   27420
taatgatcta gttaactttt gatgccagta tataccgttt taattcttgc aggtgcataa   27480
cagttaatac agcagagcgc aagggctgct tagttttctt gttttccct tttatttgg     27540 gtgggttggg aagggaaca aggtcttgct ctgttgccca ggctggagtg cagcagcgtg    27600
atcacagctc accacagcct caacctcttg ggctcaagcc atcttcccac ctcagcctcc   27660
tgagtagctg tgattacagg ggtgcgccac catgaccagc taattttttt ttttttttt    27720 tgtaaagaca gtggtcttgc tttgttgcct aggctggtct cgaactcctg ggctcaaacc   27780
cacctcagcc tcccagagtg ctagaattac aaacatgagc cactgtgcct ggccattttt   27840 cttcttttc aaagttgatc aattatgtga gcatcaccac tagaatctgc aaatgtctcc    27900
tgtatcggca acgagggagg taccataagc acccttcttt tacagatgag gaaactgagc   27960
acagaaagaa gagacacttg ctcaaggtca caaaaacaag gcaggtccag gaacagtgaa    28020
acacaggcag tctagctgca gggaccacga tcataacctc tgcaaagtgg ggcagatcca   28080
acctgagaat caatctcctt caagtcggag cattttctcc tcatatctat tattactgac   28140
ttcttagtat ttgttttatt tatttggttg tttaatgatt tcatatgttt ccctgtgttt   28200
cgttatatac tttctattta taatgcttct taaagttttc tggttacaga ctattttctt   28260
tctttttttc tgagatgtgg aacttaccat ggttcatatt ttaaactctt tggctaggtt   28320
tactaataat tgtgcttacc cgaaagcatt ctttaactgc tatttctttg gttttcaagg   28380
tcagtgactc tttatatggc tgcatacaca ttttagtaca atgataactg gataattta    28440 ataaagttgt ataagatata gtttacgaac ataaaaatga ttctattatt agctaaaatt   28500
tcagcagcac tgttgacata attttttattg tttttaattaa attgcatgga aaagaaataa  28560
ttttatcata agaataaaga ggatgatagt tcaaagttat ttgtgagaat atcgtggctg   28620
```

```
tattgcatta gcatcttgac ttttaaggtg atgtttaata gagacacaac aattctttag    28680
gtcgtaaagg caattcttgc tgttttaaaa aaatgttatg acaacaggtg tgatcacata    28740
aagtattagt aaagatgaaa caattttaaa tattttccac tctatattct actgctttat    28800
aagaaggctg acaagaaaac cctcatttca ctagatcata tctacatctc actggcagga    28860
aagaagggcc catatgagtt acttacctaa gtaggaacta ttattcctgt tttacagatg    28920
agaaaaccaa agctcagagg ctaagtgact agttgaatgt cagcagacca attgaagaaa    28980
actcaaaatg tcaccactca ccaaattcac ctgtctatcc agccagtgca cacatccttg    29040
gcagatgtct cctaattaag tggagtgtgt gtgtgtttgt gtgtgtgtgt gtgtgcgcgc    29100
gcgcgcgcgt gcgcgcgcag tgaggtgggc caccccgcct gcaggcagct ctaagtcata    29160
gttccgttaa ttatttattt tatatgatga ttttgagtcc ttttgtagtc ctggctgtct    29220
ttttatgagc acatttctat ttgagaaagt cagcaggaat ctggattctg gaatcactga    29280
attccaatgc tagctccaat tcttcctaga aacgtgatct tagaaacgtt aatttatata    29340
acagaaatga taatacatat cttacaggta tggtgtgaga gttaaatgag aagttgtcca    29400
tgtatttagc attgtgcctg actggtatca tgtgctaatg catactgctc attttatttt    29460
atttccatgg tatggacgtc cttttaagaa tattcgccca ctgtagctgg gcgcggtggc    29520
tcacgcctgt aatcccagca ctttgggagg ccgaggcagg cggatcacga ggtcaggaga    29580
tggagaccat cctggctaac acagtgaaac cccatctcta ctaaaaaaaa aaaattacaa    29640
aaacttagct gggcatggtg gcgggcacct gtagtcccag ctactcggga ggctgaggca    29700
ggagaatggc gtgaacccgg gaggcggagc ttgcagtgag acgagatcgc gccactgcac    29760
tccagcctgg gcgacagagg gagactgtct caaaaaaaaa aaaaaaaaaa aggatattcg    29820
cccagtggaa caactttggc tgctggtccc tcctctgtct cccccaagca gggttatata    29880
gttcgttgag acattccctt caccaaaagg cattcctcag ctcagggaaa ggaaagtgga    29940
gaggaatggt gagtgagacc gtctttaaat atcctgaact actgccccct tccttattgt    30000
ctactatcta catttgggga gtgattctct tagcaacctc tcaggtttga tatcagcaat    30060
actgactcat gatactaccc caaagccaaa gcatgaaaca tggaaggtgt tcactaggga    30120
caataccaga tttccttaaa tcacaaagca acagagcaca tcacactgga tgtctcactc    30180
tggcttcctg cccggctcca tatcaacggg caattgacgt tggggggagc catttcctac    30240
tctggccttc agcttgcggt cagctgagtg tgttggacca cacactctct agcatcctgc    30300
gattctaacc ttctatggat ttcatcagtt ttatagatat gagttcagcc tacgactttg    30360
ggaaacaaag gattcaactg taaaaaacat ttgaattcca ctgatctatt ttatctctgc    30420
tcaggaagaa aaaatggcac cttcttcctg aagtttgtgt ttccggtctc cttgattct    30480 gagagatttt aaaattactt tctattttc ttactctgtt ctgatattgc aaaatggtta    30540
ttaccaatta ttaactaagt gatgtttaat tttagaagtc aagctacttg taagggccca    30600
tataaatgtg tgctaggatt agctttagat ttgttttctg cttctattta cagcaaggac    30660
aggactgggg agtggtttta ttttattaag ctttttagca tgatttaatt tttaaaactc    30720
aggacgtatt actttaaaaa ttaatcgaat aaagatgtat gttcataact tgaaccacac    30780
agaaaagtaa aatacaaata aaattgtgat ctcattactt aaagaataac cattgttggc    30840
catgtgcggt ggctcacgcc tgtaatctca gcactttggg aggccaaggc gggcgcatca    30900
cttgaggtca ggagttcaag accagcctgg ccaacgtggt gcaacctcat ctctactaaa    30960
```

| | | | | | |
|---|---|---|---|---|---|
| atacaaaaaa | aattagctgg | gcatggtggc | gtgtgcctgc | aatcccagct | acttgggagg | 31020 |
| ctgagccagg | agaattgctt | aaacccggga | ggccgaggtt | gcagtgagca | gagattgcgc | 31080 |
| cactgcactc | cagcctgggc | gacagagcaa | gactccatca | caaggaaaag | aaaacaagca | 31140 |
| ttgttaaaat | tttgatgcaa | ttccttgtag | cctactcatt | cactgtttct | aatgcttact | 31200 |
| aagtgtttag | taacacatac | atacacactg | cacacacaca | cattgtctcc | ttcttcactc | 31260 |
| aacataagga | tagcatttcc | tatattatta | aatattttt | aaaaatgtgt | gtgtgttaca | 31320 |
| tgtgttatat | gtcacacaca | cttttaacca | cacaaagaca | caggagaaca | tcaaaaatca | 31380 |
| agatgctttc | acgtcccctc | acacatgtga | tccttataat | cctgtgtgag | aagcaggact | 31440 |
| ggaaatattt | ccaacttcca | gctgaaaatg | catagctcag | agacaggaag | gaacttaacg | 31500 |
| ttggttaaga | tcacaggctc | ggggtaccac | ataccagctg | tgtgaccctg | gcacaataa | 31560 |
| tggatctaag | atttgtgggg | cgcgaagcct | gtatcatttt | aggggttctc | cttaaagaaa | 31620 |
| ataataaaac | atttacctgt | gaaaatttta | gtgatttcat | gtgatcttgt | aagtatattg | 31680 |
| ctaggacctc | ttccagggcc | ttggaagggt | ctgtgttaag | tgaggagccc | tgtagcttca | 31740 |
| tttcatctgc | ttggaggcaa | atctgccttt | atttgggtaa | gtgacttatt | ttcatctgta | 31800 |
| aagtggggat | aataaaagtg | cttgcctctg | agtagttaga | aagattaaac | aagatactgt | 31860 |
| attgtaaagc | attttgtaaa | cttcctggca | cattggcaca | taataagtgc | ttaataaggg | 31920 |
| tcacctgtga | ttactaattt | tattcaaaat | catgtcattg | tggctggtgt | catttgagct | 31980 |
| gcttcccaga | gactgagcga | ttcctgtaca | tacctaaagt | tacaccttca | agatgctgca | 32040 |
| gcttggctca | ctcactcatt | taataagcat | ttaggagttc | ctgctagatg | ctatgcactg | 32100 |
| tgctaggctc | cagtctcaat | tcattctcac | accacattca | ctggaagcac | aactcaggta | 32160 |
| tccctcctc | tgggaagccc | ttctaggacc | ctaagccgac | tcactactat | ctgggcactt | 32220 |
| atctctctgt | gtgactgggt | ttggacatca | ctagtattca | aggaaaagac | attatcctgc | 32280 |
| ccctctgcca | cctttgttca | tttcagttca | gtataatcga | tacttctctc | tgtgcctata | 32340 |
| atacagtatg | gaggtgctca | ataatcttaa | atgagttgac | tgagcatgtg | tttgttttca | 32400 |
| caggaagatt | tccgtttctt | ttgcaagcta | tttaatttgc | aaaagtaagc | aagatgtgca | 32460 |
| caaaatagtt | ttgagacatc | tggaaacaaa | acaaggttgc | ctcatcatta | atcttgtttt | 32520 |
| tgtgtgataa | ctttactttt | tctcatttta | tgacaactga | aattctctat | tatactgcca | 32580 |
| gacctcattc | tgcaagcttc | tctcctgtgc | taataaaaaa | tattatggcc | acatcgagaa | 32640 |
| gtccttaggg | aatgtgttct | gcatcaggaa | aagtaattaa | gctctggggt | cctaaaggag | 32700 |
| cctgggaaag | tctatccaga | aactatgggg | ttaggatgta | ttatctattg | aaaaacagaa | 32760 |
| ccggactttg | caagttttac | aatatcttgg | cttattaaag | ccactaactg | agaattaaaa | 32820 |
| tttctggatt | gttacttta | caacagcagt | caagtgtcgg | aaaatatcct | gaccagtcag | 32880 |
| taaggtatac | aaatagagaa | ggcaaggagt | agctgtgagt | aaagcgccaa | ctacatttgc | 32940 |
| tgagtacctg | ggaatttacg | agttagcttt | tgctatcatt | atccgtctcg | ctaaagcaac | 33000 |
| cctatgaggt | aggtgggaag | ctggatgccg | tcctcttttg | acagccaaca | ctgaagaaca | 33060 |
| gctgggctg | gaaactagat | ctgtcagaca | tagtaactgc | ttctatcact | ctcaccaccc | 33120 |
| tcccatgctc | ttgagagtgc | cttcgctttt | gtgggtgtct | tcagaaaagc | atgcggatct | 33180 |
| ctgtataggt | tttactcaag | tgttcctctc | tgtggagggt | gacctgggct | acatgaacat | 33240 |
| gggcacctca | ggatcggcag | cttttccatga | attcctatgg | taaggggttc | agcttatcct | 33300 |
| tcatgtgggt | gaagatgtat | gatttcattg | aacattggca | gttacagcca | agtacaagtc | 33360 |

```
ctgccttcag gatccagcag ggaagaatga cattaaacat gtcaccttgg agaaatgttg    33420
cattcacctt ccgggtaatg acccagccac ccagggactc ctctgaaata tccaatcctc    33480
taagtttaaa cacgtttcag aattaatcca tctgaattct tatcgctgta gatgcaagga    33540
gaaggagtta tggcaggtct gaaactatta gcggccaagc tccctagcag aagcaacctc    33600
tccctacacc ccattatccg tgcacagctc cttatcagcg gaggaacaac tttactgtca    33660
ccatattttc tacttggaaa aaaaaagaa acctcagcag gcccaatccg aaggctatga    33720
aatttcaaag aaacagagct aagaggcgag aaactagccc tttgtgttaa aaagatggaa    33780
atgctccaag cgcctttcca gtctgctttc tgtttacagg ccttgcgtga gcgcgggagg    33840
ctgggcctca tctctggctc tccccagcca ggacccctta ctcaaaaccc tccatctcgg    33900
caagaaccct cattcccaag ttagttggat tccaagtcca taaaccgggt caaaagaata    33960
cagtaatttc ctactggagc tctaagtggt ggttttcacg gaggactcgg caccatcctc    34020
ccacctgcct cctcccatcg aacattcctt tttaagaaaa acacacacca ggctccggga    34080
agctgacgta acatcctga ggaaataacc actgtaagtg gcttctaaac ccatttcccc    34140
aaggaaataa tcagcacctc tttcccaaga cagctccagg taagcaagcg gtgaagggag    34200
ctgcaccacc gcgttctcaa aagtaaaggc gcttgcggaa ctgtctactg atttgtaagc    34260
gcgcgcccat ccactgtcgc atttaatctt ccgaacgacc cacgaggtgg taaaggcggg    34320
gattattttc ttcattttac gggtgagaaa ccgaggccca cagcgctcgt tcctgtagcc    34380
ggggtcaggc agggcacacc tagggagcc tctgccttcg agcccggga ccgccccgcg    34440 gcaccacgag atctccccag tcagcccgtg tgcggctgcg gccgcatggc ctcattgttt    34500
tgggaagacg tccctctgtg aggatcttgg gcgactctat gaaccgcggg cccagccgct    34560
ctgcggaacg atccgcagcg ggacgcaaag ggcgcggcga gccggcggc tcccggaaca    34620 aaggacagca gagcgcgcgg ggcccgaagg ggcgtccgcc ctagtgggcg gcggagggg    34680 atgcgcgcgg agaggaccag cgcgcaccgc cccggcccgc ccctcaaatc ctccttcctt    34740
ctctctcgca ctcggagacg gtccctggga gatccgggag ggggcgcagc tcgccgtcct    34800
cgccggcaag tgccgtcgca acctccctct gccgccaccc ccaccccgag aagcgcacaa    34860
agagcggccg ggcagggagc gctcacctcc cgtcggggcg gggccgcggg cggggccggc    34920
gcgcgctccg cagcgcccgc cttaaagggc ccgcccgctc ctcgcgcgca ctgcgcatgc    34980
tcggccgcgg ggcacggagg ggagggatgg gaacagcggg cgcgcacgcc cgcgccgccc    35040
gctggcgctg tggcctgcgt ccccgcgtg gcggcgcgg gctcgtgcgc gtgtcagaac    35100
ccgcagggtc tcggcccggg cgccgggcgt gtgctggaca ctggtgccat gcattccaga    35160
ggtcgccagc ggccgggcgg gccgagctcg cgcggcagcc agcttttagc tttcccatcc    35220
tcagtttcag ggccagttgg gcgaagtgct gcccaaggag acagaaatgc aggcgcgggc    35280
gcgcgcgcgc gcggttgcca gtgtgggcgg gcgtgtgctt ttgtgtctcg tgcgctcccg    35340
cgcaggtgga caacccgcgc cgggagtcac tctgcccgtg cgccccaaga cctggagtcc    35400
cgttttccgt gtcggagggc tcgggtcgcc cttttgggcg gactacagac tcttctcaca    35460
gaggaagctt tggctccacg gatggtttat ttggagccac taacgggact tcctgaggac    35520
cgctctttta gagcccggct ccaggcatca gagttgggcg cgttttcttt tctcagtcag    35580
gcgagggagg agacttaggg acaatgattg tcctcggctg ataggtacat ccaagtgtcc    35640
cgagcctgcc agtcccgcat tagacaacaa agagaggcgt tagcggcggc gggggagggg    35700
```

| | |
|---|---|
| cgcggccggg aggaggacgg ggcgggctgc ggcgagcgcg ggggtggggg gtggcgctct | 35760 |
| ctctccgctc gctcaacccg cggcctcctc ccgcccccgg cctggcgcgc gccaatcgcc | 35820 |
| tcccccagcg atagtgtcag tagcattgtg gtgtcagctc ccgcctgtga cgttgcgcct | 35880 |
| ccctcgtccc cctccggagt cgtctggctg cagaggctc | 35919 |

<210> SEQ ID NO 3
<211> LENGTH: 836
<212> TYPE: DNA
<213> ORGANISM: Human

<400> SEQUENCE: 3

| | |
|---|---|
| gtaggtcgag agggatgggg gaggtgggtg ggggtggtgt agggtctcag gccactgcct | 60 |
| cgagggggaag gcgtgttcag tatcgggatc cgcggcgtgg ggtgccttgg ggagagagga | 120 |
| agagccgcgc gatgggccgg cgccccagac aaagaaagtg caggcaggct gtctcccgga | 180 |
| gccgcgccgc tgccctggcg ggatgcactt tcttctgcta aaatcactgc cttctcccct | 240 |
| aacgcccccc aaccagccca cctccagaaa gacaatttaa atgtaagatg cttgggggag | 300 |
| ggggcctttg atcagtcctt tgggaggagg aaggaggagg agtgagcata ggatgggagg | 360 |
| aggattctgg atttctgcaa agcggaatgg agcccagagg aggaacaatg ggtcccggga | 420 |
| ctcacacccc acccctaccc ccagtcgac cagcgctgag gcatcgcgac ttcagctgcc | 480 |
| ttccccgagc cccttccccg tgtcttcaga gctgacggcg cgcccagctg atcccagcg | 540 |
| gcatctcccc agatgacttt tctgggattc tcgggtttgg ttcgggacga ctgcagtcac | 600 |
| tgggggaggg ccaggcagcc aatgggctgt tcctcgagcg cctcgcgggt gggatccgct | 660 |
| gcccagcccg tggcgcggcc cgaggtcagt gagggagacg ccccctttcc gcccatctct | 720 |
| tgtcctgccg tctcgctgtc ctggacgcgg gctgtcccg gtcccgcgg ttaccccagg | 780 |
| ataatgggcg tgtctgtctc tctctcccac tccctcctcc gcaccctggt tcgtag | 836 |

<210> SEQ ID NO 4
<211> LENGTH: 3416
<212> TYPE: DNA
<213> ORGANISM: Mouse

<400> SEQUENCE: 4

| | |
|---|---|
| tgttcgcttt gcgctcggca ttgtggccag ccagccgggc actcgggggg cacgcgcggc | 60 |
| cgccgctcga gctctgcccc cacccccaacc gccagcagat ctggggtggg gacccaggcg | 120 |
| ggggctcttg cagccactgc ccggtgcgga ttgcacgcag agaccactc ctccgagcgc | 180 |
| cgaaaaacga gccacggagc cctccgcagc cgaccggcct cccgcccct gactgccggc | 240 |
| ttcccggctg cctttgtggc tgcaccttct agctgccgag cagagagccg gctgggcgc | 300 |
| ggcgcgcacg gcggagcgat gcccagctcg ctgtttgcag acctggagcg caacggcagc | 360 |
| ggcggcggcg gggaggcgg cggcggggga ggcggcggtg gcagcggcgg gggagagact | 420 |
| ctggatgacc aaagagccct gcagcttgcg ctcgatcagc tctccctgtt gggactggac | 480 |
| agtgatgagg gcgcctcttt gtacgacagc gaaccgcgca agaagagcgt gaacatgacc | 540 |
| gagtgcgtgc cggtacccag ttccgaacac gtcgcggaga tcgtagggag gcaaggttgt | 600 |
| aaaatcaaag ctttgagggc gaagaccaac acttacatca agaccccagt tcgcggggag | 660 |
| gagcctgtct ttgttgtgac gggcaggaag gaggatgtgg ctatggctcg gagggagatc | 720 |
| atctctgccg cagagcactt ctccatgatc cgagcctctc gtaacaagaa cacggctctc | 780 |
| aacggagctg tgcccggacc gcccaacctg ccgggacaga ccactatcca agtgagggtg | 840 |

```
ccataccgcg tggtagggct cgtggtgggt ccaaagggcg ccacgatcaa gcgcattcaa      900
cagcagacac atacatatat tgtgacaccc agccgagaca aggagccagt tttcgaggtg      960
actggcatgc cagagaacgt ggatcgcgct agagaggaga tcgaagctca catcgcgctg     1020
cgcaccggtg gcatcatcga gctgacagac gagaacgact ccatgccaa tggcacagac      1080 gtgggctttg atctgcatca cgggtccggc gggtccgggc cgggcagcct ctggagcaag     1140
cccaccccaa gcatcactcc tacacctggc cgcaagccct tctccagcta cgcaacgac      1200 agctccagct cgcttggcag cgcatccaca gactcttact tcggtggtgg gaccagcggc     1260
agcgcagctg ctacttcacg cctggcggac tatagccctc ccagccctgc actcagcttt     1320
gctcacaatg ggaacaacaa caataacggc aatggttaca cctacacagc ggggaagcc      1380 tcagtacctt ccccagatgg gggtcctgag ctgcagccta ctttcgaccc agctcccgcc     1440
ccaccacctg gacacccct tctctgggcc cagttcgagc gctctccagg aggtggatct      1500
gcagcaccag tatcctcttc ctgctcttct tcggcatcct catctgcctc gtcgtcctct     1560
gtggtctttc ccgggggtgg cgccagcagc acaccctcca atgccaatct ggggctgctg     1620
gtgcaccgtc gactgcaccc gggcaccagc tgcccgcgcc tgtctccgcc cttgcacatg     1680
gccacggggg cgggagagca ccaccttgct cgccgcgtgc gcagcgaccc gggcggtgga     1740
ggcctggcct acgctgccta tgctaatggg ctagggacgc agctccctgg cctgccctcg     1800
tcggacactt cgggctcctc ctcgtcctct agctcctcct ccagctcttc ctcctcttcc     1860
tctgggctga ggcgcaaagg cagccgcgac tgctctgtgt gcttcgagag tgaagtgatc     1920
gccgcgctgg tgccctgtgg ccacaacctc ttctgcatgg agtgtgccaa ccgcatttgt     1980
gagaagagcg agcccgagtg tcccgtctgc cacacggcgg tcactcaggc catccgcatt     2040
ttttcctgaa ggcagtgcgc gcgcgcgcac tgcagggaag gagggtcctc tctcgaccct     2100
cattccctag ggtctaccctg cccagacgcc tctggtgccc acctctttcc accccacccct   2160 catcactctc agagatccca gaggagcttg gaaagctgta gtatccgctc atttttaaaa     2220
tgtcattttt aaacaaagga acttgccagg atctctgcat caggagtact gtagcctccg     2280
aaccacctga attgcatgct ctataaataa taggaacggc gacattctag taacgatagt     2340
ttttacactg tacttaatag gaagcttcca aaagaaaacc ccacaagttt tccattttct     2400
tgaagtagaa aaatgaacag taattatgaa gatgattaat aattgtgcta tgggatgtgt     2460
ggactgtttt gtgtgtttcc ctttgtgggt gggttcctac agcgctcgtt ctagaacaca     2520
agtggatcct ttttgaatgt tcatggaagg gccaggagtt ctgtacagcc aggaccctgc     2580
agctttatta agttaaaaac tgtaacatat ctcttatata ttaaaaaaaa aaaccttttaa    2640 aagttttaaa gagaaattgc attaatacag attgaagtat tttattcttt ttttgacttg     2700
aaaaattata tttcatattg caaagatgtt tacaagtatt ttaatttaag ttcagtgaac     2760 tttttttgtag ctgggttaaa tcttttttatt tttagtatgg ccttatgcca aagaacactg    2820
tattatttta ataatcacac gattgtgacg gattacaaac cataaaatgt ataacgtttt     2880
gagcagtatt ctgttgggat ggagatttta taggttcaga caaatcttct agatctgctt     2940
cacccagcat attttctatt cagtgatata aagcatattt tattctatat tattacaaaa     3000
aatggaaatg tataaacatg tcaaaaggaa cagttgatgc tttctaacat ttgtataaat     3060
agaattcagt gcaaattaca gaaattctgt tgcaccgcta tagtttttagt gtttctatttt    3120 taatacattt gtttaccact cgtttatgta tatgtaggtg acgttacttg agcttaaatg     3180
```

```
tactttactg agcaaagttt aaaaaaaaac aaagtatatt ttattttatg ataaagggcc      3240
tttaacctca tggtcaaata ctaatattat atttgctgag acaagatttg aaattgtatc      3300
aagagtttta tttttctgac atttaaagtt ctacataata aaggtaaact taagtaatgg      3360
tgctacttca ttttttaagt atttctatat aataaaaaca ttgaagaaaa atcact          3416
```

<210> SEQ ID NO 5
<211> LENGTH: 569
<212> TYPE: PRT
<213> ORGANISM: Human

<400> SEQUENCE: 5

```
Met Pro Ser Ser Leu Phe Ala Asp Leu Glu Arg Asn Gly Ser Gly Gly
1               5                   10                  15

Gly Gly Gly Gly Ser Ser Gly Gly Glu Thr Leu Asp Asp Gln Arg
            20                  25                  30

Ala Leu Gln Leu Ala Leu Asp Gln Leu Ser Leu Leu Gly Leu Asp Ser
        35                  40                  45

Asp Glu Gly Ala Ser Leu Tyr Asp Ser Glu Pro Arg Lys Lys Ser Val
    50                  55                  60

Asn Met Thr Glu Cys Val Pro Val Pro Ser Ser Glu His Val Ala Glu
65                  70                  75                  80

Ile Val Gly Arg Gln Gly Cys Lys Ile Lys Ala Leu Arg Ala Lys Thr
                85                  90                  95

Asn Thr Tyr Ile Lys Thr Pro Val Arg Gly Glu Pro Val Phe Val
            100                 105                 110

Val Thr Gly Arg Lys Glu Asp Val Ala Met Ala Arg Arg Glu Ile Ile
        115                 120                 125

Ser Ala Ala Glu His Phe Ser Met Ile Arg Ala Ser Arg Asn Lys Asn
    130                 135                 140

Thr Ala Leu Asn Gly Ala Val Pro Gly Pro Pro Asn Leu Pro Gly Gln
145                 150                 155                 160

Thr Thr Ile Gln Val Arg Val Pro Tyr Arg Val Val Gly Leu Val Val
                165                 170                 175

Gly Pro Lys Gly Ala Thr Ile Lys Arg Ile Gln Gln Gln Thr His Thr
            180                 185                 190

Tyr Ile Val Thr Pro Ser Arg Asp Lys Glu Pro Val Phe Glu Val Thr
        195                 200                 205

Gly Met Pro Glu Asn Val Asp Arg Ala Arg Glu Glu Ile Glu Ala His
    210                 215                 220

Ile Ala Leu Arg Thr Gly Gly Ile Ile Glu Leu Thr Asp Glu Asn Asp
225                 230                 235                 240

Phe His Ala Asn Gly Thr Asp Val Gly Phe Asp Leu His His Gly Ser
                245                 250                 255

Gly Gly Ser Gly Pro Gly Ser Leu Trp Ser Lys Pro Thr Pro Ser Ile
            260                 265                 270

Thr Pro Thr Pro Gly Arg Lys Pro Phe Ser Ser Tyr Arg Asn Asp Ser
        275                 280                 285

Ser Ser Ser Leu Gly Ser Ala Ser Thr Asp Ser Tyr Phe Gly Gly Gly
    290                 295                 300

Thr Ser Ser Ser Ala Ala Ala Thr Gln Arg Leu Ala Asp Tyr Ser Pro
305                 310                 315                 320

Pro Ser Pro Ala Leu Ser Phe Ala His Asn Gly Asn Asn Asn Asn Asn
                325                 330                 335
```

Gly Asn Gly Tyr Thr Tyr Thr Ala Gly Glu Ala Ser Val Pro Ser
            340                 345                 350

Pro Asp Gly Cys Pro Glu Leu Gln Pro Thr Phe Asp Pro Ala Pro Ala
        355                 360                 365

Pro Pro Pro Gly Ala Pro Leu Ile Trp Ala Gln Phe Glu Arg Ser Pro
370                 375                 380

Gly Gly Gly Pro Ala Ala Pro Val Ser Ser Cys Ser Ser Ser Ala
385                 390                 395                 400

Ser Ser Ser Ala Ser Ser Ser Val Val Phe Pro Gly Gly Gly Ala
            405                 410                 415

Ser Ala Pro Ser Asn Ala Asn Leu Gly Leu Leu Val His Arg Arg Leu
        420                 425                 430

His Pro Gly Thr Ser Cys Pro Arg Leu Ser Pro Pro Leu His Met Ala
    435                 440                 445

Pro Gly Ala Gly Glu His His Leu Ala Arg Arg Val Arg Ser Asp Pro
450                 455                 460

Gly Gly Gly Gly Leu Ala Tyr Ala Ala Tyr Ala Asn Gly Leu Gly Ala
465                 470                 475                 480

Gln Leu Pro Gly Leu Gln Pro Ser Asp Thr Ser Gly Ser Ser Ser Ser
            485                 490                 495

Ser Ser Ser Ser Ser Ser Ser Ser Ser Ser Gly Leu Arg Arg
        500                 505                 510

Lys Gly Ser Arg Asp Cys Ser Val Cys Phe Glu Ser Glu Val Ile Ala
    515                 520                 525

Ala Leu Val Pro Cys Gly His Asn Leu Phe Cys Met Glu Cys Ala Asn
530                 535                 540

Arg Ile Cys Glu Lys Ser Glu Pro Cys Pro Val Cys His Thr Ala
545                 550                 555                 560

Val Thr Gln Ala Ile Arg Ile Phe Ser
            565

<210> SEQ ID NO 6
<211> LENGTH: 576
<212> TYPE: PRT
<213> ORGANISM: Mouse

<400> SEQUENCE: 6

Met Pro Ser Ser Leu Phe Ala Asp Leu Glu Arg Asn Gly Ser Gly Gly
1               5                   10                  15

Gly Gly Gly Gly Gly Gly Gly Gly Gly Gly Ser Gly Gly Gly
            20                  25                  30

Glu Thr Leu Asp Asp Gln Arg Ala Leu Gln Leu Ala Leu Asp Gln Leu
        35                  40                  45

Ser Leu Leu Gly Leu Asp Ser Asp Glu Gly Ala Ser Leu Tyr Asp Ser
    50                  55                  60

Glu Pro Arg Lys Lys Ser Val Asn Met Thr Glu Cys Val Pro Val Pro
65                  70                  75                  80

Ser Ser Glu His Val Ala Glu Ile Val Gly Arg Gln Gly Cys Lys Ile
                85                  90                  95

Lys Ala Leu Arg Ala Lys Thr Asn Thr Tyr Ile Lys Thr Pro Val Arg
            100                 105                 110

Gly Glu Glu Pro Val Phe Val Val Thr Gly Arg Lys Glu Asp Val Ala
        115                 120                 125

Met Ala Arg Arg Glu Ile Ile Ser Ala Ala Glu His Phe Ser Met Ile
    130                 135                 140

```
Arg Ala Ser Arg Asn Lys Asn Thr Ala Leu Asn Gly Ala Val Pro Gly
145                 150                 155                 160

Pro Pro Asn Leu Pro Gly Gln Thr Thr Ile Gln Val Arg Val Pro Tyr
                165                 170                 175

Arg Val Val Gly Leu Val Val Gly Pro Lys Gly Ala Thr Ile Lys Arg
            180                 185                 190

Ile Gln Gln Gln Thr His Thr Tyr Ile Val Thr Pro Ser Arg Asp Lys
        195                 200                 205

Glu Pro Val Phe Glu Val Thr Gly Met Pro Glu Asn Val Asp Arg Ala
    210                 215                 220

Arg Glu Glu Ile Glu Ala His Ile Ala Leu Arg Thr Gly Gly Ile Ile
225                 230                 235                 240

Glu Leu Thr Asp Glu Asn Asp Phe His Ala Asn Gly Thr Asp Val Gly
                245                 250                 255

Phe Asp Leu His His Gly Ser Gly Gly Ser Gly Pro Gly Ser Leu Trp
                260                 265                 270

Ser Lys Pro Thr Pro Ser Ile Thr Pro Thr Pro Gly Arg Lys Pro Phe
            275                 280                 285

Ser Ser Tyr Arg Asn Asp Ser Ser Ser Leu Gly Ser Ala Ser Thr
        290                 295                 300

Asp Ser Tyr Phe Gly Gly Gly Thr Ser Gly Ser Ala Ala Ala Thr Ser
305                 310                 315                 320

Arg Leu Ala Asp Tyr Ser Pro Pro Ser Pro Ala Leu Ser Phe Ala His
                325                 330                 335

Asn Gly Asn Asn Asn Asn Gly Asn Gly Tyr Thr Tyr Thr Ala Gly
                340                 345                 350

Glu Ala Ser Val Pro Ser Pro Asp Gly Gly Pro Glu Leu Gln Pro Thr
            355                 360                 365

Phe Asp Pro Ala Pro Ala Pro Pro Gly Thr Pro Leu Leu Trp Ala
    370                 375                 380

Gln Phe Glu Arg Ser Pro Gly Gly Gly Ser Ala Ala Pro Val Ser Ser
385                 390                 395                 400

Ser Cys Ser Ser Ser Ala Ser Ser Ser Ala Ser Ser Ser Val Val
                405                 410                 415

Phe Pro Gly Gly Gly Ala Ser Ser Thr Pro Ser Asn Ala Asn Leu Gly
                420                 425                 430

Leu Leu Val His Arg Arg Leu His Pro Gly Thr Ser Cys Pro Arg Leu
            435                 440                 445

Ser Pro Pro Leu His Met Ala Thr Gly Ala Gly Glu His His Leu Ala
            450                 455                 460

Arg Arg Val Arg Ser Asp Pro Gly Gly Gly Leu Ala Tyr Ala Ala
465                 470                 475                 480

Tyr Ala Asn Gly Leu Gly Thr Gln Leu Pro Gly Leu Pro Ser Ser Asp
                485                 490                 495

Thr Ser Gly Ser Ser Ser Ser Ser Ser Ser Ser Ser Ser Ser
            500                 505                 510

Ser Ser Ser Gly Leu Arg Arg Lys Gly Ser Arg Asp Cys Ser Val Cys
        515                 520                 525

Phe Glu Ser Glu Val Ile Ala Ala Leu Val Pro Cys Gly His Asn Leu
    530                 535                 540

Phe Cys Met Glu Cys Ala Asn Arg Ile Cys Glu Lys Ser Glu Pro Glu
545                 550                 555                 560
```

Cys Pro Val Cys His Thr Ala Val Thr Gln Ala Ile Arg Ile Phe Ser
              565                 570                 575

<210> SEQ ID NO 7
<211> LENGTH: 30
<212> TYPE: DNA
<213> ORGANISM: Artificial Sequence
<220> FEATURE:
<223> OTHER INFORMATION: MEX3B primer Fw1

<400> SEQUENCE: 7
cgtcgtcctc tgtggtcttt cccggggtg                                    30

<210> SEQ ID NO 8
<211> LENGTH: 30
<212> TYPE: DNA
<213> ORGANISM: Artificial Sequence
<220> FEATURE:
<223> OTHER INFORMATION: MEX3B primer Rv1

<400> SEQUENCE: 8
tcaggaaaaa atgcggatgg cctgagtgac                                   30

<210> SEQ ID NO 9
<211> LENGTH: 20
<212> TYPE: DNA
<213> ORGANISM: Artificial Sequence
<220> FEATURE:
<223> OTHER INFORMATION: Mouse GAPDH primer Fw1

<400> SEQUENCE: 9
agagacagcc gcatcttctt                                              20

<210> SEQ ID NO 10
<211> LENGTH: 20
<212> TYPE: DNA
<213> ORGANISM: Artificial Sequence
<220> FEATURE:
<223> OTHER INFORMATION: Mouse GAPDH primer Rv1

<400> SEQUENCE: 10
gacaagcttc ccattctcgg                                              20

<210> SEQ ID NO 11
<211> LENGTH: 25
<212> TYPE: DNA
<213> ORGANISM: Artificial Sequence
<220> FEATURE:
<223> OTHER INFORMATION: Mouse IL-6 primer Fw1

<400> SEQUENCE: 11
gctaccaaac tggatataat cagga                                        25

<210> SEQ ID NO 12
<211> LENGTH: 24
<212> TYPE: DNA
<213> ORGANISM: Artificial Sequence
<220> FEATURE:
<223> OTHER INFORMATION: Mouse IL-6 primer Rv1

<400> SEQUENCE: 12
ccaggtagct atggtactcc agaa                                         24

<210> SEQ ID NO 13
<211> LENGTH: 20
<212> TYPE: DNA

```
<213> ORGANISM: Artificial Sequence
<220> FEATURE:
<223> OTHER INFORMATION: Mouse CXCL5 primer Fw1

<400> SEQUENCE: 13
cagaaggagg tctgtctgga                                                 20

<210> SEQ ID NO 14
<211> LENGTH: 20
<212> TYPE: DNA
<213> ORGANISM: Artificial Sequence
<220> FEATURE:
<223> OTHER INFORMATION: Mouse CXCL5 primer Rv1

<400> SEQUENCE: 14
tgcattccgc ttagctttct                                                 20

<210> SEQ ID NO 15
<211> LENGTH: 4368
<212> TYPE: DNA
<213> ORGANISM: Human

<400> SEQUENCE: 15
tcaagaggcg ggaggagag gaggaaaaag cgctgagtga gggcgggcgg gcgggcggga       60
gggagggagt ggaggagccg gggagggggct ccttaaagaa acgcttctgt cgctcgcctg    120
ctcgcttttc gctcggcatt gcggccagcc agccgggcac tcgggggca cgcgcggcca     180 ccgctagagc tctgccccca ccccacccgc cagcaggtct ggggtgggga cccaggtggg    240
ggctcctgca gccactgccc ggtgcggacc gcacggagcg acccactcct cccagcaccg    300
aggaagaagc aacggagccc tcagcaggcg accggcctcc ccgcccctga ccacccgctt    360
cccggctgcc tttgtggccg cagcttctcg ccgccgagcc gagggccggc ggggcgcggg    420
cgcgcacggc cgagcgatgc ccagctcgct gttcgcagac ctggagcgca acggcagcgg    480
cggcggcggg ggcggcagca gcggaggggg agagaccctg gatgaccaaa gagccctgca    540
gctcgcgctc gaccagctct ccctgctggg gctggacagt gacgagggcg cctctctgta    600
cgacagcgag ccgcgcaaga gagcgtgaa catgaccgag tgcgtgccag tacccagttc     660
tgagcatgtc gccgagatcg tggggcggca aggtaggtcg aggagggatg gggaggtggg    720
tgggggtggt gtagggtctc aggccactgc ctcgagggga aggcgtgttc agtatcggga    780
tccgcggcgt ggggtgcctt ggggagagag gaaagagccgc gcgatgggcc ggcgcccag    840 acaaagaaag tgcaggcagg ctgtctcccg gagccgcgcc gctgccctgg cgggatgcac    900
tttcttctgc taaaatcact gccttctccc ctaacgcccc caaccagcc cacctccaga    960 aagacaattt aaatgtaaga tgcttgggg aggggccttt tgatcagtcc tttgggagga    1020
ggaaggagga ggagtgagca taggatggga ggaggattct ggatttctgc aaagcggaat   1080
ggagcccaga ggaggaacaa tgggtcccgg gactcacacc ccacccccta cccccagtcg   1140
accagcgctg aggcatcgcg acttcagctg ccttccccga gccccttccc cgtgtcttca   1200
gagctgacgg cgcgcccagc tggatcccag cggcatctcc ccagatgact tttctgggat   1260
tctcgggttt ggttcgggac gactgcagtc actgggggag ggccaggcag ccaatgggct   1320
gttcctcgag cgcctcgcgg gtgggatccg ctgcccagcc cgtggcgcgg cccgaggtca   1380
gtgagggaga cgcccccttt ccgcccatct cttgtcctgc cgtctcgctg tcctggacgc   1440
gggctgtccc cggtccccgc ggttaccccca ggataatggg cgtgtctgtc tctctctccc   1500 actcccctcct ccgcaccctg gttcgtaggt tgtaaaatca aagcgctgcg ggcgaagacc   1560
```

```
aatacttaca tcaagacccc agttcgcggg gaggagcctg tctttgttgt gacgggcagg    1620
aaggaggatg tggccatggc tcggaggag atcatctctg ctgccgagca cttctccatg    1680
atccgcgcct cccggaataa gaacacggca ctcaacggcg cggtgcctgg gccgcccaac    1740
ctgcccgggc agaccaccat ccaagtgcgg gtaccctacc gcgtggtggg gctcgtggtg    1800
gggcccaaag gcgccacaat caagcgcatc cagcagcaga cgcacacgta catcgtgacg    1860
cccagccggg ataaggagcc ggtgttcgag gtgaccggca tgccagagaa cgtggatcgc    1920
gctcgagagg agattgaggc gcacattgct ctgcgtaccg gcggcatcat tgagctcaca    1980
gacgagaacg acttccacgc caacggcacc gatgtgggct tcgatctgca tcatgggtcc    2040
ggcgggtccg gcccaggcag cctctggagc aagcccaccc ccagcatcac gcccaccccc    2100
ggccgcaagc ctttctctag ctaccgcaac gacagctcca gctcgcttgg cagtgcttcc    2160
acagactctt atttcggcgg cgggaccagc agcagcgcag cggctaccca gcgcctggcg    2220
gactacagcc cccctagccc cgccctgagc tttgcgcaca acggaaacaa taacaataac    2280
ggcaatgggt acacctacac agcggggga gaagcctcag tgccatcccc cgacggctgc    2340
cccgagctgc agcccacttt tgacccggct ccgctcccc cacctggggc accacttatc    2400
tgggcccagt tcgagcggtc cccggaggc ggacctgcag ctccggtatc ttcttcctgc    2460
tcttcttctg catcttcgtc tgcttcttcc tcctccgtgg tcttcccgg gggtggcgcc    2520 agtgcgccct ccaacgccaa cctggggcta ttggtgcacc gccggctgca ccctggcacc    2580
agctgcccgc gcctgtctcc acccttgcac atggccccgg gggcgggaga gcaccacctg    2640
gctcgccggg tgcgcagcga cccgggtgga ggaggcctgg cctacgccgc ttatgccaac    2700
gggctggggg cacagctgcc tggcttgcag ccgtcggaca cgtcgggctc ctcctcttcg    2760
tccagctcct cctccagctc ttcatcctct tcctccgggc ttcggcgtaa aggcagccgc    2820
gactgctccg tgtgcttcga gagcgaagtg attgccgcgc tggtgccctg tggccacaac    2880
ctcttctgca tggagtgcgc caatcgcatc tgtgagaaga gcgagcccga gtgcccggtc    2940
tgccacaccg cggtcactca ggccatccgc atcttttctt aaaggcagcg ggcgctgcta    3000
gtgcgcaccg tgctggggga aggggaaacc cctccccacc ctctttcccc agcgctcgcc    3060
tgcctccctg ggtgccccc ctctcccttc tccttcccgg ccccaccaac actctgagat    3120
ccgagaggag cttggaaagc tgtagtatcc gctcattttt aaaatttaat ttttaagtaa    3180
aggaatttgc caggatatct gcatcaagag tactgtagcc tgggaaacct gaacacctga    3240
aatgcatgct ctataaataa taggaacggc gacattctag taatgatagt ttttacactg    3300
tacttaatag gaagcttcca aaagaagaaa accccacaag ttttccattt tcttaaagta    3360
ggaaaaaatg aacagtaata attatgatga agatgatagt agtgctatgg gatgtgtgga    3420
ctgtttagtg tgttccccctt tgtgggtggg ttcctatgat acttattata gaacacagtg    3480
gatccttttt gaatgttcgt ggaagggcca ggagttcctg tgaaaccagg atactgcagc    3540
tttattaaag ttaaagaaac tgtaacatat ctcttatata ttaaaaacgt ttaaaagttt    3600
taaagagaaa ttgcattaat acagattgaa gtatttatt cttttttgac ttgaaaaatt    3660
atatttcata ttgcaaagat gtttacaagt attttaattt aagttcagtg aacttttttg    3720
tagctgggtt aaatcttttt attttagtat ggccttatgg caaagaacac tgtattattt    3780
taataatcac acaattgtga cggaattaca accataaaat gtgtaatgtt ttgaacagta    3840
ttctgttggg atggagattt tataggttca gacaaatctt ctagatctgc ttcacccagc    3900
```

```
atattttcta ttcagtgata taaagcatat tttattctat attattacaa aaacggaaat    3960
gtataaacat gtcaaaaaga actgttgatg ctttctaaca tttgtataaa tagaattcag    4020
tgcaagttac aaaaattctg ttgcaccact ctagttttag tatttctatt ttaatacatt    4080
tgtttaccac ttgtttatgt atatgtaggt gatgttactt gagcttaaat gtactttact    4140
gagcaaagtt taaaaaacaa agtatatttt attttatgat aaagggcctt taacctcatg    4200
gtcaaatact aatattatat ttgctgagac aagatttgaa attgtatcaa gagtttttatt   4260 tttctgacat ttaaagttct acataataaa ggtaaaactt aagtaatggt gctacttcat    4320
tttttaagta tttctatata aataaaatat tgaagaaaat cttaaaaa                 4368
```

<210> SEQ ID NO 16
<211> LENGTH: 15
<212> TYPE: DNA
<213> ORGANISM: Artificial Sequence
<220> FEATURE:
<223> OTHER INFORMATION: mouseMex3bspecific gapmer

<400> SEQUENCE: 16
acataaacga gtggt    15

<210> SEQ ID NO 17
<211> LENGTH: 20
<212> TYPE: DNA
<213> ORGANISM: Artificial Sequence
<220> FEATURE:
<223> OTHER INFORMATION: mouseGAPDH-Fw2

<400> SEQUENCE: 17
tgtgtccgtc gtggatctga    20

<210> SEQ ID NO 18
<211> LENGTH: 21
<212> TYPE: DNA
<213> ORGANISM: Artificial Sequence
<220> FEATURE:
<223> OTHER INFORMATION: mouseGAPDH-Rv2

<400> SEQUENCE: 18
ttgctgttga agtcgcagga g    21

<210> SEQ ID NO 19
<211> LENGTH: 21
<212> TYPE: DNA
<213> ORGANISM: Artificial Sequence
<220> FEATURE:
<223> OTHER INFORMATION: mouseTNF-Fw

<400> SEQUENCE: 19
tcttctcatt cctgcttgtg g    21

<210> SEQ ID NO 20
<211> LENGTH: 20
<212> TYPE: DNA
<213> ORGANISM: Artificial Sequence
<220> FEATURE:
<223> OTHER INFORMATION: mouseTNF-Rv

<400> SEQUENCE: 20
gaggccattt gggaacttct    20

<210> SEQ ID NO 21
<211> LENGTH: 20

```
<212> TYPE: DNA
<213> ORGANISM: Artificial Sequence
<220> FEATURE:
<223> OTHER INFORMATION: mouseG-CSF-Fw

<400> SEQUENCE: 21
cctggagcaa gtgaggaaga                                          20

<210> SEQ ID NO 22
<211> LENGTH: 20
<212> TYPE: DNA
<213> ORGANISM: Artificial Sequence
<220> FEATURE:
<223> OTHER INFORMATION: mouseG-CSF-Rv

<400> SEQUENCE: 22
ggggtgacac agcttgtagg                                          20

<210> SEQ ID NO 23
<211> LENGTH: 23
<212> TYPE: DNA
<213> ORGANISM: Artificial Sequence
<220> FEATURE:
<223> OTHER INFORMATION: mouseIL-13-Fw

<400> SEQUENCE: 23
cctctgaccc ttaaggagct tat                                      23

<210> SEQ ID NO 24
<211> LENGTH: 18
<212> TYPE: DNA
<213> ORGANISM: Artificial Sequence
<220> FEATURE:
<223> OTHER INFORMATION: mouseIL-13-Rv

<400> SEQUENCE: 24
cgttgcacag gggagtct                                            18

<210> SEQ ID NO 25
<211> LENGTH: 26
<212> TYPE: DNA
<213> ORGANISM: Artificial Sequence
<220> FEATURE:
<223> OTHER INFORMATION: mouseCXCL2-Fw

<400> SEQUENCE: 25
aaaatcatcc aaaagatact gaacaa                                   26

<210> SEQ ID NO 26
<211> LENGTH: 20
<212> TYPE: DNA
<213> ORGANISM: Artificial Sequence
<220> FEATURE:
<223> OTHER INFORMATION: mouseCXCL2-Rv

<400> SEQUENCE: 26
ctttggttct tccgttgagg                                          20

<210> SEQ ID NO 27
<211> LENGTH: 20
<212> TYPE: DNA
<213> ORGANISM: Artificial Sequence
<220> FEATURE:
<223> OTHER INFORMATION: mouseCXCL1-Fw

<400> SEQUENCE: 27
```

```
agactccagc cacactccaa                                          20

<210> SEQ ID NO 28
<211> LENGTH: 18
<212> TYPE: DNA
<213> ORGANISM: Artificial Sequence
<220> FEATURE:
<223> OTHER INFORMATION: mouseCXCL1-Rv

<400> SEQUENCE: 28
tgacagcgca gctcattg                                            18
```

METHOD FOR SCREENING PROPHYLACTIC OR THERAPEUTIC AGENTS FOR DISEASES CAUSED BY INTERLEUKIN 6, INTERLEUKIN 13, TNF, G-CSF, CXCL1, CXCL2, OR CXCL5 AND AGENT FOR THE PREVENTION OR TREATMENT OF DISEASES CAUSED BY INTERLEUKIN 6, INTERLEUKIN 13, TNF, G-CSF, CXCL1, CXCL2, OR CXCL5

TECHNICAL FIELD

The present invention relates to a method for screening prophylactic or therapeutic agents for diseases caused by interleukin 6 (IL-6), interleukin 13 (IL-13), Tumor Necrosis Factor (TNF), Granulocyte-Colony Stimulating Factor or colony-stimulating factor 3 (CSF 3) (G-CSF), CXCL1, CXCL2, or CXCL5 and a prophylactic or therapeutic agent for diseases caused by IL-6, IL-13, TNF, G-CSF, CXCL1, CXCL2, or CXCL5.

BACKGROUND ART

Allergic airway inflammation has been considered as an allergic disorder that is caused by various allergens (e.g., Non-Patent Document 1).

However, people ending up dead due to aggravated asthma are mostly the elderlies, and the airway inflammation site of those patients having severe asthma are characterized in that, neutrophils relating to a defense against infection are seen in large numbers rather than eosinophils which accumulate by an allergic response. Thanks to a progress in immunology in recent years, it becomes evident that Th17 type immune cells (i.e., cells responsible for an immune response corresponding to a defense against infection by secreting mainly IL-17) in those patients with severe asthma are responsible for the basic symptom of disease (e.g., Non-Patent Document 2).

It has been also reported that a patient with more severe case has higher level of interleukin 17 (IL-17) in blood serum, which is one type of cytokines. IL-17 increases secretion of chemokines (CXCL1, CXCL2, CXCL5, and the like) from lung tissues, and those chemokines recruit neutrophils to an inflammation site. Infiltration of neutrophils repeatedly induces chronic inflammation, and, when thickening of smooth muscle, fibrosis of airway mucous membrane, hyperplasia of airway submucosal gland, or the like progresses, irreversible airway remodeling is eventually caused. Once having such state, it is easy to have dyspnea, making it very difficult to be treated.

Meanwhile, IL-6 is an important cytokine that is involved in inflammation, hematopoiesis, bone metabolism, tumor aggravation, or the like, and the activity of IL-6 is known to contribute mainly to a transition from acute inflammation to acquired immune response or an onset of a chronic inflammatory disorder (e.g., Non-Patent Document 3).

It is known that, as IL-6 binds to a complex of IL-6 receptor subunit and gp130 (signal transfer subunit) expressed on a surface of a target cell, IL-6 intracellular signal is transferred, and a target gene deeply involved in various types of biological phenomena that are induced by IL-6 is activated by the signal.

For the activation of an acquired immune system, IL-6 signal induces Th17 cells, in cooperation with TGF-β signal. Severe asthma shows a symptom that is resistant to steroids, and significant infiltration of neutrophils is shown in the inflammatory site. However, since significantly high value of IL-17 is detected from blood serum of a patient having severe asthma who has resistance to steroids, it is recently found that severe asthma is caused by an excessive response by Th17 cells.

Furthermore, IL-13, TNF (in particular, TNF-α), and G-CSF are also known to be involved in a progress of asthma (e.g., Non-Patent Document 4).

As an inflammatory cytokine, IL-13 is known to play a role of enhancing further the allergic inflammation in peripheral tissues, and, in addition to the aspect that it promotes an allergic response as a main cause of allergic asthma, it is also known to be involved in intractability of asthma for which a steroid agent is ineffective.

Furthermore, IL-13 is involved in forming of a syndrome not only in asthma but also in inflammatory bowel disease and atopic dermatitis (e.g., Non-Patent Documents 5 and 6).

TNF (in particular, TNF-α) is a signal factor which induces an inflammatory response, and even though it is a factor that is important in terms of a defense against infection, it is also known to be involved simultaneously in a disorder that is caused by augmented inflammation. Namely, TNF is involved in aggravation of a syndrome in many disorders, and it is known to be involved mainly in a joint disorder (rheumatoid arthritis, psoriatic arthritis, spondyloarthropathy, and ankylosing spondylitis), an inflammatory bowel disease (ulcerative colitis and Crohn's disease), a cancer (ovarian cancer and breast cancer), a mental disorder (depression, bipolar disorder, epilepsy, Alzheimer's disease, Parkinson's disease, and multiple sclerosis), a cardiovascular disorder (heart failure and arteriosclerosis), a respiratory tract disorder (bronchial asthma, chronic bronchitis, chronic obtrusive pulmonary disease, and acute lung injury), type 2 diabetes, a kidney disorder (ischemic renal disorder, rejection after transplantation, and glomerulonephritis), and the like (e.g., Non-Patent Documents 7 and 8).

Furthermore, G-CSF is known to have an activity of promoting granulocyte production and enhancing the function of neutrophils.

Furthermore, CXCL1, CXCL2, and CXCL5 belong to the inflammatory chemokine CXC subfamily. Inflammation signal activates secretion of CXCL1, CXCL2, and CXCL5 from various types of blood cells, fibroblast cells, blood vessel endothelial cells, blood vessel smooth muscle cells, alveolar epithelial cells, or the like (e.g., Non-Patent Documents 9 and 10).

When CXCL1, CXCL2, and CXCL5 are secreted in lung tissues due to an augmentation of excessive inflammation in airway mucous membrane, infiltration of neutrophils, which express high-level CXCR2 as a receptor of CXCL1, CXCL2, and CXCL5, is promoted. Consequently, as severe asthma is caused by the infiltration of neutrophils which have resistance to steroids, chronic inflammation inducing irreversible airway remodeling is caused.

Non-Patent Document 1: N Engl J Med, 326(1992), pp. 298-304

Non-Patent Document 2: Clinical and Developmental Immunology Volume 2013(2013), ArticleID609395, 9 pages Non-Patent Document 3: J Asthma. 2008; 45 Suppl 1:41-4.

Non-Patent Document 4: Thorax. 1999 September; 54(9): 825-57.

Non-Patent Document 5: J Allergy (Cairo). 2012; 2012: 316049

Non-Patent Document 6: N Engl J Med 2011; 365:1088-1098

Non-Patent Document 7: J Allergy Clin Immunol. 2008 January; 121(1):5-10

Non-Patent Document 8: J Pathol. 2008 January; 214(2): 149-60.
Non-Patent Document 9: Thorax. 2007 June; 62(6):475-82.
Non-Patent Document 10: Trends Immunol. 2011 October; 32(10):452-60.

DISCLOSURE OF THE INVENTION

Problems to be Solved by the Invention

As described above, in recent years, it became evident that IL-6, IL-13, TNF, G-CSF, CXCL1, CXCL2, or CXCL5 is related with severe diseases.

The present invention is achieved in consideration of the above circumstances, and an object of the invention is to provide a method for screening prophylactic or therapeutic agents for diseases caused by IL-6, IL-13, TNF, G-CSF, CXCL1, CXCL2, or CXCL5 and a prophylactic or therapeutic agent for diseases caused by IL-6, IL-13, TNF, G-CSF, CXCL1, CXCL2, or CXCL5.

Means for Solving the Problems

Inventors of the present invention found that biological phenomena in broad ranges are ruled by the function of MEX3B gene and the MEX3B gene is related with an onset of a disease that is caused by IL-6, IL-13, TNF, G-CSF, CXCL1, CXCL2, or CXCL5, and completed the present invention. Specifically, the present invention is as described below.

The first embodiment of the present invention is
a method for screening prophylactic or therapeutic agents for diseases caused by IL-6, IL-13, TNF, G-CSF, CXCL1, CXCL2, or CXCL5, the method comprising: screening the prophylactic or therapeutic agents using as an index at least one selected from the group consisting of changes in expression of MEX3B gene or MEX3B protein and changes in function of the MEX3B protein.

The second embodiment of the present invention is
a prophylactic or therapeutic agent for diseases caused by IL-6, IL-13, TNF, G-CSF, CXCL1, CXCL2, or CXCL5, comprising a substance for decreasing expression of MEX3B gene or MEX3B protein or a substance for inhibiting the MEX3B protein.

Effects of the Invention

The method for screening prophylactic or therapeutic agents for diseases caused by IL-6, IL-13, TNF, G-CSF, CXCL1, CXCL2, or CXCL5 according to the first embodiment of the present invention allows screening of prophylactic or therapeutic agents for diseases caused by IL-6, IL-13, TNF, G-CSF, CXCL1, CXCL2, or CXCL5.

According to the present invention, a prophylactic or therapeutic agent for diseases caused by IL-6, IL-13, TNF, G-CSF, CXCL1, CXCL2, or CXCL5 can be provided.

BRIEF DESCRIPTION OF THE DRAWINGS

FIG. 7 is a view showing the pathological tissue image of lung tissues in each mouse group.

PREFERRED MODE FOR CARRYING OUT THE INVENTION

Figure 1:
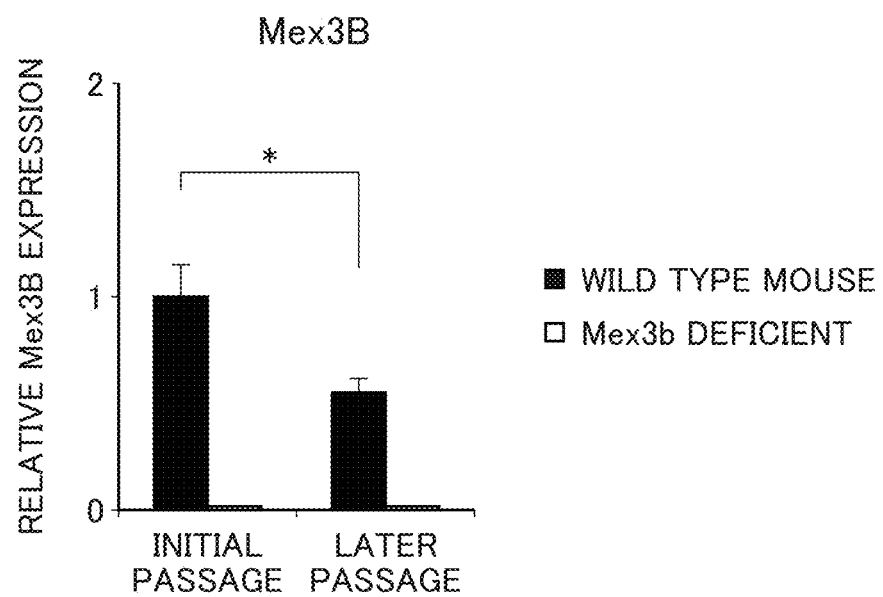
FIG. 1 is a view showing the result of determining the expression level of MEX3B mRNA in embryonic fibroblast cells of wild type BALB/c mouse and MEX3B deficient BALB/c mouse.

Hereinbelow, embodiments of the present invention are described in detail, but, the present invention is not at all limited to the following embodiments, and it can be carried out with suitable modifications within the range of the purpose of the present invention.

<Method for Screening Prophylactic or Therapeutic Agents for Diseases Caused by IL-6, IL-13, TNF, G-CSF, CXCL1, CXCL2, or CXCL5>

With regard to the screening method according to the first embodiment of the present invention, by using as an index at least one selected from the group consisting of changes in expression of the MEX3B gene or MEX3B protein and changes in function of the MEX3B protein, it is possible to screen prophylactic or therapeutic agents for diseases caused by IL-6, IL-13, TNF, G-CSF, CXCL1, CXCL2, or CXCL5.

It is preferable to screen prophylactic or therapeutic agents for diseases caused by IL-6, IL-13, TNF, G-CSF, CXCL1, CXCL2, or CXCL5, and it is more preferable to screen prophylactic or therapeutic agents for diseases caused by IL-6 or CXCL5.

Examples of the function of the MEX3B protein include a function of controlling the function (i.e., translation into protein) of various mRNAs of IL-6, IL-13, TNF, G-CSF, CXCL1, CXCL2, and/or CXCL5 by binding to the mRNAs, and a function of inducing the expression of IL-6, IL-13, TNF, G-CSF, CXCL1, CXCL2, and/or CXCL5. By using as an index at least one selected from the group consisting of the decrease in expression of the MEX3B gene or MEX3B protein and the decrease in function of the MEX3B protein, it is possible to screen prophylactic or therapeutic agents for the diseases caused by an increased expression of IL-6, IL-13, TNF, G-CSF, CXCL1, CXCL2, or CXCL5 (e.g., among severe asthma, rheumatoid arthritis, colitis, Crohn's disease, atopic dermatitis, systemic erythematosus, and cancer, severe asthma, a joint disorder (rheumatoid arthritis, psoriatic arthritis, spondyloarthropathy, and ankylosing spondylitis), diabetes, an inflammatory bowel disorder (ulcerative colitis and Crohn's disease), atopic dermatitis, systemic erythematosus, a cancer (ovary cancer and breast cancer), a mental disorder (depression, bipolar disorder, epilepsy, Alzheimer's disease, Parkinson's disease, and multiple sclerosis), a cardiovascular disorder (heart failure and arteriosclerosis), a respiratory tract disorder (bronchial asthma, chronic bronchitis, chronic obstructive pulmonary disease, and acute lung injury), type 2 diabetes, a kidney disorder (ischemic renal disorder, rejection after organ transplantation, and glomerulonephritis), and the like that are caused by IL-6, IL-13, TNF, G-CSF, CXCL1, CXCL2, or CXCL5 (e.g., Int Immunol. 2015 January; 27 (1): 21-9, Cancer Discov. 2016 January; 6 (1): 80-95)).

Furthermore, level of the decrease is, although it is not particularly limited as long as it is a statistically significant decrease, preferably ½ or less, more preferably ¼ or less, and even more preferably ¹/₁₀ or less compared to the expression or function of the MEX3B gene or MEX3B protein in the absence of a test substance (e.g., system before administration of a test substance (e.g., wild type) or system of negative control (control administered with a substance not affecting the expression or function of the MEX3B gene or MEX3B protein)), and it is particularly preferable that the expression or function is not observed.

By using as an index at least one selected from the group consisting of the increase in expression of the MEX3B gene or MEX3B protein and the increase in function of the MEX3B protein, it is possible to screen prophylactic or therapeutic agents for diseases caused by decreased expression of IL-6, IL-13, TNF, G-CSF, CXCL1, CXCL2, or CXCL5 (e.g., viral infection, bacterial infection or the like (Immunity, 2010 Jul. 23; 33 (1): 106-17)).

Furthermore, the level of the increase is, although it is not particularly limited as long as it is a statistically significant increase, preferably 1.5 times or more, and more preferably 2 times or more compared to the expression or function of the MEX3B gene or MEX3B protein in the absence of a test substance (e.g., system before administration of a test substance or system of negative control).

It is preferable to use as an index at least one selected from the group consisting of the decrease in expression of the MEX3B gene or MEX3B protein and the decrease in function of the MEX3B protein, and it is more preferable to use as an index the decrease in expression of the MEX3B gene.

As long as the above is taken as an index, the method for screening can be any screening method such as in vivo, in vitro, and in silico. As a preferred example of the method for screening, culturing cells expressing the MEX3B gene in the presence and absence of a test substance and screening prophylactic or therapeutic agents for diseases caused by IL-6, IL-13, TNF, G-CSF, CXCL1, CXCL2, or CXCL5 by having as an index the changes in expression of the MEX3B gene or MEX3B protein and the changes in the function of the MEX3B protein in accordance with the presence or absence of the test substance can be mentioned.

As the cells that are used for the screening method according to the first embodiment, fibroblast cells derived from mouse embryo (mouse embryonic fibroblasts (MEF)) are preferable.

The fibroblast cells derived from mouse embryo can induce cell senescence by having simple passage.

The MEF system is one of the methods that are used for determining a change in various biological phenomena accompanied with cell senescence. It is known that inflammatory cytokine or chemokine, which has not been significantly produced at an early passage (e.g., passage 3), is significantly induced in the late passage (e.g., passage 13 to 15). Based on a reconstitution experiment of cell senescence of airway mucosal membrane, relationship between deficiency of the MEX3B gene and changes in production of cytokine and chemokine in MEF cells can be analyzed.

The inventors of the present invention found that, in cells with decreased expression of MEX3B, the secretory factors (IL-6, IL-13, TNF, G-CSF, CXCL1, CXCL2, CXCL5, and the like) may show statistically significant decrease.

As described above, IL-6, IL-13, TNF, G-CSF, CXCL1, CXCL2, and CXCL5 may be deeply involved in the symptoms of severe asthma.

When it the sequence information of the MEX3B gene is used as a base, expression of the MEX3B gene in various human tissues can be detected even in silico. Furthermore, also in vivo and in vitro, by using a probe or a primer which has a partial or whole sequence of the gene, expression of the MEX3B gene in various human tissues can be detected.

Detection of the MEX3B gene expression can be carried out by a common method such as RT-PCR, Northern blot, and Southern blot. Furthermore, measurement of an expression amount of the MEX3B gene at mRNA level can be also carried out by a common method such as RT-PCR, Northern blot, and Southern blot.

In the case of carrying out PCR, the primer is not particularly limited as long as it can specifically amplify the MEX3B gene only, and the primer can be suitably set based on the sequence information of the MEX3B gene. For example, an oligonucleotide that contains at least 10 contiguous nucleotides in the sequence of the MEX3B gene or the expression control region of the gene, and an antisense oligonucleotide having a sequence complementary to the oligonucleotide can be used as a probe or a primer. More specifically, an oligonucleotide which has a sequence of 10 to 60 contiguous residues, and preferably 10 to 40 contiguous residues in the sequence of the MEX3B gene or the expression control region of the gene, and an antisense oligonucleotide having a sequence complementary to the oligonucleotide can be used.

The oligonucleotide and antisense oligonucleotide can be produced by a common method using a DNA synthesizer. Examples of the oligonucleotide or antisense oligonucleotide include, in a partial sequence of mRNA aimed to be detected, a sense primer corresponding to the sequence at 5' terminal side, and an antisense primer corresponding to the sequence at 3' terminal side. The sense primer and antisense primer are oligonucleotides, in which each of them has melting temperature (Tm) and base number that never change to an extreme extent, and oligonucleotides with approximately 10 to 60 bases can be mentioned. Oligonucleotides with approximately 10 to 40 bases are preferable. Furthermore, in the present invention, it is also possible to use derivatives of the aforementioned oligonucleotide, and a methylated product or a phosphorothioated product of the oligonucleotide can be also used, for example.

Furthermore, measurement of an expression amount at the MEX3B protein level can be carried out by a common immunoassay such as Western blot or ELISA using an antibody to be described later. Specifically, the measurement can be carried out by a common method that is known to a person skilled in the pertinent art like those described in the second edition of Molecular Cloning or Current Protocols in Molecular Biology, or the like.

Furthermore, analysis of the changes in function of the MEX3B protein can be carried out by measurement of the presence or absence, or the level of the binding property of the MEX3B protein to mRNA, measurement of the presence or absence, or the level of the expression of the function of mRNA to which the MEX3B protein binds, or measurement of the presence or absence, or the level of the expression of IL-6, IL-13, TNF, G-CSF, CXCL1, CXCL2, and/or CXCL5.

Measurement of the presence or absence, or the level of the binding property of the MEX3B protein to mRNA can be carried out by any analysis such as competitive inhibition test.

Protein-level expression amount measurement of the presence or absence, or the degree of the exertion of the function of mRNA to which the MEX3B protein binds can be carried out by a common immunoassay such as Western blot or ELISA.

mRNA-level measurement of the expression amount of IL-6, IL-13, TNF, G-CSF, CXCL1, CXCL2, and/or CXCL5 expression can be carried out by a common method such as Northern blot, Southern blot, and RT-PCR. Specifically, the measurement can be carried out by a common method that is known to a person skilled in the pertinent art such as those described in the second edition of Molecular Cloning or Current Protocols in Molecular Biology.

As the test substance to be provided to the screening method according to the first embodiment of the present invention, any substance can be used. Type of the test substance is not particularly limited, and it can be a nucleic acid molecule, an antibody, an individual low-molecular synthetic compound, a compound present in an extract of a natural product, or a synthetic peptide. It can be also an artificial nuclease for genome editing to be described later. Alternatively, the test compound can be also a compound library, a phage display library, or a combinatorial library. Construction of a compound library is known to a person skilled in the pertinent art, and a commercially available compound library can be also used. The test substance is preferably a low-molecular compound (e.g., compound library), a nucleic acid molecule, an artificial nuclease for genome editing, or an antibody, and from the viewpoint of having high specificity to the MEX3B gene or protein, a nucleic acid molecule or an antibody is more preferable, and a nucleic acid molecule which has a sequence complementary to an oligonucleotide contained in the MEX3B gene (coding region (CDS) or untranslated region (UTR) in exon, or intron) or in the expression control region of the gene, or an aptamer or an antibody selectively binding to the MEX3B protein is even more preferable.

(MEX3B Gene)

The MEX3B gene includes exon 1, intron, and exon 2, and this constitution is highly preserved in human, mouse, and other mammals. Furthermore, a CDS and an UTR are included in exon 1 and exon 2.

As an untranslated region (UTR) in an exon which does not encode any amino acid, 5'UTR is present upstream of the initiation codon and 3'UTR is present downstream of the termination codon.

Human MEX3B gene encoding the mRNA of human MEX3B has a sequence represented by SEQ ID NO: 1 that is described later.

In SEQ ID NO: 1, the sequence from 437 to 2146 positions corresponds to CDS, the sequence from 1 to 436 positions corresponds to 5'UTR, and the base sequence from 2147 to 3532 positions corresponds to 3'UTR.

SEQ ID NO: 2 to be described later represents a sequence of about 36 kilo bases including the expression control region upstream of the transcription initiation point of the human MEX3B gene. SEQ ID NO: 3 to be described later represents 836 bases in an intron region of the human MEX3B gene. In the human MEX3B gene, this intron region is present between the base at 694 position and the base at 695 position in the sequence represented by SEQ ID NO: 1.

SEQ ID NO: 15 represents the sequence encoding a pre-mRNA of the human MEX3B before splicing. In the sequence encoding a pre-mRNA of the human MEX3B that is represented by SEQ ID NO: 15, the sequences from 437 to 692 positions and 1529 to 2982 positions correspond to CDS, the sequence from 1 to 436 positions corresponds to 5'UTR, the sequence from 2983 to 4368 positions corresponds to 3'UTR, and the region from 693 to 1528 positions corresponds to the intron region of the human MEX3B gene that is represented by SEQ ID NO: 3.

Mouse MEX3B gene encoding the mRNA of mouse MEX3B has a sequence represented by SEQ ID NO: 4 that is described later.

In SEQ ID NO: 4, the sequence from 319 to 2049 positions corresponds to CDS, the sequence from 1 to 318 positions corresponds to 5'UTR, and the sequence from 2050 to 3416 positions corresponds to 3'UTR.

Furthermore, all genes encoding the MEX3B protein (e.g., protein having an amino acid sequence represented by SEQ ID NO: 5 or 6 that is described later) belong to the MEX3B gene. The MEX3B gene has been originally identified as a gene activated by TGF-β, and, based on the analyses thereafter, the MEX3B protein is known as a molecule which binds to various types of mRNA and controls the function (i.e., translation into protein) of those mRNAs (e.g., Nucleic Acids Res. 2007; 35 (4): 1289-300).

Specific examples of the MEX3B gene include a gene described in any one of the following (a) and (b), and, from the viewpoint of screening prophylactic or therapeutic agents for human diseases and also from the viewpoint that it is not needed to carry out unnecessary transformation or the like since as a gene derived from human can be directly used, the gene of the following (a) is preferable.

(a) Gene consisting of the sequence described in SEQ ID NO: 1 or 4 of the Sequence Listing, (b) Gene that is consisting of a sequence resulting from deletion, substitution, and/or addition of one or several bases of the sequence described in SEQ ID NO: 1 or 4 of the Sequence Listing, and also encoding a protein which has an activity of inducing expression of a gene activated by TGF-β or a gene having an activity of inducing the expression of IL-6, IL-13, TNF, G-CSF, CXCL1, CXCL2, and/or CXCL5.

The range of "one or several" in the "sequence resulting from deletion, substitution, and/or addition of one or several bases of the sequence" described in the present specification is not particularly limited. However, it preferably means approximately 1 to 20, more preferably 1 to 10, and even more preferably 1 to 5.

As the degree of the DNA variation described above, those having homology of 80% or more with the sequence of the MEX3B gene described in SEQ ID NO: 1 or 4 of the Sequence Listing can be mentioned, for example, and preferably a DNA having homology of 85% or more, more preferably a DNA having homology of 90% or more, even more preferably a DNA having homology of 95% or more, and particularly preferably a DNA having homology of 98% or more can be mentioned.

(Obtainment of MEX3B Gene)

Method for obtaining the MEX3B gene is not particularly limited. By preparing a suitable probe or primer based on the information of the nucleotide sequence and amino acid sequence that are described in SEQ ID NOs: 1, 4, or 15 and 5 or 6 of the Sequence Listing of the present specification and selecting a desired clone from human cDNA library (i.e., library prepared by a common method from suitable cells in which the MEX3B gene is expressed) by using them, the MEX3B gene can be isolated.

The MEX3B gene can be obtained also by a PCR method. For example, by using a chromosomal DNA originating from human culture cells or cDNA library as a template and a pair of primers designed to amplify the sequence described in SEQ ID NO: 1 or 4, PCR is carried out.

The reaction condition for PCR can be suitably set, and a condition in which a reaction process consisting of 30 seconds at 94° C. (denaturation), 30 seconds to 1 minute at 55° C. (annealing), and 2 minutes at 72° C. (elongation) is taken as 1 cycle, for example, and, after performing 30 cycles, the reaction is allowed to occur for 7 minutes at 72° C., for example, can be mentioned. Subsequently, an amplified DNA fragment can be cloned in a suitable vector which can be amplified in a host such as E. coli. Operations including production of the probe or primer, construction of a cDNA library, screening of a cDNA library, and cloning of a target gene or the like are known to a person who is skilled in the pertinent art, and they can be carried out according to a method described in the second edition of Molecular Cloning or Current Protocols in Molecular Biology, or the like.

The gene (mutated gene) that is consisting of a sequence resulting from deletion, substitution, and/or addition of one or several bases of the sequence described in SEQ ID NO: 1 or 4 of the Sequence Listing in the present specification, and also encoding a protein which has an activity of inducing the expression of a gene activated by TGF-β or a gene having an activity of inducing and regulating the expression of IL-6, IL-13, TNF, G-CSF, CXCL1, CXCL2, and/or CXCL5 can be also produced by any method that is known to a person who is skilled in the pertinent art such as chemical synthesis, genetic engineering techniques, or mutagenesis. For example, by using a DNA having the sequence described in SEQ ID NO: 1 and introducing a mutation to the DNA, a mutated DNA can be obtained. Specifically, it can be carried out by using, for a DNA having the sequence described in SEQ ID NO: 1 or 4, a method of bringing the DNA into contact with a chemical agent as a mutagen for chemical action, a method of irradiating UV light, genetic engineering techniques, or the like. Site directed mutagenesis, which is one of the genetic engineering techniques, is useful in that it is a method allowing introduction of a specific mutation to a specific site, and it can be carried out according to a method described in the second edition of Molecular Cloning or Current Protocols in Molecular Biology, or the like.

As described above, even if the DNA sequence is partially changed due to various artificial treatments of the sequence of the MEX3B gene described in SEQ ID NO: 1 or 4 of the Sequence Listing including introduction of site directed mutagenesis, random mutation caused by treatment with a mutating agent, and mutation, deletion, ligation or the like of a DNA fragment caused by cut of restriction enzyme, the DNA sequence is within the scope of the MEX3B gene regardless of a difference from the DNA sequence described in SEQ ID NO: 1 or 4 as long as the DNA mutant is a DNA which encodes a protein activated by TGF-β, or a protein having an activity of inducing the expression of IL-6, IL-13, TNF, G-CSF, CXCL1, CXCL2, and/or CXCL5.

(Mex3B Protein)

The MEX3B protein is any one of the followings.
(a) Protein consisting of the amino acid sequence described in SEQ ID NO: 5 or 6 of the Sequence Listing,
(b) Protein consisting of an amino acid sequence resulting from deletion, substitution, and/or addition of one or several amino acids of the amino acid sequence described in SEQ ID NO: 5 or 6 of the Sequence Listing, and having a binding activity for a specific mRNA or having an activity of inducing or controlling the expression of IL-6, IL-13, TNF, G-CSF, CXCL1, CXCL2, and/or CXCL5, or (c) Protein consisting of an amino acid sequence which has homology of 95% or more with the amino acid sequence described in SEQ ID NO: 5 or 6 of the Sequence Listing and also being activated by TGF-β or having an activity of inducing or controlling the expression of IL-6, IL-13, TNF, G-CSF, CXCL1, CXCL2, and/or CXCL5.

From the viewpoint of screening prophylactic or therapeutic agents for human diseases and also from the viewpoint that it is not needed to carry out unnecessary transformation or the like since a protein originating from human can be directly used, the protein of the above (a) is preferable.

SEQ ID NO: 5 represents the amino acid sequence of human MEX3B protein. SEQ ID NO: 6 represents the amino acid sequence of mouse MEX3B protein.

The range of "one or several" in the "amino acid sequence resulting from deletion, substitution, and/or addition of one or several amino acids of the amino acid sequence" described in the present specification is not particularly limited. However, it preferably means approximately 1 to 10, more preferably 1 to 5, and even more preferably 1 to 3. The "amino acid sequence having homology of 95% or more" described in the present specification means that the amino acid homology is 95% or more, and the homology is preferably 96% or more, and more preferably 97% or more.

As described in the above, a physiologically active protein which has a binding activity for a specific mRNA and a physiologically active protein having an activity of inducing or controlling the expression of IL-6, IL-13, TNF, G-CSF, CXCL1, CXCL2, and/or CXCL5, both as a protein encoded by a mutant gene which has high homology with the gene having sequence described in SEQ ID NO: 1 or 4 of the Sequence Listing, are all within the scope of the present invention.

Side chains of the amino acid as a constitutional element of a protein may be individually different in terms of the hydrophobicity, charge, size, or the like. However, from the aspect that no substantial influence is exhibited on the three-dimensional structure of a whole protein (also referred to as a stereo structure), several relationships having high conservancy are known either by experience or by actual physical and chemical measurements. For example, for substitution of an amino acid residue, glycine (Gly) and proline (Pro), Gly and alanine (Ala) or valine (Val), leucine (Leu) and isoleucine (Ile), glutamic acid (Glu) and glutamine (Gln), asparaginic acid (Asp) and asparagine (Asn), cysteine (Cys) and threonine (Thr), Thr and serine (Ser) or Ala, lysine (Lys) and arginine (Arg) or the like can be mentioned.

Thus, even mutated proteins resulting from deletion, addition, substitution, or the like on the amino acid sequence of the MEX3B that is described in SEQ ID NO: 5 or 6 of the Sequence Listing are all within the scope of the MEX3B when the mutation is a mutation which is highly conserved in terms of the three-dimensional structure of the MEX3B and when the mutated protein is a physiologically active protein having a binding activity for a specific mRNA or a physiologically active protein having an activity of inducing or controlling the expression of IL-6 and/or CXCL5 similar to the MEX3B.

Method for obtaining the MEX3B protein is not particularly limited, and it may be a protein synthesized by chemical synthesis, a protein derived from nature which has been isolated from a biological sample or cultured cells or the like, or a recombinant protein prepared by genetic engineering techniques.

<Prophylactic or Therapeutic Agent for Diseases Caused by IL-6, IL-13, TNF, G-CSF, CXCL1, CXCL2, or CXCL5>

The prophylactic or therapeutic agent for diseases caused by IL-6, IL-13, TNF, G-CSF, CXCL1, CXCL2, or CXCL5 according to the second embodiment (hereinbelow, also simply referred to as an "prophylactic or therapeutic agent according to the second embodiment") comprises a substance for decreasing the expression of the MEX3B gene or the MEX3B protein, or a substance for inhibiting the MEX3B protein.

The prophylactic or therapeutic agent according to the second embodiment is preferably a prophylactic or therapeutic agent for diseases caused by IL-6, IL-13, TNF, G-CSF, CXCL1, CXCL2, or CXCL5, and it is more preferably a prophylactic or therapeutic agent for diseases caused by IL-6 or CXCL5.

(Antisense Oligonucleotide)

As the substance for decreasing the expression of the MEX3B gene or the MEX3B protein, the aforementioned antisense oligonucleotide, which has a sequence complementary to an oligonucleotide contained in the MEX3B gene (CDS or UTR in exon, or intron) or in a region for controlling the expression of the same gene, can be mentioned.

Introduction of the antisense oligonucleotide to cells inhibits transcription or translation of the MEX3B gene so that diseases caused by IL-6, IL-13, TNF, G-CSF, CXCL1, CXCL2, or CXCL5 can be prevented or treated.

For example, as an oligonucleotide contained in the MEX3B gene (CDS or UTR in exon, or intron) or in a region for controlling the expression of the same gene and the antisense oligonucleotide complementary thereto form a hybrid after their introduction to a cell, mRNA of the MEX3B is decomposed by a nuclease (e.g., RNase H) specific to the generated hybrid double strand so that the transcription or translation of the MEX3B gene can be inhibited.

As the antisense oligonucleotide, an antisense oligonucleotide having a sequence complementary to an oligonucleotide that contains at least 10 contiguous nucleotides in the sequence (CDS or UTR in exon, or intron) of the MEX3B gene or in a region for controlling the expression of the same gene is preferable, and an antisense oligonucleotide having a sequence complementary to an oligonucleotide that contains at least 11 nucleotides is more preferable, an antisense oligonucleotide having a sequence complementary to an oligonucleotide that contains at least 12 nucleotides is even more preferable, an antisense oligonucleotide having a sequence complementary to an oligonucleotide that contains at least 13 nucleotides is particularly preferable, and an antisense oligonucleotide having a sequence complementary to an oligonucleotide that contains at least 14 nucleotides is most preferable.

Furthermore, with regard to the upper limit value of the length of the antisense oligonucleotide, an antisense oligonucleotide having, in the sequence (CDS or UTR in exon, or intron) of the MEX3B gene or in a region for controlling the expression of the same gene, a sequence complementary to an oligonucleotide with 40 or less contiguous nucleotides is preferable, an antisense oligonucleotide having a sequence complementary to an oligonucleotide with 30 or less contiguous nucleotides is more preferable, an antisense oligonucleotide having a sequence complementary to an oligonucleotide with 25 or less contiguous nucleotides is even more preferable, an antisense oligonucleotide having a sequence complementary to an oligonucleotide with 20 or less contiguous nucleotides is particularly preferable, and an antisense oligonucleotide having a sequence complementary to an oligonucleotide with 17 or less contiguous nucleotides is most preferable.

The antisense oligonucleotide is preferably an antisense oligonucleotide which contains at least one nucleotide having at least one structure that is selected from the group consisting of a phosphorothioate structure, a crosslinked structure, and an alkoxy structure.

For example, as the phosphodiester bonding part connecting nucleotides has a phosphorothioate structure, resistance to nuclease can be obtained, and, from the viewpoint that the hydrophobicity is enhanced, incorporation to inside of a cell or a nucleus can be also enhanced.

Furthermore, as the sugar part of a nucleotide has a crosslinked structure such as 2',4'-BNA (2',4'-Bridged Nucleic Acid; other name—Locked Nucleic Acid (LNA)) and ENA (2'-0,4'-C-Ethylene-bridged Nucleic Acid), or an alkoxy structure such as 2'-O-methylaion and 2'-O-methoxyethylation (2'-MOE), the resistance to nuclease can be obtained and also the binding property of mRNA can be enhanced.

With regard to the antisense oligonucleotide, it is preferable that at least one phosphodiester bonding part connecting nucleotides has a phosphorothioate structure, it is more preferable that 50% or more of the phosphodiester bond in the antisense oligonucleotide has a phosphorothioate structure, it is even more preferable that 70% or more of the phosphodiester bond in the antisense oligonucleotide has a phosphorothioate structure, it is particularly preferable that 90% or more of the phosphodiester bond in the antisense oligonucleotide has a phosphorothioate structure, and it is most preferable that all of the phosphodiester bonds in the antisense oligonucleotide have a phosphorothioate structure.

With regard to the antisense oligonucleotide, it is preferable that at least any one terminal nucleotide has a crosslinked structure or an alkoxy structure, it is more preferable that the nucleotides at both terminals of the antisense oligonucleotide have a crosslinked structure or an alkoxy structure (i.e., so-called gapmer type antisense oligonucleotide), it is even more preferable that, in both terminals of the antisense oligonucleotide, up to 4 bases from the terminal independently have a crosslinked structure or an alkoxy structure, and it is particularly preferable that 2 or 3 bases from the terminal have a crosslinked structure or an alkoxy structure.

As one embodiment of the method for introducing the antisense oligonucleotide to cells, an embodiment in which insertion to a suitable vector is made and further introduction to a suitable host cell is carried out can be mentioned.

Type of the suitable vector is not particularly limited, and it can be a self-replicating vector (e.g., plasmid or the like), for example. However, it is preferably a vector that is incorporated into a genome of a host cell upon introduction to a host cell and replicated with a chromosome to which it has been incorporated.

As the suitable vector, a plasmid derived from *E. coli* (e.g., pBR322, pUC118, and the like), a plasmid derived from *Bacillus subtilis* (e.g., pUB110, pSH19, and the like), and also bacteriophage or an animal virus such as retrovirus or vaccinia virus can be used. During recombination, it is also possible to add a translation initiation codon or a translation termination codon by using a suitable synthetic DNA adaptor.

Furthermore, if necessary, the antisense oligonucleotide can be also functionally bonded to a suitable terminator such as a human growth hormone terminator, or, for a fungal host, a TPI1 terminator or an ADH3 terminator, for example. The recombination vector may also have an element such as polyadenylation signal (e.g., those derived from SV40 or adenovirus 5E1b region), a transcription enhancer sequence (e.g., SV40 enhancer), and a translation enhancer sequence (e.g., those encoding adenovirus VARNA). The recombination vector may also be provided with a DNA sequence which enables replication of the vector in a host cell, and examples thereof include SV40 replication origin (when the host cell is a mammalian cell). The recombination vector may also include a selection marker. Examples of the selection marker include a gene of which complement is deficient in a host cell such as dihydrofolate reductase (DHFR) or *Schizosaccharomyces pombe* TPI gene, or a gene resistant to pharmaceuticals such as ampicillin, kanamycin, tetracycline, chloramphenicol, neomycin, or hygromycin, for example.

Examples of a host cell to which the antisense oligonucleotide or a vector containing it include a higher eukaryotic cell, a bacterium, a yeast, and a fungus, but it is preferably a mammalian cell.

Examples of the mammalian cell include HEK293 cell, HeLa cell, COS cell (e.g., COS-7 cell and the like), BHK cell, CHL cell or CHO cell, BALB/c mouse cell (e.g., BALB/c mouse embryonic fibroblast cell), and the like. A method of transforming a mammalian cell and expressing a gene introduced to the cell is also known, and a lipofection method, an electroporation method, a calcium phosphate method, and the like can be used, for example.

The prophylactic or therapeutic agents according to the second embodiment may additionally contain a carrier for lipofection from the viewpoint of enhancing the incorporation to a cell, but it is also possible not to contain any carrier.

Examples of the carrier for lipofection include a carrier which has high affinity to cell membrane (e.g., liposome or cholesterol), and it is preferably lipofectamine or lipofectin, and more preferably lipofectamine.

For example, as the expression of the MEX3B gene is inhibited by introducing the antisense oligonucleotide together with a carrier for lipofection to cells of a patient by administering, via injection or the like, to a lesion or whole body of a patient, diseases caused by IL-6, IL-13, TNF, G-CSF, CXCL1, CXCL2, or CXCL5 can be either prevented or treated.

Furthermore, as the antisense oligonucleotide has at least one structure that is selected from the group consisting of a phosphorothioate structure, a crosslinked structure, and an alkoxy structure and it is used in combination with a carrier for lipofection, incorporation to a cell or a nucleus of a patient can be further enhanced.

The administration amount of the antisense oligonucleotide as an effective component is, for single administration, generally within a range approximately 0.1 µg to 100 mg per kg of bodyweight.

(siRNA)

As a substance for decreasing the expression of the MEX3B gene or MEX3B protein, a double-stranded RNA (small interfering RNA (siRNA)) containing at least 20 contiguous nucleotides in a CDS or an UTR of the sequence of an RNA to be transcribed from the sequence of the MEX3B gene, or a DNA encoding the double-stranded RNA can be also mentioned. A double-stranded RNA containing at least 21 contiguous nucleotides in a CDS or an UTR of the sequence of an RNA to be transcribed from the sequence of the MEX3B gene, or a DNA encoding that double-stranded RNA is preferable. A double-stranded RNA containing 30 or less contiguous nucleotides in a CDS or an UTR of the sequence of an RNA to be transcribed from the sequence of the MEX3B gene, or a DNA encoding that double-stranded RNA is preferable, and a double-stranded RNA containing 25 or less contiguous nucleotides in a CDS or an UTR of the sequence of an RNA to be transcribed from the sequence of the MEX3B gene, or a DNA encoding the double-stranded RNA is more preferable.

RNA interference (RNAi) indicates a phenomenon showing inhibited expression of a target gene when an RNA (double-stranded RNA: dsRNA) in which part of mRNA encoding a part of a certain target gene is prepared as a double strand is introduced to a cell. Examples of the DNA encoding a double-stranded RNA include a DNA having a reverse-direction repeating a sequence of the MEX3B or a partial sequence thereof. By introducing a DNA having a reverse-direction repeating sequence to cells of mammals, the reverse-direction repeating sequence of a target gene can be expressed in a cell, and, accordingly, it becomes possible to inhibit the expression of the target gene (MEX3B) based on the RNAi effect. The reverse-direction repeating sequence indicates a sequence in which a target gene and a sequence in the reverse reaction thereof are present in parallel via a suitable sequence. Specifically, for a case in which a target gene has a double-strand consisting of n nucreotide sequences shown below,

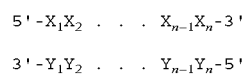

the reverse-direction sequence thereof has a sequence shown below.

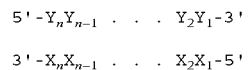

(herein, with regard to the bases represented by X and the bases represented by Y, those having the same subscript are the bases that are complementary to each other).

The reverse-direction repeating sequence is a sequence in which the above two types of sequence are present via a suitable sequence. As the reverse-direction repeating sequence, a sequence having a target gene upstream of the reverse-direction sequence and a sequence having a reverse-direction sequence upstream of a target gene sequence are considered. The reverse-direction repeating sequence used in the present invention can be any one of them, but it is preferable that the reverse-direction sequence is present upstream of a target gene sequence. The sequence present between a target gene sequence and a reverse-direction sequence thereof is a region in which a hairpin loop is formed when transcription into an RNA is made (shRNA: small hairpin RNA). Length of this region is not particularly limited as long as a hairpin loop can be formed, but it is preferable to be approximately 0 to 300 bp, and more preferable to be approximately 0 to 100 bp. It is also possible that a restriction enzyme site is present in that sequence.

According to the present invention, by incorporating a reverse-direction repeating sequence of a target gene to a downstream of a sequence of a promoter which is operable in mammals, the reverse-direction repeating sequence of a target gene can be expressed in cells of mammals. A sequence of a promoter used in the present invention is not particularly limited as long as it is operable in mammals.

For example, when the double-stranded RNA or DNA are administered via injection or the like, together with a carrier for lipofection used for facilitating the incorporation to cells, to a lesion or whole body of a patient followed by incorporation to cells of a patient, severe asthma can be inhibited. The administration amount of the double-stranded RNA or DNA as an effective component is, for single administration, generally within a range approximately 0.1 µg to 10 mg per kg of bodyweight.

(Artificial Nuclease)

The substance for decreasing the expression of the MEX3B gene or MEX3B protein may be an artificial nuclease for genome editing such as Clusterd Regularly Interspaced Short Palindromic Repeats (CRISPR)/Cas nuclease, and an artificial restriction enzyme (artificial nuclease) using Transcription Activator-Like Effector Nuclease (TALEN) and zinc finger nuclease (ZFN). TALEN is an artificial nuclease including TALEs, i.e., domain formed by polymerization of four types of units which recognize and bind any one of four types of bases (A, T, G, and C), and TALEs recognizes at least a partial sequence of the MEX3B gene and binds thereto.

ZFN is an artificial nuclease in the form of a chimeric protein which includes a zinc finger domain and a DNase domain. The zinc finger domain has a structure in which plural units of a zinc finger, which recognizes specific 3-nucleotides, are polymerized, and it is a domain recognizing and binding a DNA sequence with a multiple of three for binding, and the zinc finger domain recognizes at least a partial sequence of the MEX3B gene and binds thereto.

CRISPR/Cas nuclease includes a guide RNA and Cas nuclease (preferably, Cas9).

The guide RNA means an RNA which binds to Cas nuclease as a DNA digesting enzyme and has a function of guiding Cas nuclease to a target DNA (at least a partial sequence of the MEX3B gene). The guide RNA has, on its 5' terminal, a sequence complementary to a target DNA (at least a partial sequence of the MEX3B gene), and when the guide RNA binds to a target DNA via the complementary sequence, the guide RNA guides Cas nuclease to a target DNA. Cas nuclease functions as a DNA endonuclease, cuts off a DNA at a site in which a target DNA is present, and can specifically reduce the expression of the MEX3B gene, for example.

At least a partial sequence of the MEX3B gene as a target preferably has 15 to 25 bases, more preferably 17 to 22 bases, even more preferably 18 to 21 bases, and particularly preferably 20 bases.

As a eukaryotic cell or a eukaryotic organism carrying the MEX3B gene is transfected with a composition which contains a guide RNA specific to the MEX3B gene or a DNA encoding the guide RNA, and a nucleic acid encoding Cas nuclease or Cas nuclease, the expression of the MEX3B gene can be reduced.

The nucleic acid encoding Cas nuclease or Cas nuclease, and the guide RNA or DNA encoding the guide RNA can be introduced to inside of cells by various methods that are known in the field of the pertinent art, for example, microinjection, electroporation, DEAE-dextran treatment, lipofection, nano particle-mediated transfection, protein transduction domain-mediated transduction, virus-mediated gene transfer, PEG-mediated transfection of protoplast, or the like, but it is not limited thereto. Furthermore, the nucleic acid encoding Cas nuclease or Cas nuclease, and the guide RNA can be incorporated to the inside of a biological organism by various methods for administering a gene or a protein that are known in the field of the pertinent art, for example, injection or the like. The nucleic acid encoding Cas nuclease or Cas protein can be incorporated to inside of cells, either in the form of a complex with guide RNA or individually. Cas nuclease fused to a protein transduction domain such as Tat can be also delivered to the inside of cells. Preferably, a eukaryotic cell or a eukaryotic organism is simultaneously transfected or contiguously transfected with Cas9 nuclease and a guide RNA. Contiguous transfection can be carried out by a first transfection using a nucleic acid encoding Cas nuclease and subsequently a second transfection using a naked guide RNA. Preferably, the second transfection is 3, 6, 12, 18, 24 hours later, but it is not limited thereto. Expression of a guide RNA can be also carried out by using a unit for expressing guide RNA. The unit for expressing guide RNA is preferably a CRISPR-Cas9 based transcription unit which includes a target sequence (i.e., a partial sequence of the MEX3B gene) and a guide RNA, and those having a promoter region for expressing the guide RNA (promoter of RNA polymerase III (e.g., promoter selected from U6 promoter and H1 promoter)), target sequence (i.e., the MEX3B gene), and a guide RNA are preferable, and those in which the promoter, a sequence complementary to a target sequence (i.e., at least a partial sequence of the MEX3B gene), and a guide RNA are connected in a seamless manner are more preferable. As the CRISPR/Cas nuclease, a Cas9 mutant which cuts off, as a nickase, only one strand of a double-stranded DNA in order to prevent the off-target may be used. Examples of a single-stranded restriction type Cas9 mutant include Cas9 (D10A). When a guide RNA which has a target sequence complementary to one strand of a target DNA and a guide RNA which has a target sequence complementary to the other strand extremely close to that one strand are used in combination, for example, the single-stranded restriction type Cas9 mutant can cut off that one strand with specificity of 20 bases while further cutting off the other strand with specificity of 20 bases so as to cut off a DNA with specificity of 40 bases. Accordingly, it becomes possible to enhance remarkably the target specificity.

The administration amount of the artificial nuclease or the nucleic acid encoding the artificial nuclease as an effective component is, for single administration, generally within a range approximately 0.1 µg to 10 mg per kg of bodyweight.

The prophylactic or therapeutic agent for diseases caused by IL-6, IL-13, TNF, G-CSF, CXCL1, CXCL2, or CXCL5 according to the second embodiment can be administered systemically or topically, either orally or parenterally. Examples of a method for parenteral administration include intravenous injection such as dropping addition, intramuscular injection, intraperitoneal injection, and subcutaneous injection. The administration method can be suitably selected depending on age and symptom of a patient. The administration amount varies depending on age, administration route, and the number of administrations, and it can be suitably selected by a person who is skilled in the pertinent art. Examples of the preparation form suitable for parenteral administration include those containing additives such as stabilizing agent, buffering agent, preservative, isotonic acid, or the like, and those containing a pharmaceutically acceptable carrier or an additional product are also acceptable. Examples of those carrier and additional product include water, an organic solvent, a polymer compound (collagen, polyvinyl alcohol, or the like), stearic acid, human blood serum albumin (HSA), mannitol, sorbitol, lactose, and a surface active agent, but they are not limited thereto.

(Aptamer or Antibody Selectively Binding to MEX3B Protein)

Substance for inhibiting the MEX3B protein can be any substance such as high molecular compound (nucleic acid or the like), antibody, and low molecular compound as long as it can inhibit the function of the MEX3B protein. As one preferred embodiment of the substance for inhibiting the MEX3B protein, a prophylactic or therapeutic agent for diseases caused by IL-6, IL-13, TNF, G-CSF, CXCL1, CXCL2, or CXCL5, in which an aptamer selectively binding to the MEX3B protein is used, can be mentioned. An aptamer indicates a nucleic acid pharmaceutical which consists of a single-stranded RNA or DNA and inhibits the function of a target protein as it binds to the protein based on its steric structure. The aptamer has a high binding property and specificity for a target protein and low immunogenicity, can be produced by chemical synthesis, and has high storage stability. Nucleotide length of an aptamer selectively binding to the MEX3B protein is not particularly limited as long as it can specifically bind to the MEX3B protein. However, it is preferably 15 to 60 bases, more preferably 20 to 50 bases, even more preferably 25 to 47 bases, and particularly preferably 26 to 45 bases. The aptamer selectively binding to the MEX3B protein can be obtained by Systematic Evolution of Ligands by EXponential enrichment (SELEX) method.

As another preferred embodiment of the substance for inhibiting the MEX3B protein, a prophylactic or therapeutic agent for diseases caused by IL-6, IL-13, TNF, G-CSF, CXCL1, CXCL2, or CXCL5, in which an antibody selectively binding to the MEX3B protein is used, can be mentioned. Either a polyclonal antibody or a monoclonal antibody can be used as long as it can specifically bind to the MEX3B protein. The polyclonal antibody can be produced by separating and purifying blood serum that is obtained from an animal immunized with an antigen. The monoclonal antibody can be produced by preparing a hybridoma antibody-generating cells obtained from an animal immunized with an antigen and myeloma cells that are fused to each other, and culturing the hybridoma or causing an animal to have ascites cancer by administering the hybridoma to the animal and separating and purifying the culture medium or mice ascites. The antigen can be produced by purifying the MEX3B protein from various cultured human cells, or by introducing a recombination vector which contains a DNA encoding the amino acid sequence of the MEX3B protein or a mutant sequence thereof or a protein having part of them to a host such as *E. coli*, yeast, animal cells, or insect cells and separating and purifying the protein that is resulting from expression of the DNA. The antigen can be also produced by synthesizing, by using a peptide synthesizer, a peptide having a partial sequence of the amino acid sequence of the MEX3B protein.

With regard to a method for immunization, it is possible to have direct subcutaneous, intravenous, or intraperitoneal administration of an antigen to a non-human mammal such as rabbit, goat, rat, mouse, or hamster, but it is also preferable that the antigen is administered while it is bound to a carrier protein having high antigenicity such as sukashigai hemocyanin, keyhole limpet hemocyanin, bovine serum albumin, or bovine thyroglobulin, or administered with a suitable adjuvant such as Complete Freund's Adjuvant, aluminum hydroxide gel, or pertussis vaccine.

Administration of an antigen can be carried out, after the first administration, 3 to 10 times with an interval of 1 to 2 weeks. Blood is taken from postorbital venous plexus on Day 3 to Day 7 after the each administration, and investigation is made to see whether or not the blood serum reacts with the antigen used for immunization, according to measurement of an antibody titer by enzyme immunoassay or the like. With regard to the antigen that is used for immunization, a non-human mammal having blood serum exhibiting a sufficient antibody titer can be used as a source for supplying blood serum or cells for producing the antibody. The polyclonal antibody can be produced by separating and purifying the blood serum.

The monoclonal antibody can be produced by preparing a hybridoma according to fusion between the antibody-generating cells and myeloma cells derived from non-human mammal, culturing the hybridoma or causing an animal to have ascites cancer by administering the hybridoma to an animal, and separating and purifying the culture liquid or ascites. As the antibody-generating cells, antibody-generating cells in spleen cells, lymph nodes, or peripheral blood can be used, and, particularly preferably, spleen cells can be used.

As the myeloma cells, established cell lines derived from a mouse such as P3-X63Ag8-U1 (P3-U1) strain [Current Topics in Microbiology and Immunology, 18, 1-7 (1978)], P3-NS1/1-Ag41 (NS-1) strain [European J. Immunology, 6, 511-519 (1976)], SP2/0-Ag14 (SP-2) strain [Nature, 276, 269-270 (1978)], P3-X63-Ag8653 (653) strain [J. Immunology, 123, 1548-1550 (1979)], and P3-X63-Ag8 (X63) strain [Nature, 256, 495-497 (1975)], which are myeloma cell lines of 8-azaguanine resistant mouse (derived from (BALB/c), can be used. The hybridoma cells can be produced by the following method. First, antibody-generating cells and myeloma cells are admixed with each other, and, after being suspended in HAT medium [medium obtained by adding hypoxanthine, thymidine, and aminopterin to normal medium], they are cultured for 7 to 14 days. After culture, part of the culture supernatant is collected and reacted with an antigen according to an enzyme immunoassay or the like, and those not reacting with a protein not including the antigen are selected. Subsequently, according to limiting dilution, cloning is carried out and those recognized with high and stable antibody titer by an enzyme immunoassay are selected as hybridoma cells which produce a monoclonal antibody. The monoclonal antibody can be produced by separation or purification from culture obtained by culturing the hybridoma cells or from ascites obtained by intraperitoneal administration of hybridoma cells to an animal to cause the animal to have ascites cancer.

As a method for separating and purifying the polyclonal antibody or monoclonal antibody, a method such as centrifuge, ammonium sulfate precipitation, caprylic acid precipitation, or a method based on chromatography using DEAE-sepharose column, anion exchange column, Protein A or G-column, or gel filtration column or the like may be used, either singly or in combination thereof, can be mentioned.

When an antibody is referred in the present specification, not only a whole-length antibody but also a fragment of an antibody may be referred. The fragment of an antibody is preferably a functional fragment, and examples thereof include F(ab')2 and Fab'. F(ab')2 and Fab' are produced by treating immunoglobulin with a proteinase (e.g., pepsin or papain), and they are an antibody fragment produced by digestion either before and after the disulfide bond present between 2H chains in a hinge region.

When the antibody is used for the purpose of administration to a human, it is preferable to use a humanized type antibody or a humanized antibody in order to reduce the immunogenicity. Those humanized type antibody and humanized antibody can be produced by using mammals such as transgenic mice. The humanized type antibody is described in Morrison, S. L. et al. [Proc. Natl. Acad. Sci. USA, 81: 6851-6855 (1984)] and Hiroshi Noguchi [Journal of Clinical and Experimental Medicine, 167: 457-462 (1993)], for example. A humanized chimeric antibody can be produced by linking the V region of a mouse antibody to the C region of a human antibody by genetic recombination. The humanized antibody can be produced by replacing a region of a mouse monoclonal antibody other than the complementarity determining region (CDR) with a sequence derived from a human antibody.

Furthermore, the antibody can be also used as an immobilized antibody which is immobilized onto an insoluble carrier such as solid phase carrier, or as a labeled antibody which is labeled with a labeling material. Those immobilized antibodies and labeled antibody are also within the scope of the present invention.

Among the antibodies that are described above, the antibody which specifically binds to the MEX3B protein and can inhibit the function of the protein can be used as a prophylactic or therapeutic agent for diseases that are caused by IL-6, IL-13, TNF, G-CSF, CXCL1, CXCL2, or CXCL5.

When the antibody is used in the form of a pharmaceutical composition as a prophylactic or therapeutic agent for diseases that are caused by IL-6, IL-13, TNF, G-CSF, CXCL1, CXCL2, or CXCL5, a pharmaceutical composition can be produced by using the antibody as an effective component and also using a pharmaceutically acceptable carrier, a diluent (e.g., immunogenic adjuvant or the like), a stabilizer, a vehicle, or the like. The prophylactic or therapeutic agent containing an antibody for diseases that are caused by IL-6, IL-13, TNF, G-CSF, CXCL1, CXCL2, or CXCL5 can be formulated, after filtering sterilization and freeze-drying, into administration form in an administration vial or stabilized aqueous preparation. Administration to a patient can be carried out by a method that is known to a person who is skilled in the pertinent art, for example, intraarterial injection, intravenous injection, or subcutaneous injection. The administration amount may vary depending on bodyweight or age of a patient and administration method, but a suitable administration amount can be suitably selected by a person who is skilled in the pertinent art. The administration amount of the antibody as an effective component is, for single administration, generally within a range approximately 0.1 µg to 100 mg per kg of bodyweight.

EXAMPLES

Hereinbelow, the present invention is described in greater detail by showing examples, but the scope of the present invention is not limited to those examples.

Example 1

(Production of MEX3B Deficient (Knock-Out) BALB/c Mouse)

As a genomic DNA of the MEX3B gene, the genomic DNA introduced to BAC clone (RP23-272F$_2$) was used. The targeting vector was constructed in a manner such that a gene cassette in the BAC clone resistant to neomycin is substituted with the DNA region of exon 1 and exon 2 of the MEX3B gene. The construct was introduced by electroporation to BALB/c-derived ES cells (supplied from Dr. Yasui at Osaka University) and selected using an antibiotic (G418). Presence or absence of homologous recombination was analyzed by PCR method, FISH method, and Southern blot, and 4 ES clones were identified. The selected ES cells were injected to blastocyst of a C57BL/6 mouse, and then transplanted in a surrogate parent in order to obtain a chimeric mouse. By cross-breeding the obtained male chimeric mouse with a female BALB/c mouse, $F_1$ mice each having a MEX3B heterogenous mutation were identified by PCR, and, as a result of cross-breeding the mice each other, a homozygote $F_2$ was obtained. Genotype of the $F_2$ mouse was confirmed by PCR.

(Isolation and Subculture of Embryonic Fibroblast Cells)

Trypsin powder (manufactured by GIBCO) was dissolved in PBS (phosphate buffered physiological saline) so as to have a concentration of 0.25% (W/V), and then subjected to filtering sterilization by passing it through a 0.45 micrometer filter (manufactured by Advantec) (prepared at time of use).

13.5 Days after starting the cross-breeding of mouse, the whole body of the female C57BL/6 mouse was subjected to alcohol sterilization using 70% ethanol, and, after opening the abdomen, the uterus containing embryonic mice was collected. After cutting off the portion connected with umbilical cord with scissors, the embryonic animals were taken out one by one from the uterus, and then immersed in PBS. After removing the head, intestines, paws, and tail from the embryonic animal, it was transferred to 1 mL trypsin solution which has been kept on ice, and minced to a size of 2 to 3 mm by using sharp scissors. After transfer to a 15 mL tube, the liquid volume was adjusted to 5 mL per embryonic animal by using the trypsin solution, and then shaken for 10 minute at 37° C., 60 to 100 cycles/minute while monitoring the digestion state. To terminate the trypsin reaction, 1 mL of bovine albumin serum (FBS) was added and suspended well. Further, to remove the cell lumps, the resultant was filtered using a mesh of 100 mm cell strainer (manufactured by Falcon). After centrifuge (280×g, for 5 minutes, 4° C.) of the filtered cell suspension, the supernatant was removed and the obtained precipitates were suspended in a basic medium (DMEM (High Glucose) (Dulbecco's modified Eagle medium: manufactured by NISSUI PHARMACEUTICAL CO., LTD.), 10% FBS, penicillin streptomycin) and the resultant was sown on a 100 mm culture dish, at a ratio of 1 well per embryonic animal. On the next day, the medium exchange was replaced, and embryonic fibroblast cells were used for experiments after a couple of passages using trypsinization.

Each of the embryonic fibroblast cells of the wild type BALB/c mouse and embryonic fibroblast cells of the MEX3B deficient BALB/c mouse was cultured in 35 mm cell culture dish (BD Falcon: 353001) having 5% FBS-containing DMEM (Dulbecco's modified Eagle medium: manufactured by NISSUI PHARMACEUTICAL CO., LTD.), in which 2.5 µg/mL of Fungizone is contained, in a carbonate gas incubator (37° C., 5% CO2 in air), and, after the cells became in confluent state, subculture was carried out.

(Quantitative RT-PCR Test)

For each of the wild type mouse and MEX3B deficient mouse, by using a dissolution buffer TRIsure (manufactured by BIOLINE) for the cells at the early passage (passage 3) and cells at the late passage (passage 13 to 15), total RNA was recovered. By using Primescript (manufactured by Takara Bio Inc.), a reverse transcription reaction was carried out to obtain cDNA. After that, by using Light Cycler 480 (manufactured by ROCHE), quantitative RT-PCR was carried out. The quantitative statistical analysis was carried out by more than 3 independent experiments.

A sequence of the primers used for the quantitative RT-PCR test is as follows.

```
MEX3B
primer Fw1:
                                    (SEQ ID NO: 7)
5'-CGTCGTCCTCTGTGGTCTTTCCCGGGGGTG-3'

MEX3B primer Rv1:
                                    (SEQ ID NO: 8)
5'-TCAGGAAAAAATGCGGATGGCCTGAGTGAC-3'

Mouse GAPDH primer Fw1:
                                    (SEQ ID NO: 9)
5'-AGAGACAGCCGCATCTTCTT-3'

Mouse GAPDH primer Rv1:
                                    (SEQ ID NO: 10)
5'-GACAAGCTTCCCATTCTCGG-3'

Mouse IL-6 primer Fw1:
                                    (SEQ ID NO: 11)
5'-GCTACCAAACTGGATATAATCAGGA-3'

Mouse IL-6 primer Rv1:
                                    (SEQ ID NO: 12)
5'-CCAGGTAGCTATGGTACTCCAGAA-3'

Mouse CXCL5 primer Fw1:
                                    (SEQ ID NO: 13)
5'-CAGAAGGAGGTCTGTCTGGA-3'

Mouse CXCL5 primer Rv1:
                                    (SEQ ID NO: 14)
5'-TGCATTCCGCTTAGCTTTCT-3'
```

FIG. 1 is a view showing the result of determining, by quantitative RT-PCR, the expression level of MEX3B mRNA in embryonic fibroblast cells of the wild type BALB/c mouse and MEX3B deficient BALB/c mouse. FIG. 1 shows a mean value of 6 wild type mice and a mean value of 7 MEX3B deficient mice with p value at significance level (<0.05). Y axis indicates, with regard to the actual data at passage 3 as early passage of each wild type mouse, a relative numerical value when the gene amount of a quantification subject divided by GAPDH amount is set at "1". The same shall apply for FIGS. 2 and 3 that are described below. As it is evident from FIG. 1, as a result of analyzing the cells of the embryonic fibroblast of the wild type mouse and MEX3B deficient mouse at early passage (passage 3) and late passage (passage 13 to 15), it was shown that the all cells derived from MEX3B deficient mouse exhibited no expression of Mex3B, both at early passage and late passage.

Figure 2:
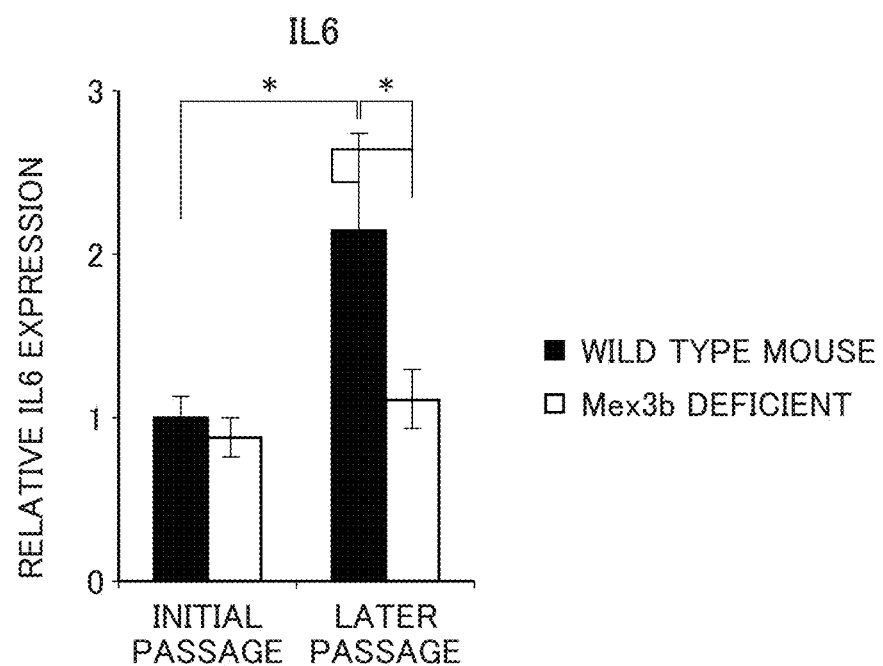
FIG. 2 is a view showing the result of determining the expression level of IL-6 mRNA in embryonic fibroblast cells of wild type BALB/c mouse and MEX3B deficient BALB/c mouse.
Figure 3:
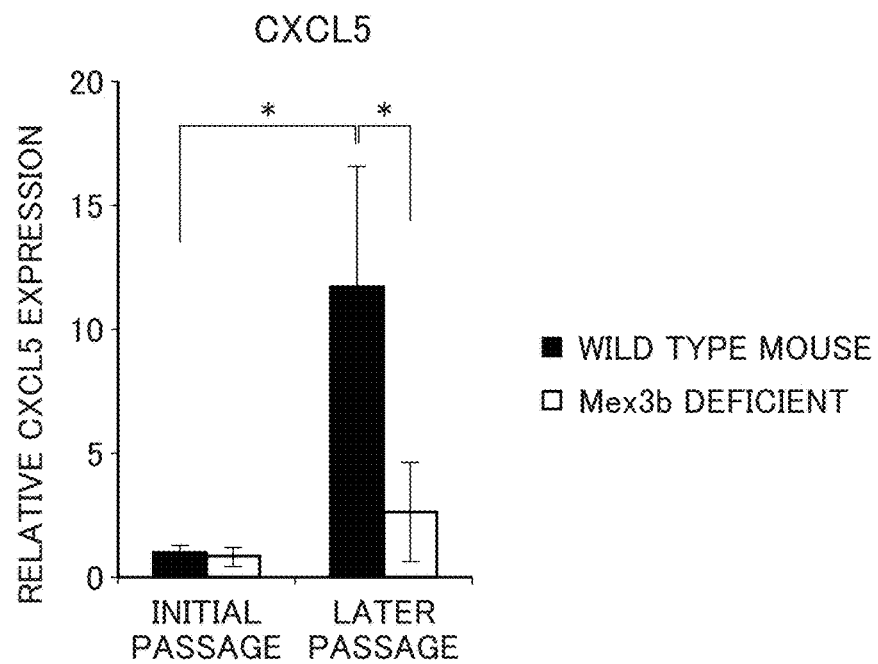
FIG. 3 is a view showing the result of determining the expression level of CXCL5 mRNA in embryonic fibroblast cells of wild type BALB/c mouse and MEX3B deficient BALB/c mouse.

Furthermore, FIG. 2 is a view showing the result of determining, by quantitative RT-PCR, the expression level of IL-6 mRNA in embryonic fibroblast cells of the wild type BALB/c mouse and MEX3B deficient BALB/c mouse. FIG. 3 is a view showing the esu of determining, by quantitative RT-PCR, the expression level of CXCL5 mRNA in embryonic fibroblast cells of the wild type BALB/c mouse and MEX3B deficient BALB/c mouse. As itis evident from FIGS. 2 and 3, as a result of analyzing the cells of the embryonic fibroblast cells of the wild type mouse and MEX3B deficient BALB/c mouse at early passage and late passage, it is shown that, in the case of the cells derived from MEX3B deficient ouse, the expression of IL-6 and CXCL5 is significantlylowered in the cells at late passage.

From the above results in FIGS. 2 and 3 showing that, in the cells that are deficient of Mex3B gene, the expression of IL-6 and CXCL5 is lowered in fibroblast cells that are in the course of aging at late passage, it is demonstrated that the Mex3B certainly regulates IL-6 and CXCL5, and also, when it is seen the other way around, it is demonstrated that an onset or a progress of disorders caused by IL-6 or CXCL5 (e.g., severe asthma) can be inhibited by inhibiting the function of the MEX3B gene product.

(Severe Asthma Inducing Test)

On Day 0, each of the females of 8-week old wild type BALB/c mouse and MEX3B deficient BALB/c mouse was subjected to subcutaneous sensitization with 50 µl of Complete Freund's Adjuvant (CFA: Sigma-Aldrich Company) and 20 µg of egg white albumin (OVA: Sigma-Aldrich Company) emulsified in 50 µl of PBS. On Day 21 and Day 22, all mice were forced to inhale an aerosol which consists of 0.1% OVA in PBS (6 or more mice/group). Furthermore, as a control, inhalation of an aerosol, which consists of PBS, was carried out. On Day 23, the numbers of the various types of immune cells in bronchoalveolar lavage were measured.

Figure 4:
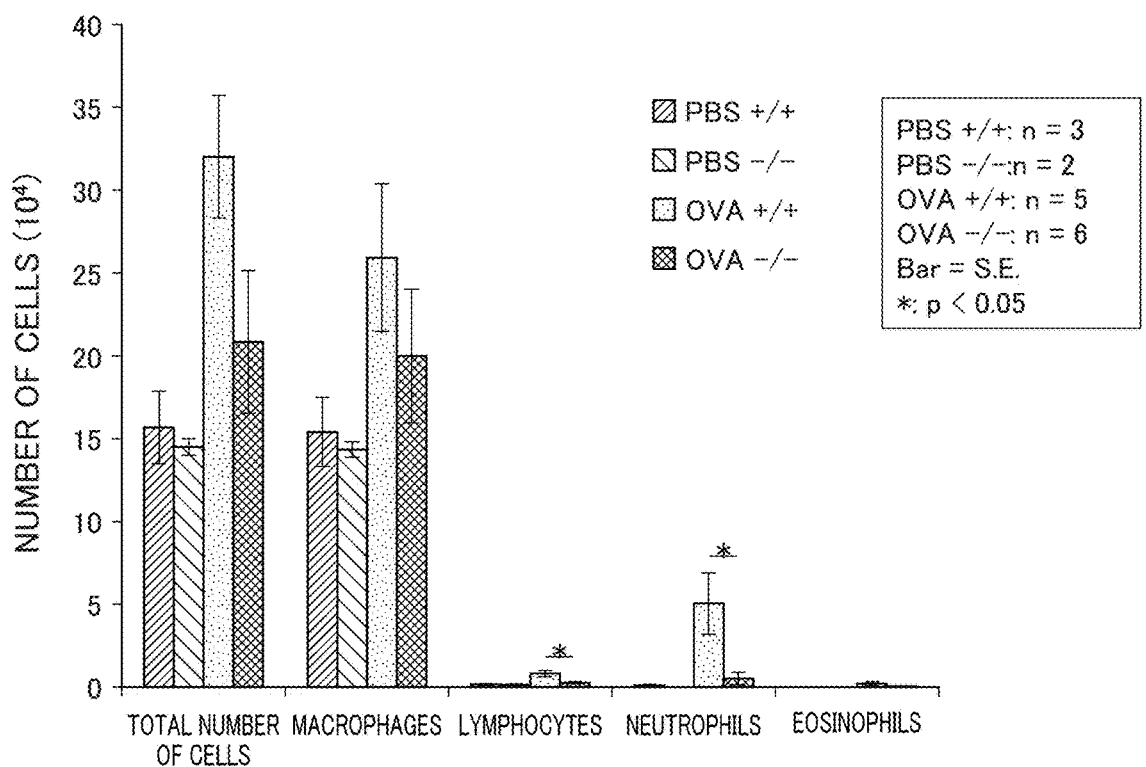
FIG. 4 is a view showing the result of determining an increase in various immune cells of wild type BALB/c mouse and MEX3B deficient BALB/c mouse in asthma inducing test.

FIG. 4 is a view showing the result of determining an increase in various immune cells (macrophage, lymphocyte, neutrophil, and eosinophil) of the wild type BALB/c mouse and MEX3B deficient BALB/c mouse in bronchoalveolar lavage fluid of the severe asthma model. In FIG. 4, PBS+/+ indicates the number of cells in the wild type BALB/c mouse which has inhaled PBS as a control, PBS−/− indicates the number of cells in the MEX3B deficient BALB/c mouse which has inhaled PBS as a control, OVA+/+ indicates the number of cells in the wild type BALB/c mouse which has inhaled OVA, and OVA−/− indicates the number of cells in the MEX3B deficient BALB/c mouse which has inhaled OVA. As it is evident from the results shown in FIG. 4, the wild type BALB/c mouse and MEX3B deficient BALB/c mouse, which have inhaled OVA, all exhibited increased total cell number and increased macrophage number compared to control, and they were sensitized with OVA. Furthermore, as the increased number of neutrophils and the increased number of lymphocytes are shown from the wild type BALB/c mouse which have inhaled OVA, it is demonstrated that severe asthma has been induced. On the contrary, as the number of neutrophils and lymphocytes in the MEX3B deficient BALB/c mouse which have inhaled OVA are decreased and this showed statistical difference, it is demonstrated that symptoms of severe asthma have been ameliorated. From the results that are described above, searching a substance that can inhibit the function of the MEX3B protein (e.g., low molecular compound, protein, nucleic acid or the like) is useful as a method for screening prophylactic or therapeutic agents for diseases that are caused by IL-6, IL-13, TNF, G-CSF, CXCL1, CXCL2, or CXCL5.

Example 2

(Test of Administering Gapmer Type Antisense Oligonucleotide in a Model for Severe Asthma)

On Day 0, 8-week old female wild type BALB/c mice were subjected to subcutaneous sensitization with 50 µl of CFA (manufactured by Sigma-Aldrich Company) and 20 µg of OVA (manufactured by Sigma-Aldrich Company) emulsified in 50 µl of PBS.

For 5 consecutive days starting from Day 16, inhalation administration of a gapmer type antisense oligonucleotide (i.e., 5 ml of 10 µM solution was subjected to prepare aerosol by using nebulizer, and, after filling it in a container, in which mice were exposed to it for 20 minutes) was carried out. As gapmer type antisense oligonucleotides, a control gapmer and a mouse MEX3B specific gapmer were administered by inhalation. Hereinbelow, they are also referred to as "OVA inhale-gapmer (control) inhalation group" and "OVA inhale-MEX3B specific gapmer inhalation group", respectively. As a mouse MEX3B specific gapmer, a gapmer type antisense oligonucleotide (5'-ACATAAACGAGTGGT-3': SEQ ID NO: 16; total length: 15 bases) that is complementary to the sequence from 3135 to 3149 sites included in 3'UTR of SEQ ID NO: 4, which represents the mouse Mex3B gene, was used. Furthermore, at both ends of each gapmer type antisense oligonucleotide, 2 bases of LNA (2',4'-BNA) were added and natural DNA was employed as bases filling between gaps while the phosphodiester bond connecting each nucleotide was phosphorothioated.

On Day 21, Day 22, and Day 23, all mice were forced to inhale an aerosol which consists of 0.1% OVA in PBS (7 mice/group). Furthermore, as a control group (i.e., control), inhalation of an aerosol, which consists of PBS, was carried out (4 mice/group).

On Day 24, samples were collected and the numbers of the various types of immune cells in bronchoalveolar lavage fluid was measured. The results are shown in FIG. 5.

Figure 5:
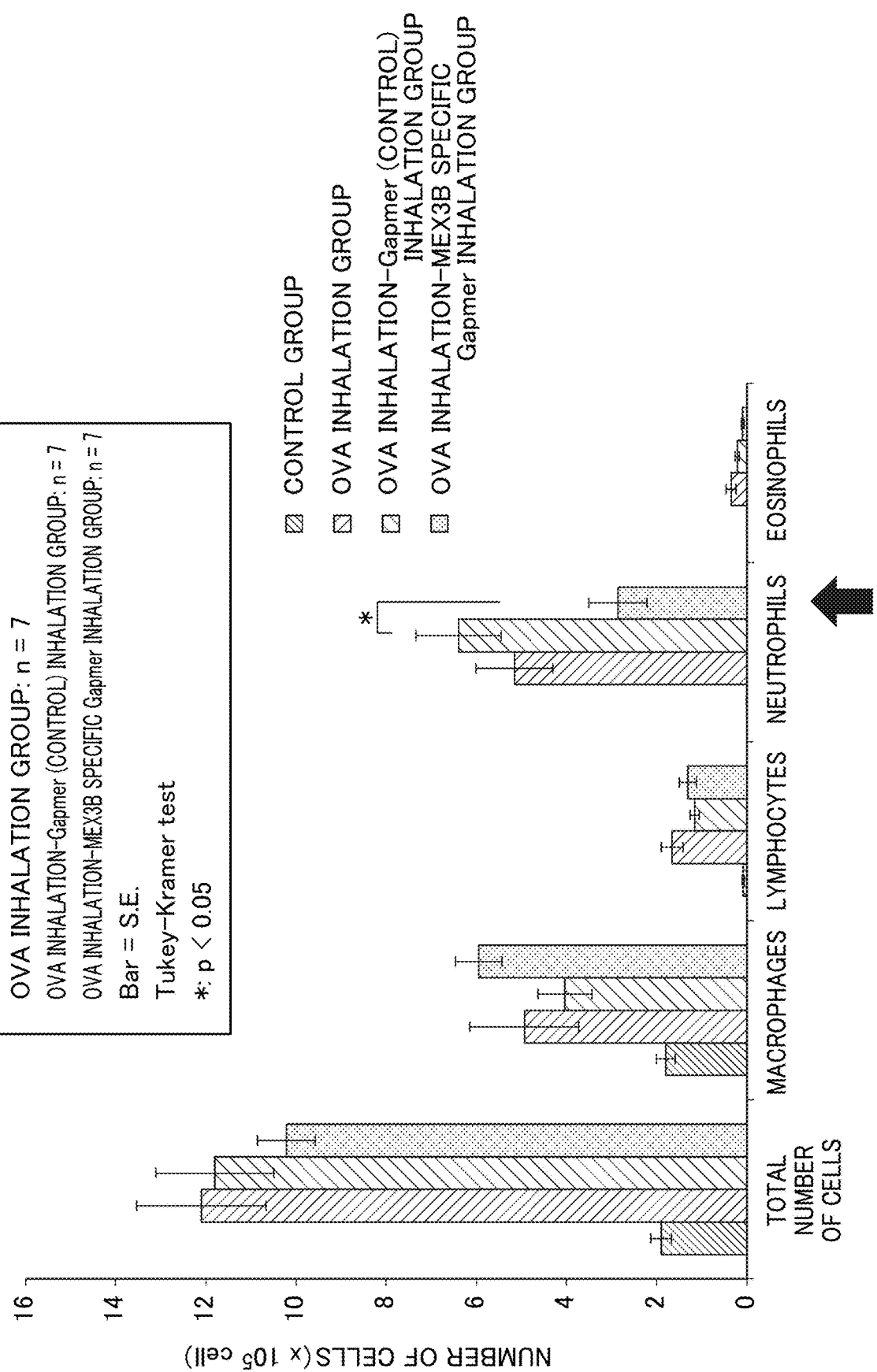
FIG. 5 is a view showing the result of determining an increase in various immune cells in a test of administering gapmer type antisense oligonucleotide in the severe asthma model.

In FIG. 5, the control group represents the cell numbers in the mice which have inhaled PBS as a control, OVA inhalation group represents the cell numbers in the mice which have inhaled OVA, OVA inhale-gapmer (control) inhalation group represents the cell numbers in the mice which have inhaled OVA after inhaling in advance the gapmer (control), and OVA inhale-MEX3B specific gapmer inhalation group represents the cell numbers in the mice which have inhaled OVA after inhaling in advance the MEX3B specific gapmer.

As it is evident from the results shown in FIG. 5, in the severe asthma model, the mouse group which has inhaled OVA showed both increased total cell number and increased macrophage number compared to control, and sensitized with OVA. Furthermore, as the neutrophil number has increased in the mouse group which has inhaled the gapmer (control) in advance, it is demonstrated that severe asthma is induced.

On the contrary, as the neutrophil number has decreased in the mouse group which has inhaled the MEX3B specific gapmer and there was significant difference, it is demonstrated that the symptoms of severe asthma are ameliorated.

Accordingly, it is demonstrated that a MEX3B specific gapmer functions as a prophylactic or therapeutic agent for diseases that are caused by IL-6, IL-13, TNF, G-CSF, CXCL1, CXCL2, or CXCL5.

(Quantitative RT-PCR Test)

Figure 6:
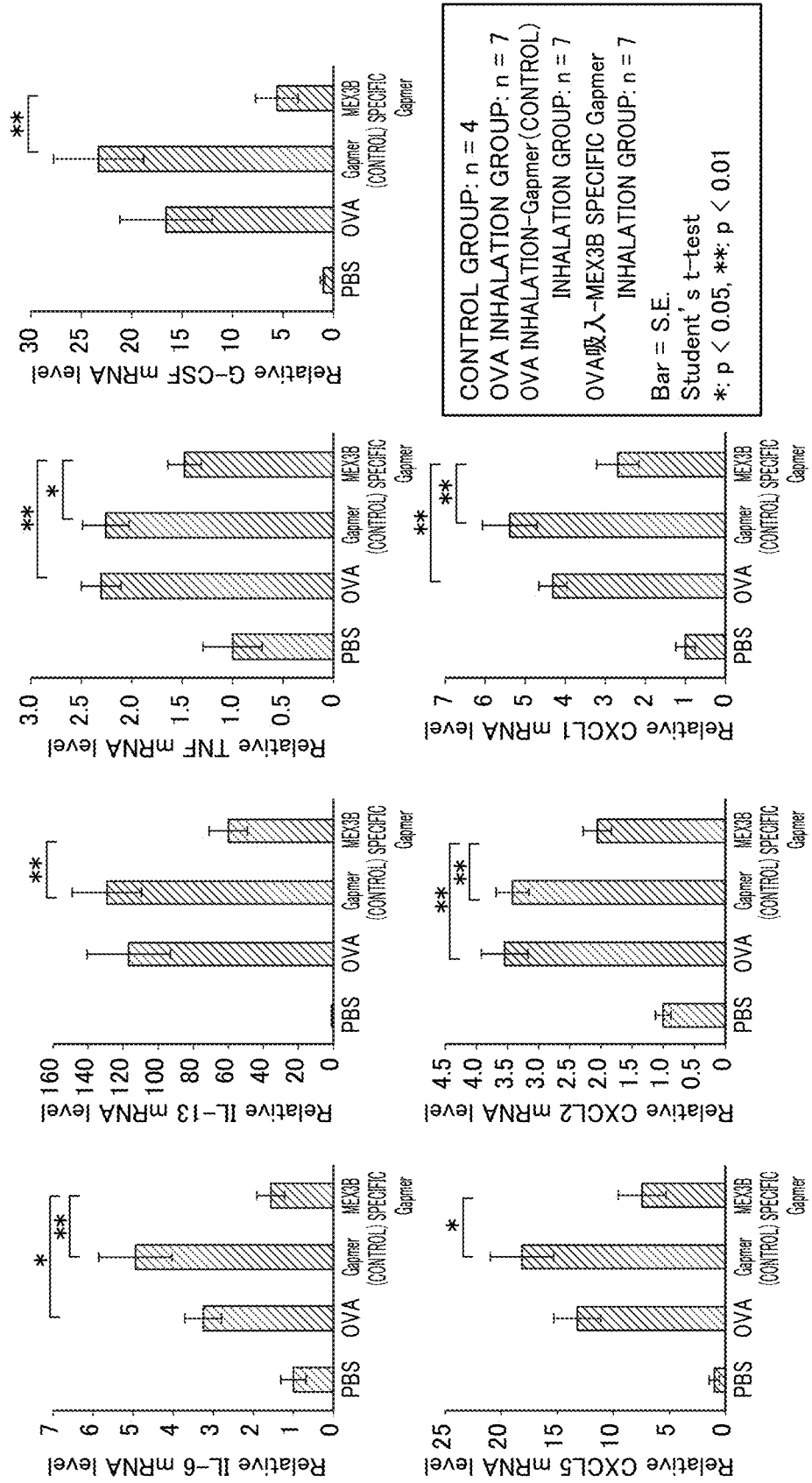
FIG. 6 is a view showing the result of a quantitative RT-PCR test for mRNA expression level of each of the cytokines and chemokines in each mouse group.

Lung tissues were removed from the mice of each group and they were disrupted by a polytron homogenizer in a TRIsure (manufactured by Bioline) solution. According to the product protocol, total RNA was collected and an amplification reaction was carried out by using PCR primers that are shown in the following Table 1. Then, expression level of mRNA of each cytokine (IL-6, IL-13, TNF, and G-CSF) and each chemokine (CXCL1, CXCL2, and CXCL5) was measured. The results are shown in FIG. 6.

TABLE 1

| PCR primer | Sequence of PCR primer | SEQ ID NO |
| --- | --- | --- |
| MouseGAPDH-Fw2 | TGTGTCCGTCGTGGATCTGA | 17 |
| MouseGAPDH-Rv2 | TTGCTGTTGAAGTCGCAGGAG | 18 |

TABLE 1-continued

| PCR primer | Sequence of PCR primer | SEQ ID NO |
| --- | --- | --- |
| MouseTNF-Fw | TCTTCTCATTCCTGCTTGTGG | 19 |
| MouseTNF-Rv | GAGGCCATTTGGGAACTTCT | 20 |
| MouseG-CSF-Fw | CCTGGAGCAAGTGAGGAAGA | 21 |
| MouseG-CSF-Rv | GGGGTGACACAGCTTGTAGG | 22 |
| MouseIL-6-Fw | GCTACCAAACTGGA TATAATCAGGA | 11 |
| MouseIL-6-Rv | CCAGGTAGCTATG GTACTCCAGAA | 12 |
| MouseIL-13-Fw | CCTCTGACCCTTAAGGAGCTTAT | 23 |
| MouseIL-13-Rv | CGTTGCACAGGGGAGTCT | 24 |
| MouseCXCL5-Fw | CAGAAGGAGGTCTGTCTGGA | 13 |
| MouseCXCL5-Rv | TGCATTCCGCTTAGCTTTCT | 14 |
| MouseCXCL2-Fw | AAAATCATCCAAAA GATACTGAACAA | 25 |
| MouseCXCL2-Rv | CTTTGGTTCTTCCGTTGAGG | 26 |
| MouseCXCL1-Fw | AGACTCCAGCCACACTCCAA | 27 |
| MouseCXCL1-Rv | TGACAGCGCAGCTCATTG | 28 |

As it is evident from the results shown in FIG. 6, because the expression of all of IL-6, IL-13, TNF, G-CSF, CXCL5, CXCL1, and CXCL2 has significantly increased in the OVA inhalation group compared to the PBS inhalation group, it was confirmed that the severe asthma model was induced as expected. Furthermore, compared to the gapmer (control) administration group, expression level of IL-6, IL-13, TNF, G-CSF, CXCL5, CXCL1, and CXCL2 tends to decrease in the MEX3B specific gapmer administration group and there were significant differences between control and MEX3B specific gapmer administration groups, and it was shown that, by inhibiting the expression of the MEX3B, those inflammatory factors can be inhibited.

(Pathological Tissue Analysis of Lung Tissues)

Collected mouse lung tissues were fixed with 10% formalin solution, and then embedded in paraffin (Tissue-Tek). Thin slicing was carried out by using a microtome (manufactured by LEICA), and the thin slice was adhered onto a slide glass having APS (aminosilane) coating (manufactured by Matsunami) and subjected to H&E staining (hematoxylin and eosin staining) according to a standard protocol (reference document: Cell Rep. 2016 Aug. 30; 16 (9): 2456-71). The pathological tissue images were photographed by using an Olympus microscope system. The results are shown in FIG. 7.

FIG. 7 is a view showing the pathological tissue image of the lung tissues in each mouse group, in which degree of the inflammation response in lung tissues is shown.

As it is evident from the results shown in FIG. 7, according to the outer appearance, an inflammation response has not occurred in the control inhalation group (i.e., PBS aerosol inhalation), which is the same as the mouse not received any treatment, and significant infiltration of immune cells was not shown. From the OVA inhale-PBS administration group and OVA inhale-control gapmer administration group, thickening of bronchial epithelial cells and significant infiltration of immune cells were observed, clearly indicating that an inflammation was caused.

On the other hand, the OVA inhale-MEX3B specific gapmer administration group, which is a group administered with a gapmer exhibiting the effect of inhibiting Mex3b, showed the almost same results as the control inhalation group, and it exhibited no inflammation. Those results suggest that, according to administration of an MEX3B specific gapmer, onset of asthma that is resistant to steroids is dramatically inhibited. As such, it is demonstrated that the MEX3B specific gapmer can function as a prophylactic or therapeutic agent for diseases that are caused by IL-6, IL-13, TNF, G-CSF, CXCL1, CXCL2, or CXCL5.

SEQUENCE LISTING

ATF-207_ST25.txt

The invention claimed is:

1. A therapeutic method for a respiratory disease or a pulmonary disease, comprising the steps of:
 administering a substance for decreasing expression of MEX3B gene to a patient with a respiratory disease or a pulmonary disease, wherein the substance for decreasing of the MEX3B gene is
 an antisense oligonucleotide which has a sequence complementary to an oligonucleotide comprising at least 10 contiguous nucleotides contained in the MEX3B gene or in an expression control region of the gene;
 a double-stranded RNA containing at least 20 contiguous nucleotides in a coding region or an untranslated region in the sequence of an RNA to be transcribed from the sequence of the MEX3B gene, or a DNA encoding the double-stranded RNA; or
 an artificial nuclease that is CRISPR/Cas nuclease,
 wherein the CRISPR/Cas nuclease comprises a guide RNA having a sequence complementary to a partial sequence of 15 to 25 bases of the MEX3B gene and Cas nuclease;
 wherein the MEX3B gene is a gene consisting of the sequence described in SEQ ID NO: 1 or 4 of the Sequence Listing.

2. The method according to claim 1, wherein the substance for decreasing of the MEX3B gene is administered together with a carrier for lipofection.

3. The method according to claim 1, wherein the respiratory or pulmonary disease is severe asthma caused by interleukin 6, interleukin 13, TNF, G-CSF, CXCL1, CXCL2, or CXCL5.

4. The method according to claim 1, wherein the CRISPR/Cas nuclease is CRISPR/Cas9.

* * * * *